(12) United States Patent
Kallunki et al.

(10) Patent No.: US 10,647,763 B2
(45) Date of Patent: May 12, 2020

(54) AGENTS, USES AND METHODS FOR THE TREATMENT OF SYNUCLEINOPATHY

(71) Applicant: H. Lundbeck A/S, Valby (DK)

(72) Inventors: Pekka Kallunki, Valby (DK); Karina Fog, Valby (DK); Louise Buur Vesterager, Valby (DK); Ann-Louise Bergström, Valby (DK); Florence Sotty, Valby (DK); David Satijn, Utrecht (NL); Edward Van Den Brink, Utrecht (NL); Paul Parren, Utrecht (NL); Rik Rademaker, Utrecht (NL); Tom Vink, Utrecht (NL); Ibrahim John Malik, Valby (DK); Liliana Christina Pereira Montezinho, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/443,187

(22) Filed: Jun. 17, 2019

(65) Prior Publication Data
US 2019/0367594 A1  Dec. 5, 2019

Related U.S. Application Data

(62) Division of application No. 15/207,859, filed on Jul. 12, 2016.

(30) Foreign Application Priority Data

Jul. 13, 2015 (GB) .................................. 1512203.9

(51) Int. Cl.
| | | |
|---|---|---|
| *A61K 39/395* | (2006.01) | |
| *C07K 16/18* | (2006.01) | |
| *A61K 51/00* | (2006.01) | |
| *A61P 25/16* | (2006.01) | |
| *A61P 25/28* | (2006.01) | |
| *G01N 33/68* | (2006.01) | |
| *A61K 39/00* | (2006.01) | |

(52) U.S. Cl.
CPC .......... *C07K 16/18* (2013.01); *A61K 39/3955* (2013.01); *A61K 51/00* (2013.01); *A61P 25/16* (2018.01); *A61P 25/28* (2018.01); *G01N 33/6896* (2013.01); *A61K 2039/505* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2800/2835* (2013.01)

(58) Field of Classification Search
CPC ............... C07K 16/18; C07K 2317/34; C07K 2317/56; C07K 2317/565; A61K 39/3955
See application file for complete search history.

(56) References Cited

U.S. PATENT DOCUMENTS 10,358,483 B2 * 7/2019 Kallunki et al. ....... C07K 16/18

* cited by examiner

*Primary Examiner* — Robert C Hayes

(74) *Attorney, Agent, or Firm* — Nelson Mullins Riley & Scarborough LLP; Jane E. Remillard, Esq.; Christopher L. Frank

(57) ABSTRACT

The invention relates to novel monoclonal anti-alpha-synuclein antibodies. The antibodies can be used for treating a synucleinopathy such as Parkinson's disease (including idiopathic and inherited forms of Parkinson's disease), Diffuse Lewy Body Disease (DLBD), Lewy body variant of Alzheimer's disease (LBV), Combined Alzheimer's and Parkinson disease, pure autonomic failure and multiple system atrophy.

14 Claims, 46 Drawing Sheets

Specification includes a Sequence Listing.

| Antibody | Immunogen | Protocol | Mouse strain | |
|---|---|---|---|---|
| GM37 | FL human Alpha-synuclein fibrils Alternating with 1-60 alpha-synuclein 1-119 alpha-synuclein | Complete Freunds adjuvant and imcomplete Freunds adjuvant | HCo17-Balb/c | |
| GM285 | FL human alpha-synuclein monomer followed by fibrils or monomer | Complete Freunds adjuvant and imcomplete Freunds adjuvant | HCo12-Balb/c | |

FIG. 1

| Name | KA(1/M) | KD(nM) | Rmax | Chi2 |
|---|---|---|---|---|
| hIgG1-6004-037 C106S | 2.33E+08 | 4.29 | 61.1 | 0.96 |

| Name | KA(1/M) | KD(nM) | Rmax | Chi2 |
|---|---|---|---|---|
| hIgG1-6004-085 | 2.33E+08 | 4.30 | 56.3 | 0.77 |

↓
MDVFMKGLSK AKEGVVAAAE KTKQGVAEAA GKTKEGVLYV GSKTKEGVVH
GVATVAEKTK EQVTNVGGAV VTGVTAVAQK TVEGAGSIAA ATGFVKKDQL
GKNEEGAPQE GILEDMPVDP DNEAYEMPSE EGYQDYEPEA (SEQ ID NO:10)
         ↑          ↑                    ↑

FIG. 6

MDVFMKGLSK AKEGVVAAAE KTKQGVAEAA GKTKEGVLYV GSKTKEGVVH
GVATVAEKTK EQVTNVGGAV VTGVTAVAQK TVEGAGSIAA ATGFVKKDQL
GKNEEGAPQE GILEDMPVDP DNEAYEMPSE EGYQDYEPEA (SEQ ID NO:10)
                ↑           ↑                    ↑

```
                            1          10         20         30         40
α-synuclein (P37840)   MDVFMKGLSK AKEGVVAAAE KTKQGVAEAA GKTKEGVLYV
β-synuclein (Q16143)   MDVFMKGLSK AKEGVVAAAE KTKQGVAEAA EKTKEGVLYV
γ-synuclein (O76070)   MDVFKKGFSI AKEGVVGAVE KTKQGVTEAA EKTKEGVMYV 41         50         60         70         80
α-synuclein (P37840)   GSKTKEGVVH GVATVAEKTK EQVTNVGGAV VTGVTAVAQK
β-synuclein (Q16143)   GSKTREGVVQ GVASVAEKTK EQASHLGGAV FSG.......
γ-synuclein (O76070)   GAKTKENVVQ SVTSVAEKTK EQANAVSEAV VSSVNTVATK 81         90        100         112        120
α-synuclein (P37840)   TVEGAGSIAA ATGFVKKDQL GKNEEG     AP QEGILE
β-synuclein (Q16143)   ....AGNIAA ATGLVKREEF PTDLKPEEVA QEA AEEPLI
γ-synuclein (O76070)   TVEGAENIAV TSGVVRKEDL RPSAPQQEGE ASKEKEEVAE 121        130        140    146
α-synuclein (P37840)   DMPVDPDNEA YEMPSEEGYQ DYEPEA       (SEQ ID NO:10)
β-synuclein (Q16143)   EPLMEPEGES YEDPPQEEYQ EYEPEA       (SEQ ID NO:37)
γ-synuclein (O76070)   EAQSGGD...........................(SEQ ID NO:38)
```

FIG. 21

```
                        1          10         20         30         40
Human  (P37840)    MDVFMKGLSK AKEGVVAAAE KTKQGVAEAA GKTKEGVLYV
Cyno   (P61142)    MDVFMKGLSK AKEGVVAAAE KTKQGVAEAA GKTKEGVLYV
Rat    (P37377)    MDVFMKGLSK AKEGVVAAAE KTKQGVAEAA GKTKEGVLYV
Mouse  (O55042)    MDVFMKGLSK AKEGVVAAAE KTKQGVAEAA GKTKEGVLYV 41         50         60         70         80
Human  (P37840)    GSKTKEGVVH GVATVAEKTK EQVTNVGGAV VTGVTAVAQK
Cyno   (P61142)    GSKTKEGVVH GVATVAEKTK EQVTNVGGAV VTGVTAVAQK
Rat    (P37377)    GSKTKEGVVH GVATVAEKTK EQVTNVGGAV VTGVTAVAQK
Mouse  (O55042)    GSKTKEGVVH GVATVAEKTK EQVTNVGGAV VTGVTAVAQK 81         90        100        110        120
Human  (P37840)    TVEGAGSIAA ATGFVKKDQL GKNEEGAPQE GILEDMPVDP
Cyno   (P61142)    TVEGAGSIAA ATGFIKKDQL GKNEEGAPQE GILEDMPVDP
Rat    (P37377)    TVEGAGNIAA ATGFVKKDQL GKCEEGVPQE GILEDMPVDP
Mouse  (O55042)    TVEGAGNIAA ATGFVKKDQL GKCEEGVPQE GILEDMPVDP 121        130        140
Human  (P37840)    DNEAYEMPSE EGYQDYEPEA   (SEQ ID NO:10)
Cyno   (P61142)    DNEAYEMPSE EGYQDYEPEA   (SEQ ID NO:39)
Rat    (P37377)    SSEAYEMPSE EGYQDYEPEA   (SEQ ID NO:40)
Mouse  (O55042)    CSEAYEMPSE EGYQDYEPEA   (SEQ ID NO:41)
```

FIG. 22

| Product | Lot Number | Concentration * (mg/ml) | Volume * (ml) | Yield* (mg) | Titre † (Mg/L) |
|---|---|---|---|---|---|
| GM37_wt | 319-121115-01 | 2.11 | 6.0 | 12.6 | 31.6 |
| GM37_var1 | 319-121115-02 | 1.70 | 5.0 | 8.5 | 21.2 |
| GM37_var2 | 319-121115-03 | 2.57 | 5.8 | 14.9 | 37.2 |
| GM37_var3 | 319-121115-04 | 1.85 | 5.0 | 9.3 | 23.2 |

FIG. 23

| Sample | Ka (1/Ms) | Kd (1/s) | KD (nM) | Rmax (RU) | Chi² (RU²) | U-Value |
|---|---|---|---|---|---|---|
| GM37_wt, batch 2 | 7,01E+05 | 1,92E-02 | 27 | 1,4 | 0,0022 | 3 |
| GM37_wt, batch 1 | 5,28E+05 | 1,48E-02 | 28 | 1,5 | 0,0024 | 2 |
| GM37_Variant 1 | 6,34E+05 | 1,37E-02 | 22 | 1,5 | 0,0022 | 2 |
| GM37_Variant 2 | 4,15E+05 | 1,24E-02 | 30 | 1,4 | 0,0021 | 3 |
| GM37_Variant 3 | 5,77E+05 | 2,28E-02 | 40 | 1,5 | 0,0016 | 2 |
| Isotype control | | | NB | NB | | |

FIG. 25

AGENTS, USES AND METHODS FOR THE TREATMENT OF SYNUCLEINOPATHY

RELATED APPLICATIONS

This application is a divisional of U.S. patent application Ser. No. 15/207,859, filed Jul. 12, 2016, which claims priority to Britist Patent Application No. GB 1512203.9, filed Jul. 13, 2015. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jun. 17, 2019, is named LBJ_001DV5_Sequence_Listing.txt and is 41,524 bytes in size.

FIELD OF THE INVENTION

The present invention relates to a novel class of monoclonal antibody that specifically binds to alpha-synuclein, as well as to methods of using these molecules and their alpha-synuclein binding fragments in the treatment and diagnosis of synucleinopathies.

REFERENCE TO SEQUENCE LISTING

This application includes one or more Sequence Listings pursuant to 37 C.F.R. 1.821 et seq., which are disclosed in computer-readable media (file name: 0992_ST25.txt, created on 22 Jun. 2016, and having a size of 44 kB), which file is herein incorporated by reference in its entirety.

BACKGROUND OF THE INVENTION

Synucleinopathies, also known as Lewy body diseases (LBDs), are characterized by deposition of intracellular protein aggregates that are microscopically visible as Lewy bodies (LBs) and/or Lewy neurites, where the protein alpha-synuclein is the major component (Jellinger, Mov Disord. 2012 January; 27(1):8-30; McKeith et al., Neurology (1996) 47:1113-24). Synucleinopathies include Parkinson's disease (PD) (including idiopathic and inherited forms of Parkinson's disease) and Diffuse Lewy Body (DLB) disease (also known as Dementia with Lewy Bodies (DLB), Lewy body variant of Alzheimer's disease (LBV), Combined Alzheimer's and Parkinson disease (CAPD), pure autonomic failure (PAF) and multiple system atrophy (MSA; e.g., Olivopontocerebellar Atrophy, Striatonigral Degeneration and Shy-Drager Syndrome)). Synucleinopathies frequently have degeneration of the dopaminergic nigrostriatal system, responsible for the core motor deficits in Parkinsonism (rigidity, bradykinesia, resting tremor), but there is also widespread occurrence of Lewy bodies and dystrophic Lewy neurites in the central, peripheral and autonomic nervous system and brain regions and other organs associated with non-motor dysfunctions, such as dementia and autonomic nervous system deficits. Several of the non-motor signs and symptoms are thought to precede motor symptoms in Parkinson's disease and other synucleinopathies. Such early signs include, for example, REM sleep behaviour disorder (RBD) and loss of smell and constipation (Mahowald et al., Neurology (2010) 75:488-489). Synucleinopathies continue to be a common cause for movement disorders and cognitive deterioration in the aging population (Galasko et al., Arch. Neurol. (1994) 51:888-95).

Alpha-synuclein is a member of a family of proteins including beta- and gamma-synuclein and synoretin. Alpha-synuclein is expressed in the normal state associated with synapses and is believed to play a role in regulating synaptic vesicle release and thereby affecting neural communication, plasticity, learning and memory.

Several studies have implicated alpha-synuclein with a central role in PD pathogenesis. The protein can aggregate to form intracellular insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene as well as duplications and triplications of the gene co-segregate with rare familial forms of parkinsonism (Kruger et al., Nature Gen. (1998) 18:106-8; Polymeropoulos, et al., Science (1997) 276:2045-7). An important finding has been that alpha-synuclein can be secreted into the extracellular fluid and be present in plasma and cerebrospinal fluid (CSF). Several studies, for example by Pacheco et al. (2015) and others (Pacheco et al J Neurochem. 2015 March; 132(6): 731-4; Conway et al., Proc Natl Acad Sci USA (2000) 97:571-576; Volles et al., J. Biochem. 42:7871-7878, 2003) have suggested that extracellular-synuclein plays a pathogenic role in the brain. They demonstrated that extracellular alpha-synuclein oligomers possesses neurotoxicity toward brain neuronal plasma membranes. Another intriguing hypothesis based on the data of synuclein secretion is that a prion-like spread of alpha-synuclein underlies the progression of Parkinson's disease and other synucleinopathies (Lee et al. 2014, Nat Rev Neurol. 2014 February; 10(2):92-8; Hansen and Li 2012, Trends Mol Med. 2012 May; 18(5): 248-55). These findings have given rise to a hope that extracellular-synuclein could be targeted by immunotherapy (Vekrellis et al. 2011, Lancet Neurol. 2011 November; 10(11):1015-25).

Naturally occurring alpha-synuclein auto-antibodies have been shown to be present in both PD patients and healthy controls (Smith et al. 2012, PLoS One. 2012; 7(12):e52285; Maetzler et al. 2014, PLoS One. 2014 Feb. 21; 9(2):e88604, Papachroni et al. 2007 J Neurochem. 2007 May; 101(3): 749-56 and Woulfe et al. 2002, Neurology. 2002 May 14; 58(9):1435-6), sometimes increased levels of auto-antibodies to alpha-synuclein in PD (Gruden et al. 2011, J Neuroimmunol. 2011 April; 233(1-2):221-7, Gruden et al. 2012, Neuroimmunomodulation. 2012; 19(6):334-42 and Yanamandra 2011, PLoS One. 2011 Apr. 25; 6(4):e18513) or decreased auto-antibodies to alpha-synuclein in PD patients compared to healthy controls have been reported (Besong-Agbo et al 2013, Neurology. 2013 Jan. 8; 80(2):169-75). The possibility that circulating anti-alpha-synuclein autoantibodies may serve a protective role with respect to alpha-synuclein aggregation was suggested very early on after finding of the auto-antibodies (Woulfe et al. 2002, Neurology. 2002 May 14; 58(9):1435-6).

Over expression of alpha-synuclein in transgenic mice mimics some pathological aspects of Lewy body disease. Several different transgenic lines of mice over-expressing alpha-synuclein have been generated in the last ten years (described in reviews: Koehler et al 2014, PLoS One. 2013 May 31; 8(5):e64649; Fleming and Chesselet, 2006, Behav Pharmacol. 2006 September; 17(5-6):383-91; Springer and Kahle 2006, Curr Neurol Neurosci Rep. 2006 September; 6(5):432-6). Mouse lines with Thy-1 and PDGF-beta promoters develop motor deficits and cognitive deficits and have been used to demonstrate a neuroprotective effect of antibodies directed against alpha-synuclein in vivo. However, none of the transgenic lines have robust degeneration of dopaminergic neurons, and often the motor phenotypes are driven by expression in motor neurons, which do not normally degenerate in Parkinson's disease. Therefore, it is not clear if positive outcome of a potential disease modifying treatment is mediated through effects on dopaminergic neurons or other central nervous system neurons.

One robust finding in the transgenic mouse models has been that chronic overexpression of human alpha-synuclein impairs synaptic function. Using studies in both in vitro and in vivo systems it was shown that overexpression of wild-type (wt) human alpha-synuclein impaired synaptic transmission in hippocampus (Nemani et al. 2010, Neuron. 2010 Jan. 14; 65(1):66-79; Paumier et al. 2013, PLoS One. 2013 Aug. 1; 8(8):e70274). This was shown in the CA1 region of the hippocampus where both studies found reduced basal synaptic transmission. The mechanism behind this was assumed to be intracellular accumulation of alpha-synuclein leading to dysfunctional synaptic release. However, the recent findings about secretion of alpha-synuclein into extracellular space in synapses and the toxic effects of alpha-synuclein oligomers on synapse function opens for the possibility of a role of extracellular alpha-synuclein in synaptic dysfunction, and as such for the ability of therapeutic antibodies to rescue the deficit.

The use of viral vectors to over-express alpha-synuclein represents an important way to model PD in rodents because this approach produces a relative fast progressive degeneration of nigrostriatal neurons, a feature not yet reproduced by genetic mutations in mice or rats (Kirik and Bjorklund, 2003, Trends Neurosci. 2003 July; 26(7):386-92). Furthermore, viral gene delivery revealed the ability of wt alpha-synuclein to induce nigrostriatal pathology (Kirik et al. 2002, J Neurosci. 2002 Apr. 1; 22(7):2780-91), a finding in agreement with evidence in familial forms of PD with alpha-synuclein dublications and triplications (Lee and Trojanowski, 2006, Neuron. 2006 Oct. 5; 52(1):33-8). In one study, it has been shown that a a pool of goat antibodies against the alpha-synuclein N-terminal protected against dopaminergic cell death and ameliorated behavioural deficits in a AAV-alpha-synuclein based rat model of Parkinson's disease (Shahaduzzaman et al 2015, PLoS One. 2015 Feb. 6; 10(2):e0116841).

Prion like spreading of alpha-synuclein pathology has recently been shown to develop alpha-synuclein pathology and also develop dopaminergic cell death (Luk et al. 2012, Science. 2012 Nov. 16; 338(6109):949-53). This model has been used to show that alpha-synuclein antibodies are able to ameliorate the pathology (Tran et al. 2014, Cell Rep. 2014 Jun. 26; 7(6):2054-65). In this model antibody treatment was able to reduce accumulation of phosphorylated alpha-synuclein in several brain regions—including dopaminergic neurons in substantia nigra, and reduce development of motor deficit.

In addition to mutations, alternative splicing of the alpha-synuclein gene and posttranslational modifications of the protein, such as phosphorylation, ubiquitination, nitration, and truncation can create alpha-synuclein protein forms that have enhanced capacity to form aggregated and/or toxic forms of alpha-synuclein (Beyer and Ariza, Mol Neurobiol. 2013 April; 47(2):509-24). However, the precise pathological species of alpha-synuclein remains unknown. Various misfolded/aggregated/secreted species ranging from oligomers to fibrils, and different post-translational modifications have been associated with toxicity but there is no consensus on which is most important, if indeed there even is a single toxic species.

Overall the accumulation of alpha-synuclein with similar morphological and neurological alterations in animal models as diverse as humans, mice, and flies suggests that this molecule is central in the pathogenesis of Lewy body diseases.

Several different antibodies to alpha-synuclein have been shown to have therapeutic effect in preclinical animal models. Both an antibody targeting an epitope involving alpha-synuclein residues 91-99 and antibodies targeting an epitope that involves alpha-synuclein residues 118-126 have been shown to have an effect on motor and cognitive deficits in transgenic mice (Games et al. 2014, J Neurosci. 2014 Jul. 9; 34(28):9441-54). The most advanced of these antibodies is a humanized antibody based on the mouse monoclonal antibody 9E4, which targets an epitope that involves alpha-synuclein residues 118-126, and which is now in clinical trials in phase I. A C-terminal antibody 274 which targets an epitope that involves alpha-synuclein residues 120-140 (Bae et al. 2012, J Neurosci. 2012 Sep. 26; 32(39):13454-69) was also shown to have an effect in a preclinical model on spreading of the pathology from cell to cell. In addition to these, antibodies targeting conformational species such as oligomers and fibrils of alpha-synuclein have been shown to be able to at least reduce the levels of these presumably toxic alpha-synuclein species (Lindstrom et al. 2014, Neurobiol Dis. 2014 September; 69:134-43 and Spencer et al. 2014, Mol Ther. 2014 October; 22(10):1753-67). These conformational antibodies that lower alpha-synuclein oligomer levels in vivo, such as mab47 were also shown to target epitopes in the C-terminus of alpha-synuclein, from amino acid 121-125 (US20120308572). Other conformational, fibril and oligomer specific antibodies also target C-terminal sequences (Vaikath et al. Neurobiol Dis. 2015; 79:81-99).

As the toxic form of alpha-synuclein is unknown, a therapeutic antibody should be ideally able to bind to most of the alpha-synuclein species that are formed by alternative splicing or posttranslational modifications, such as truncations, as well as oligomeric and fibrillary forms. One problem with current antibodies that have been tested as therapeutics in preclinical models, as discussed above, is that many of them target C-terminal epitopes, which are not found in some of the major truncated forms of alpha-synuclein. For example, the amino acids that are important for binding of 9E4 are asparagine 122 and tyrosine 125 (according to an alanine scan presented in patent US20140127131), and this means that this antibody cannot bind alpha-synuclein which is truncated at amino acids 119, and 122, which are some of the major truncated species in Parkinson brain tissue (Kellie et al. Sci Rep. 2014; 4:5797). The same would be the case for the antibody 274 and antibody mab47 (U.S. Pat. No. 8,632,776). Also, amino terminal antibodies would possibly not be able to bind to some of the major truncated species that lack the first amino acids of alpha-synuclein, such as alpha-synuclein truncated to amino acids 5-140. For the 9E4 antibody, one suggested mechanism of action is the prevention of truncation at amino acids 119-122 in extracellular space, as the antibody will bind to the same region where the protease that will cleave alpha-synuclein (Games et al. 2014, J Neurosci. 2014 Jul. 9; 34(28):9441-54). A similar mechanism of action could also be found with antibodies in close proximity of the site, and therefore many antibodies around this region would be expected to have this activity.

There is some support for a toxic role of the truncated alpha-synuclein species in animal models. Expression of truncated alpha-synuclein under the tyrosine-hydroxylase promoter has been shown to lead to nigrostriatal pathology, which is normally not seen in transgenic alpha-synuclein models (Tofaris et al. 2006, J Neurosci. 2006 Apr. 12; 26(15):3942-50; Wakamatsu et al. 2006, Neurobiol Aging. 2008 April; 29(4):574-85). For example, expression of amino acids 1-130 of a human alpha-synuclein protein having the A53T mutation caused embryonic loss of dopaminergic neurons in the substantia nigra pars compacta whereas expression of the full length protein did not (Wakamatsu et al. 2006, Neurobiol Aging. 2008 April; 29(4):574-85). Expression of a 120 amino acid alpha-synuclein molecule under the calcium/calmodulin-dependent protein kinase II alpha (CamKII-alpha) promoter was associated with alpha-synuclein aggregation and a progressive deficit in cortical-hippocampal memory tests including the Barnes maze and novel object recognition (Hall et al. 2015, Exp Neurol. 2015 February; 264:8-13). Also in the rat AAV model co-expression of C-terminal truncated alpha-synuclein enhanced full-length alpha-synuclein-induced pathology (Ulusoy et al. 2010, Eur J Neurosci. 2010 August; 32(3):409-22).

In this invention, antibodies (such as "GM37" and "GM285", described in the Examples) have been generated that can bind to the toxic alpha-synuclein fragment 1-119/122 and neutralize this truncated form of alpha-synuclein. The antibodies of the invention, such as GM37 and GM285, are capable of binding to other oligomeric forms of alpha-synuclein and altering their uptake by other CNS resident cells in a manner that reduce the spreading of disease. Furthermore, the antibodies of the invention, such as GM37 and 285, were surprisingly found to be superior to prior art antibodies such as 9E4 in binding to different alpha-synuclein species in human brain, and has a surprising superior effect on clearing extracellular alpha-synuclein and normalising impaired synaptic transmission induced by the presence of abnormal alpha-synuclein in vivo. Further illustrating their therapeutic capabilities, the antibodies of the invention, such as GM37 and 285, are able to prevent the appearance of a disease related motor phenotype in a rat model for Parkinson's disease. Finally, antibodies GM37 and GM285 are able to inhibit seeding of aggregation and phosphorylation of endogenous alpha-synuclein induced by extracellular added recombinant pathological alpha-synuclein seeds in primary mouse neurons. Antibodies such as GM37 and 285 can also inhibit seeding of alpha-synuclein pathology into dopaminergic neurons in vivo using a mouse model for Parkinson's disease, further supporting the therapeutic capability of these antibodies in preventing the cell to cell propagation of pathology. Together these data strongly support the use of these novel antibodies, GM37 and GM285, as new therapeutic agents capable of modifying disease through inhibition of the mechanism by which the disease pathology spreads between the neurons Parkinson's patients.

In a further aspect of the invention is provided 3 amino acid variants of the GM37 antibody. All the variants have similar functional readouts as the parent antibody, GM37, but with improved properties for manufacturability. The variants reduce the risk of post-translational modification occurring within the binding domain of the GM37 antibody and provide some improvement in the production of the antibody. This is advantageous because large scale clinical or commercial manufacturing of antibodies is complicated and expensive, and providing a homogenous product in pharmaceutical medicaments is crucial in particular for immunoglobulins and proteins.

SUMMARY OF THE INVENTION

The invention relates to novel monoclonal antibodies, and antigen-binding fragments thereof, capable of specifically binding an epitope within amino acids 112-117 in alpha-synuclein (SEQ ID NO:9 (ILEDMP)). The epitope bound by the antibodies or antibody-binding fragments thereof of the invention, such as exemplary antibody "GM37", or "GM285", is referred to herein as "the 112-117 epitope". The antibodies of the present invention specifically bind to an epitope within the 112-117 epitope and may, according to one embodiment, compete with antibody GM37 or GM285 for binding to an epitope within amino acids 112-117. For example, antibodies or antigen-binding fragments thereof according to the invention may compete for binding to an epitope within amino acids 112-117 of human alpha-synuclein with a heavy chain consisting of a variable domain of SEQ ID NO:7 and a light chain consisting of a variable domain of SEQ ID NO:8. Such competitive binding inhibition can be determined using assays and methods well known in the art, for example using an unlabelled binding assay such as surface plasmon resonance (SPR). For example, immobilising human alpha-synuclein on a surface and incubating with or without the reference antibody 'GM37' prior to incubation with an antibody or binding fragment to be tested. Alternatively, a pair-wise mapping approach can be used, in which the reference antibody 'GM37' is immobilised to the surface, human alpha-synuclein antigen is bound to the immobilised antibody, and then a second antibody is tested for simultaneous binding ability to human alpha-synuclein (see 'BIAcore® Assay Handbook', GE Healthcare Life Sciences, 29-0194-00 AA 05/2012; the disclosures of which are incorporated herein by reference).

More specifically the GM285 antibody binds an epitope within residues 112-117 of alpha-synuclein comprising residues 112-115 of alpha-synuclein (ILED; SEQ ID NO:19).

In one embodiment, the invention relates to monoclonal antibody GM37, its variants (e.g., GM37 Variant 1, GM37 Variant 2 and GM37 Variant 3), or GM285.

In particular, the invention provides a monoclonal antibody GM37, its variants (e.g., GM37 Variant 1, GM37 Variant 2 and GM37 Variant 3), or GM285, and encompasses such antibodies as well as derivatives thereof that possess a sufficient number (e.g., 1, 2, or 3) light chain CDRs and a sufficient number (e.g., 1, 2, or 3) heavy chain CDRs to form a binding site capable of specifically binding to human synuclein. Preferably, such antibodies will possess the three light chain CDRs and three heavy chain CDRs, as defined below. The numbering of amino acid residues in this region is according to IMGT®, the international ImMunoGeneTics information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and Human Services; Chothia, C. & Lesk, A. M. (1987). Canonical structures For The Hypervariable domains Of Immunoglobulins. J. Mol. Biol. 196, 901-917.

In one embodiment, the monoclonal antibody or antigen-binding fragments thereof possesses a synuclein antigen-binding fragment comprising or consisting of:
(a) a Heavy Chain CDR1 having the amino acid sequence of SEQ ID NO:1; and/or (b) a Heavy Chain CDR2 having the amino acid sequence of SEQ ID NO:2; and/or
(c) a Heavy Chain CDR3 having the amino acid sequence of SEQ ID NO:3; and/or
(d) a Light Chain CDR1 having the amino acid sequence of SEQ ID NO:4; and/or
(e) a Light Chain CDR2 having the amino acid sequence of SEQ ID NO:5; and/or
(f) a Light Chain CDR3 having the amino acid sequence of SEQ ID NO:6;
that is capable of specifically binding to human alpha-synuclein.

In another embodiment, the monoclonal antibody or antigen-binding fragments thereof possesses a synuclein antigen-binding fragment comprising or consisting of:
(a) a Heavy Chain CDR1 having the amino acid sequence of SEQ ID NO:1;
(b) a Heavy Chain CDR2 having the amino acid sequence of SEQ ID NO:33, 34 or 35;
(c) a Heavy Chain CDR3 having the amino acid sequence of SEQ ID NO:3;
(d) a Light Chain CDR1 having the amino acid sequence of SEQ ID NO:4;
(e) a Light Chain CDR2 having the amino acid sequence of SEQ ID NO:5; and
(f) a Light Chain CDR3 having the amino acid sequence of SEQ ID NO:6;
that is capable of specifically binding to human alpha-synuclein.

In yet another embodiment, the monoclonal antibody or antigen-binding fragments thereof possesses a synuclein antigen-binding fragment comprising or consisting of:
(a) a Heavy Chain CDR1 having the amino acid sequence of SEQ ID NO:20; and/or
(b) a Heavy Chain CDR2 having the amino acid sequence of SEQ ID NO:21; and/or
(c) a Heavy Chain CDR3 having the amino acid sequence of SEQ ID NO:22; and/or
(d) a Light Chain CDR1 having the amino acid sequence of SEQ ID NO:23; and/or
(e) a Light Chain CDR2 having the amino acid sequence of SEQ ID NO:24; and/or
(f) a Light Chain CDR3 having the amino acid sequence of SEQ ID NO:25.
that is capable of specifically binding to human alpha-synuclein.

In one embodiment, the monoclonal antibody or antigen-binding fragments thereof possesses a synuclein antigen-binding fragment comprising an amino acid sequence (in its CDRs, its variable domains, its framework residues or in its constant domains) that differs from that of naturally occurring anti-alpha-synuclein antibodies, and that exhibits (relative to such naturally occurring anti-alpha-synuclein antibodies):
(i) a difference in binding affinity (KD) for alpha-synuclein;
(ii) a difference in the capability of inhibiting protease truncation of alpha-synuclein fibrils;
(iii) a difference in the capability of reversing impairment in basal synaptic transmission in F28-snca transgenic mice;
(iv) a difference in the capability of reducing levels of alpha-synuclein in the mouse hippocampus as measured by in vivo microdialysis; and/or
(v) a difference in the capability, when administered chronically, to restore motor function in a rat model of Parkinson's disease
(vi) a difference in the ability to prevent seeding of alpha-synuclein (such as accumulation of insoluble phosphorylated alpha-synuclein in vitro and/or in a mouse model of Parkinson's disease); and/or
(vii) a difference in the capability to bind truncated alpha-synuclein in a human brain.

The antibodies and antigen-binding fragments thereof of the invention may be used in a method to treat, diagnose or image synucleinopathies, such as Parkinson's disease ((PD), including idiopathic and inherited forms of Parkinson's disease), Diffuse Lewy Body Disease (DLBD), Lewy body variant of Alzheimer's disease (LBV), Gauchers Disease (GD), Combined Alzheimer's and Parkinson disease (CAPD), pure autonomic failure and multiple system atrophy.

BRIEF DESCRIPTION OF THE DRAWINGS

FIG. 1 shows immunization protocols for generation of hybridomas. The table outlines the differences of the immunogens and mouse strains used for the identification of GM37 and GM285. Different HCo17-Balb/c and HCo12/Balb/c mice were immunized independently (description of these mice are provided below). The hybridoma expressing GM37 was identified from mice immunized with full length alpha-synuclein containing amino acids 1-140 fibrils and boosted with truncated alpha-synuclein fragments 1-60 and 1-119 of full length (FL) alpha-synuclein (SEQ ID NO 10). The hybridoma expressing antibody GM285 came from an immunization protocol in which HCo12-Balb/c mice were immunized with full length monomeric alpha-synuclein, amino acids 1-140 followed by a boost with full length fibrillary alpha-synuclein (Example 1).

FIG. 2A) Binding of antibody GM37 to alpha-synuclein using a no wash solution based ELISA (FMAT).
FIG. 2B) Using SPR (Fortebio) binding of antibody GM37 is specific for alpha-synuclein (Alpha Panel) and does not bind the other related synuclein family proteins, beta-synuclein (Beta Panel) and gamma-synuclein (Gamma Panel). Measurements were performed using SPR (Fortebio Octetred) GM37 shows similar binding to alpha-synuclein from cynomolgus monkey (Cyno Panel) and mouse (Mouse Panel). (Example 1).
FIG. 2C) Using SPR (Fortebio Octetred) binding of antibody GM285 is specific for alpha-synuclein and does not bind the other related synuclein family proteins, beta-synuclein and gamma-synuclein. Measurements were performed using SPR (Fortebio Octetred) shows similar binding of GM285 to alpha-synuclein from cyno-molgus monkey (Cyno) and mouse (Mouse)(Example 1).

FIG. 3B) Signal from binding at different concentrations converted into a binding curve.
FIG. 3C) Calculated binding constants of antibody GM37 (denoted hIgG1-6004-037-C0106S) (Example 2).

FIG. 4A) Binding of antibody GM285 to alpha-synuclein measured in RU (y-axis) over time (X-axis) as determined by SPR (BIAcore® 3000). Goat anti-human IgG was immobilized on the CM5 chip. GM285 was captured on the Goat anti-human IgG immobilized chip and series of concentrations of human alpha-synuclein (3.125, 6.25, 12.5, 25, 50, 100 nM) were tested on binding to the surface. The sensor surface was regenerated between each cycle.

FIG. 4B) Signal from binding at different concentrations converted into a binding curve.

FIG. 4C) Calculated binding constants of antibody GM285 (denoted hIgG1-6004-285) (Example 2).

FIG. 5A) Shows binding of 9E4 to alpha-synuclein measured in RU (y-axis) over time (X-axis) as determined by SPR (BIAcore® 3000). Goat anti-human IgG was immobilized on the CM5 chip. 9E4 was captured on the chip by its binding to Goat anti-human IgG that had been immobilized to the chip. A series of concentrations of human alpha-synuclein (3.125, 6.25, 12.5, 25, 50, 100 nM) were tested for binding to the surface. The sensor surface was regenerated between each cycle.

FIG. 5B) Signal from binding at different concentrations converted into a binding curve.

FIG. 5C) Calculated binding constants for antibody 9E4. (Example 2).

FIG. 6 shows the amino acid sequence of alpha-synuclein. Major truncation sites (indicated by arrows) identified by mass spectrometry in human brain tissue (Kellie J F, Higgs R E, Ryder J W, Major A, Beach T G, Adler C H, Merchant K, Knierman M D. Quantitative measurement of intact alpha-synuclein proteoforms from post-mortem control and Parkinson's disease brain tissue by mass spectrometry. Sci Rep. 2014 Jul. 23; 4:5797. doi: 10.1038/srep05797)

FIG. 7A) GM37 epitope requires peptide sequence ILEDMP (SEQ ID NO:9) for full binding.

FIG. 7B) GM285 requires peptide ILED (SEQ ID NO:19) for full binding. (Example 3).

FIG. 8A) binding epitopes of GM37/285 (ILEDMP; SEQ ID NO:9) and 9E4 (NEAYE; SEQ ID NO:36) are shown in bold on the alpha-synuclein amino acid sequence (SEQ ID NO:10). Arrows indicates the c-terminal truncations sites from FIG. 6.

FIG. 8B) Major truncated forms of alpha-synuclein that have been identified from human brain material. Size based on amino acid numbers is indicated on the right side. Full length alpha-synuclein is 140 amino acids. As can be deducted from the epitopes, GM37, it's variants 1-3, and GM285 should bind full length and the 1-119/122, 1-135 fragments. Antibody 9E4 will bind only to full length and 1-135 fragment. The specific nature of the smaller c-terminal fragments left after the truncations are not shown.

FIG. 12A) Example of images of primary neurons stained for phosphorylated alpha-synuclein, which appears as spots or punctate staining in cells when the cells are seeded with either 1 ng of pure seeds or crude seeds of alpha-synuclein.

FIG. 12B) Western blot of proteins from primary cortical neurons separated in soluble and insoluble fractions. The blots were stained with human alpha-synuclein specific antibody (4B12/H a-syn), phospho-Ser-129-alpha-synuclein specific antibody (ab51253/pS-a-Syn) and mouse alpha-synuclein specific antibody (D37A2/M a-syn) and show that addition of the crude seeds in primary neurons leads to accumulation of endogenous mouse alpha-synuclein and phosphorylated alpha-synuclein and higher molecular weight multimers of alpha-synuclein in the insoluble fraction.

FIG. 12C) GM37, GM37 variant 2 and GM285 inhibit appearance of phosphorylated alpha-synuclein quantitated as the number of alpha-synuclein phosphoserine 129 positive spots in cells by a Cellomics ARRAYSCAN™ automated microscope. GM37, GM37v2 and GM285 reduce the amount of phosphorylated alpha-synuclein spots in cells in dose dependent manner.

FIG. 12D) Western blot of the homogenates from primary cortical neurons treated at the highest dose of antibody (133 nM), and stained for actin, human alpha-synuclein, phosphorylated alpha-synuclein and mouse alpha-synuclein shows that antibodies 37, 37v2 and 285 inhibit truncation of the alpha-synuclein crude seeds taken up by the cells in the insoluble fraction. All antibodies also inhibit the accumulation of phosphorylated, endogenous mouse and higher molecular weight multimers of phosphorylated mouse alpha-synuclein in the insoluble fraction. The actin band on the top of the gel shows equal loading of the samples (Example 6).

FIG. 20A shows a schematic indicating relative treatment times with respect to seed injection and cell counting. The antibody GM37 was administered one day before injection of recombinant alpha-synuclein fibrillary seeds into dorsal striatum of mice, and then weekly for six weeks. Dosing regimen was either 15 mg/kg iv or 30 mg/kg ip. FIG. 20B shows the exposure level of GM37 in plasma based on site of injection and dose. Weekly samples were taken before the injection of new antibody dose. FIG. 20C shows the exposure level of GM37 in csf based on dose and injection site at the end of the study.

FIG. 21 shows alignment of human α (SEQ ID NO:10), β (SEQ ID NO:37) and γ (SEQ ID NO:38) synuclein proteins. Amino acid residues different from α-synuclein are highlighted. Gaps are indicated by a dot. SwissProt numbers are in parenthesis.

FIG. 22 shows alignment of alpha-synuclein orthologs (Cynomolgus monkey, SEQ ID NO:39; Rat, SEQ ID NO:40; Mouse, SEQ ID NO:41). Amino acid residues different from human alpha-synuclein (SEQ ID NO:10) are highlighted. SwissProt numbers are shown in parenthesis.

FIG. 23 shows transient expression of GM37 (named GM37 wild type (wt) and 3 GM37 variants, named GM37 var 1, 2 and 3. Asterisk indicates that the data are determined post protein A purification and neutralisation. t indicates that data are calculated from yield achieved post protein A and neutralization in relation to scale of expression culture (0.4 L).

FIG. 25 shows a table comparing the binding rate kinetic parameters of GM37 wt and variants 1-3 to immobilized recombinant human alpha-synuclein. The binding was measured using SPR and the rates were determined using a 1:1 binding algorithm (BIAcore® T200).

DETAILED DESCRIPTION OF THE INVENTION

Definitions

Figure 2A:
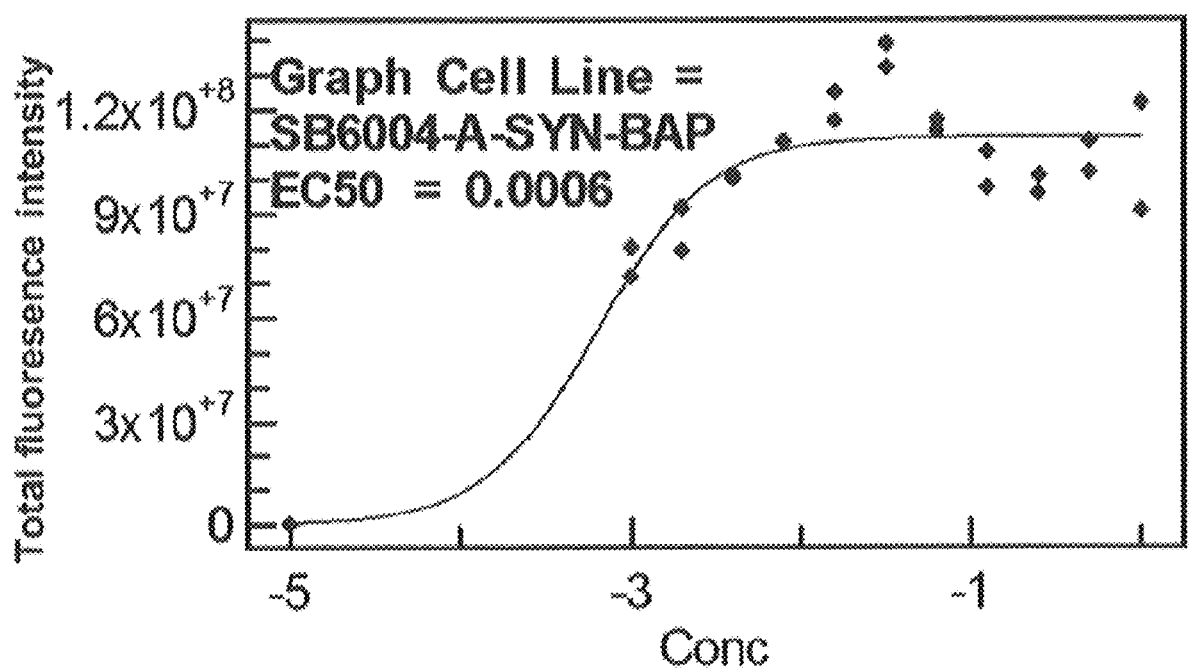
FIGS. 2A-2C show screening of GM37 for binding to alpha synuclein, alpha-synuclein homologs and orthologs.
Figure 2B:
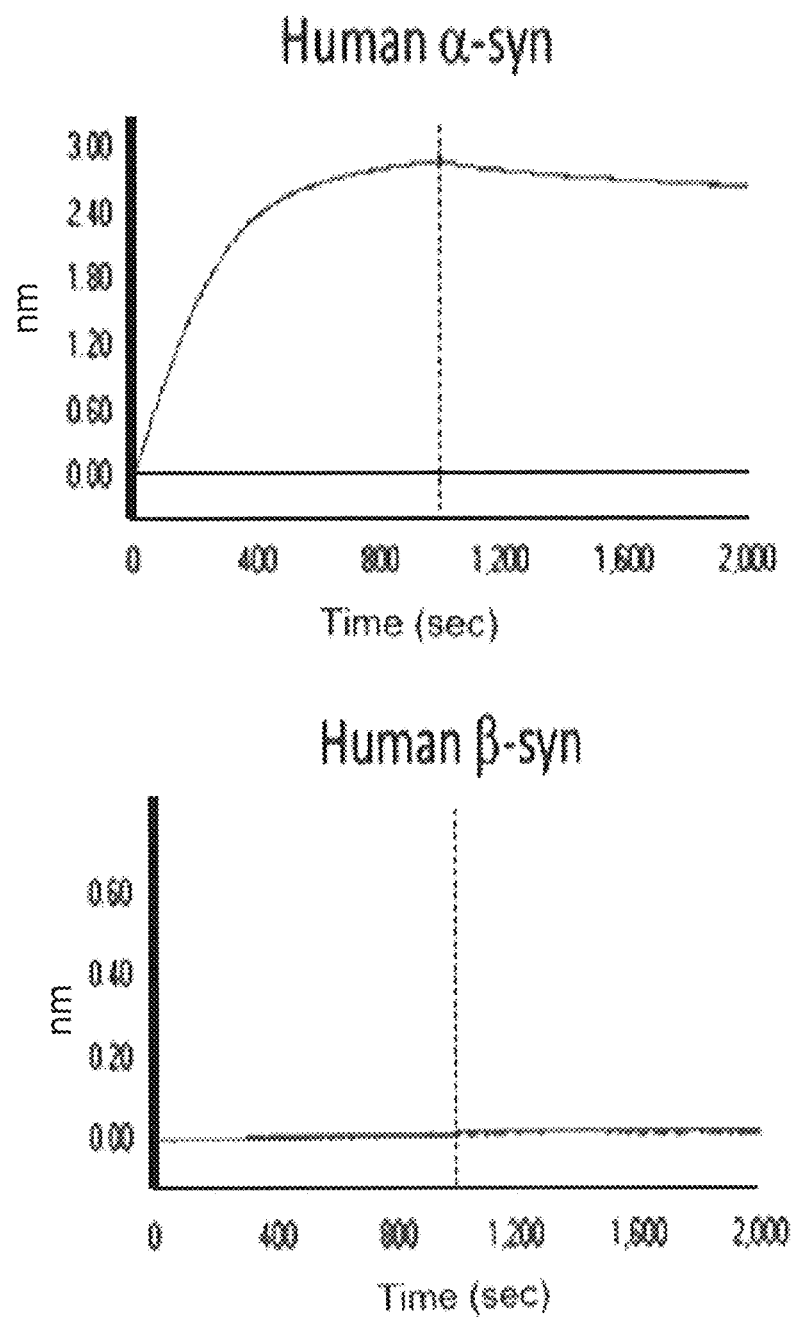
Figure 2B:
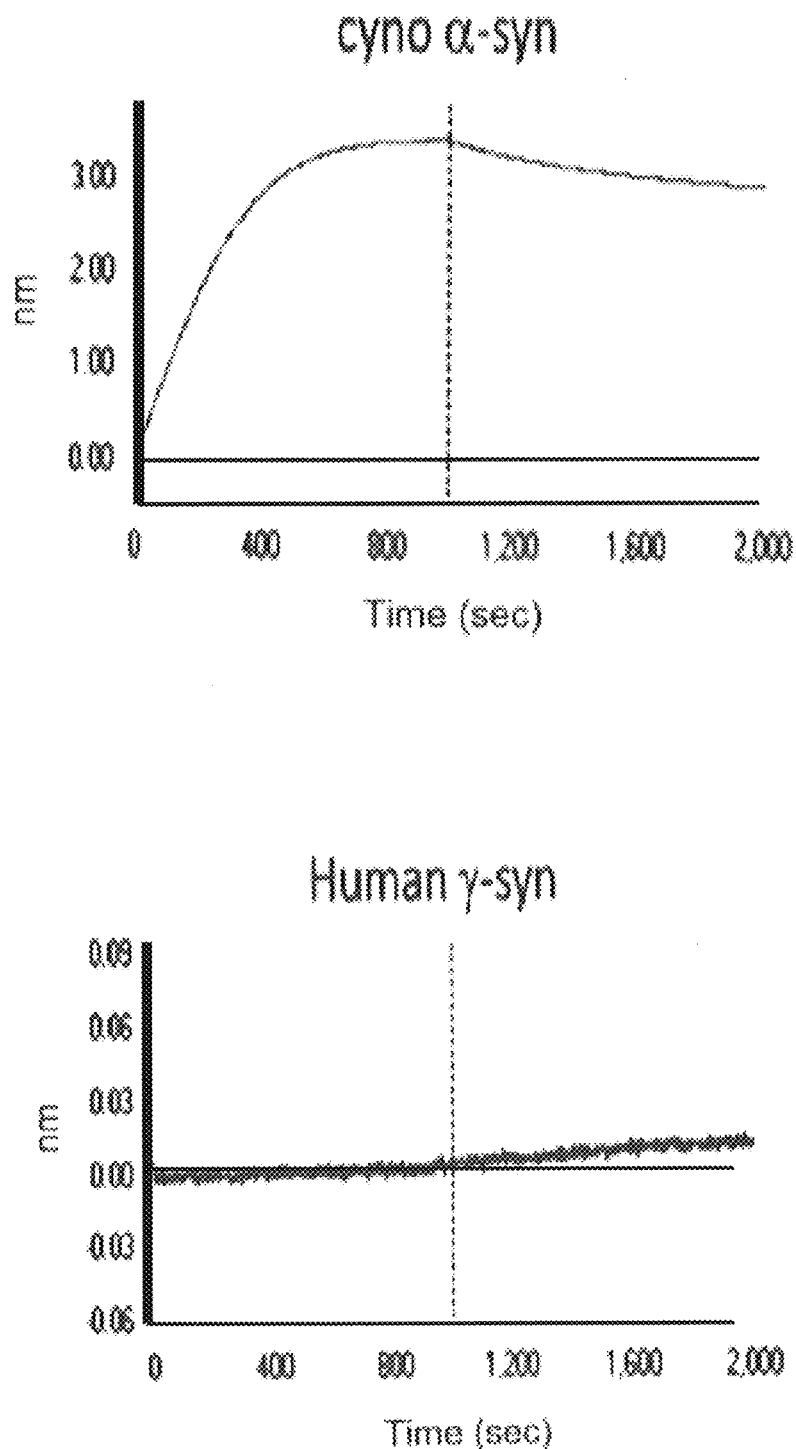
Figure 2B:
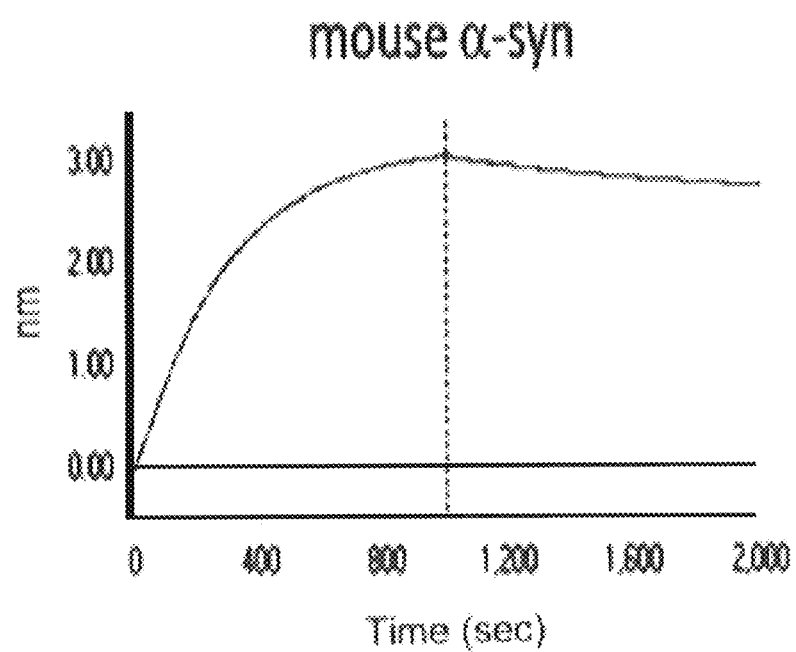
Figure 2C:
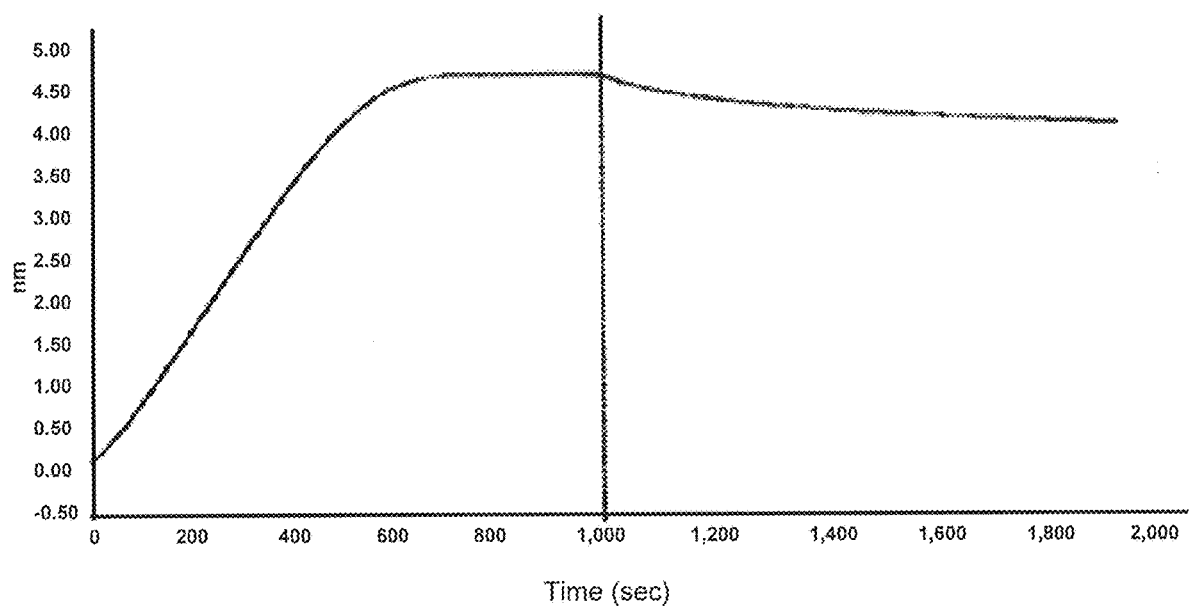
Figure 2C:
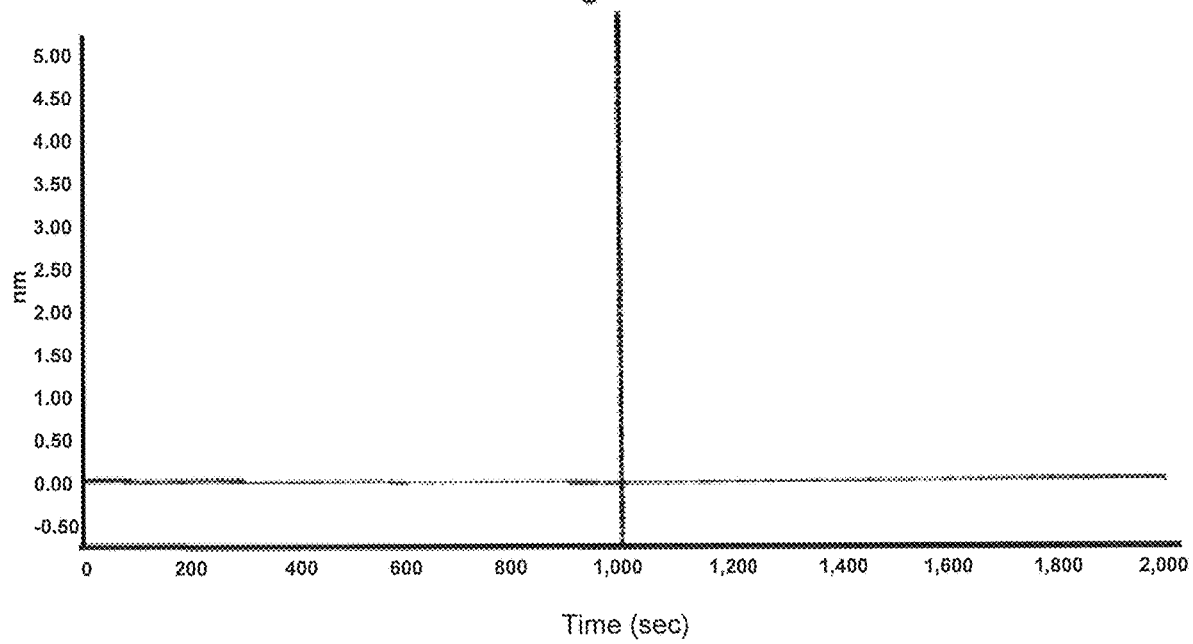
Figure 2C:
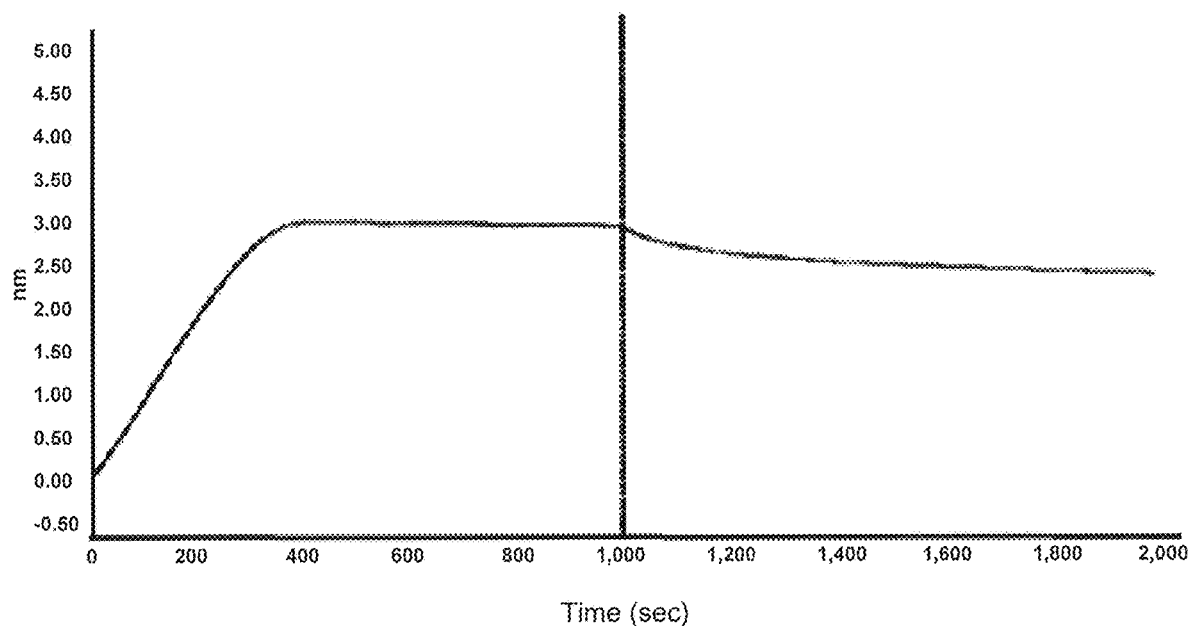
Figure 2C:
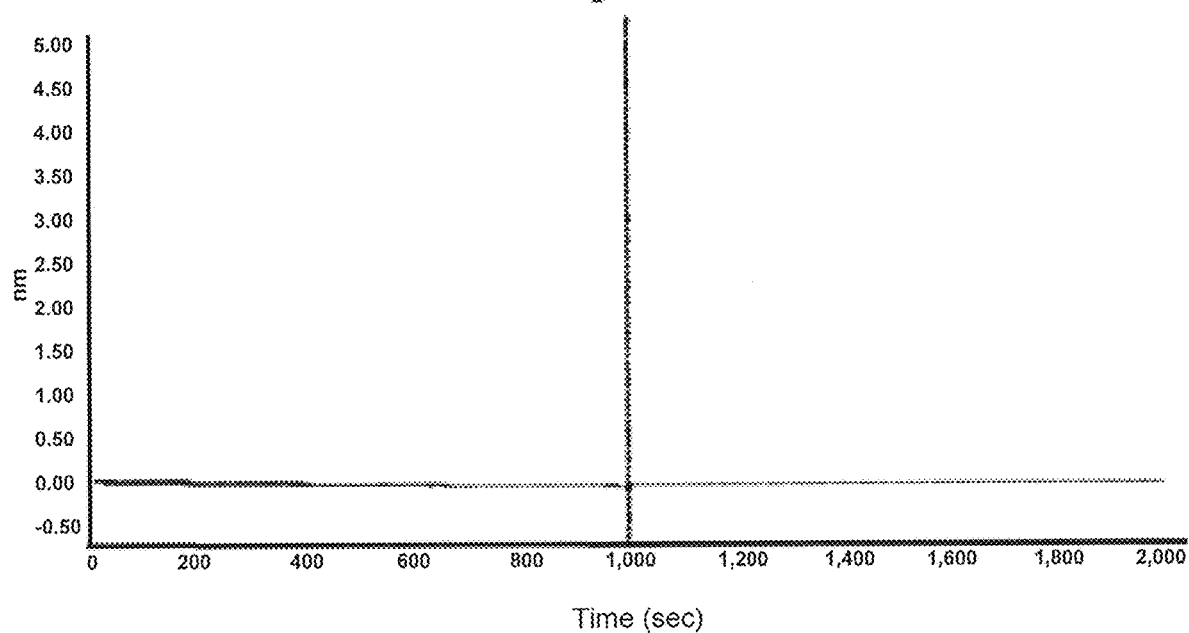
Figure 2C:
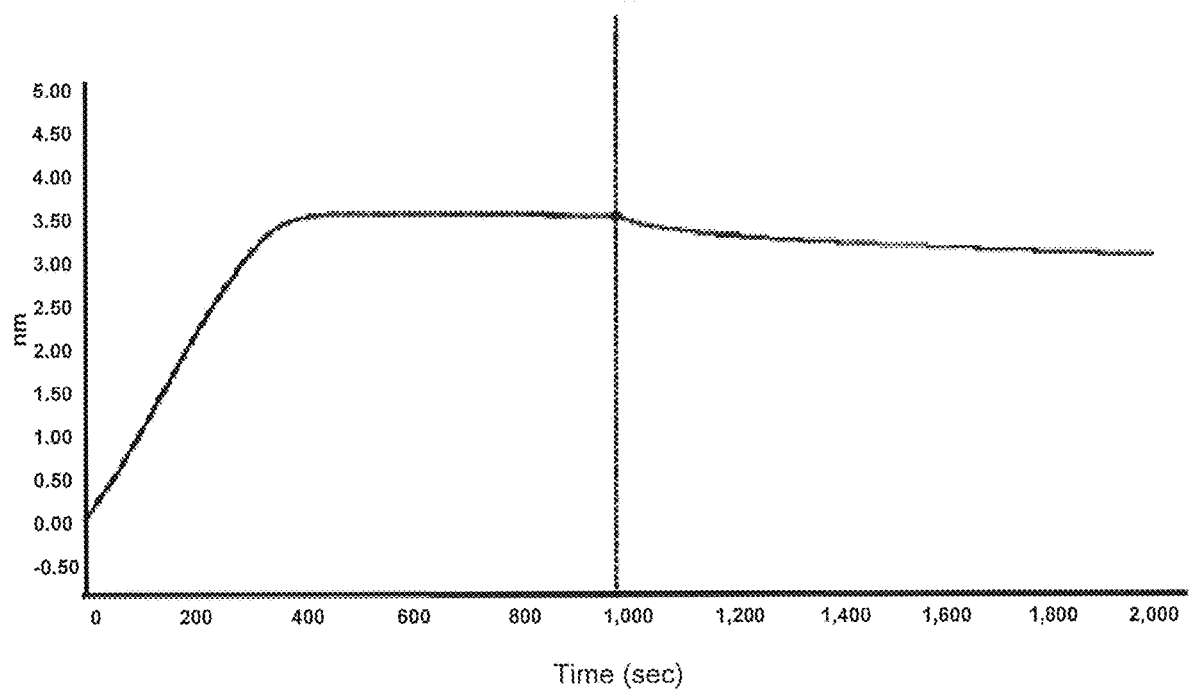

As used herein, the term "alpha-synuclein" is synonymous with "the alpha-synuclein protein" and refers to any of the alpha-synuclein protein isoforms (identified in, for example, UniProt as P37840, 1-3). The amino acid numbering of alpha-synuclein is given with respect to SEQ ID NO:10 as shown below, with methionine (M) being amino acid residue1:

```
SEQ ID NO:10:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

The present invention relates to antibodies and to fragments of antibodies that are capable of specifically binding to alpha-synuclein, and in particular to human alpha-synuclein. In particular, the antibodies and fragments thereof exhibit the ability to specifically bind to an epitope within 112-117 of human alpha-synuclein.

The term "antibody" (Ab) in the context of the present invention refers to an immunoglobulin molecule or according to some embodiments of the invention, a fragment of an immunoglobulin molecule which has the ability to specifically bind to an epitope of a molecule ("antigen"). Naturally occurring antibodies typically comprise a tetramer which is usually composed of at least two heavy (H) chains and at least two light (L) chains. Each heavy chain is comprised of a heavy chain variable domain (abbreviated herein as VH) and a heavy chain constant domain, usually comprised of three domains (CH1, CH2 and CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable domain (abbreviated herein as VL) and a light chain constant domain (CL). Light chains include kappa chains and lambda chains. The heavy and light chain variable domain is typically responsible for antigen recognition, while the heavy and light chain constant domain may mediate the binding of the immunoglobulin to host tissues or factors, including various cells of the immune system (e.g., effector cells) and the first component (C1q) of the classical complement system. The VH and VL regions can be further subdivided into regions of hypervariability, termed "complementarity determining regions," that are interspersed with regions of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable domains of the heavy and light chains contain a binding domain that interacts with an antigen. Of particular relevance are antibodies and their antigen-binding fragments that have been "isolated" so as to exist in a physical milieu distinct from that in which it may occur in nature or that have been modified so as to differ from a naturally occurring antibody in amino acid sequence.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically antigen-binding peptide (in other words, the amino acid residue is within the footprint of the specifically antigen-binding peptide). The term "112-117 epitope" refers to a region of human alpha-synuclein that contains at least 4 of the 6 amino acid residues of 112-117 human alpha-synuclein, which epitope does not include any residue from 1-111 (including any residue from 106-111) of human alpha-synuclein, nor any residue from 118-140 (including residue 118-120) of human alpha-synuclein. As used herein, an antibody is said to be capable of specifically binding to an epitope within the "112-117 epitope" if it is capable of specifically binding to human alpha-synuclein by binding to at least 4 of the 6 amino acid residues of the 112-117 epitope.

As used herein, the term "antigen-binding fragment of an antibody" means a fragment, portion, region or domain of an antibody (regardless of how it is produced (e.g., via cleavage, recombinantly, synthetically, etc.)) that is capable of specifically binding to an epitope, and thus the term "antigen-binding" is intended to mean the same as "epitope-binding" so that, for example, an "antigen-binding fragment of an antibody" is intended to be the same as an "epitope-binding fragment of an antibody". An antigen-binding fragment may contain 1, 2, 3, 4, 5 or all 6 of the CDR Domains of such antibody and, although capable of specifically binding to such epitope, may exhibit a specificity, affinity or selectivity toward such epitope that differs from that of such antibody. Preferably, however, an antigen-binding fragment will contain all 6 of the CDR Domains of such antibody. An antigen-binding fragment of an antibody may be part of, or comprise, a single polypeptide chain (e.g., an scFv), or may be part of, or comprise, two or more polypeptide chains, each having an amino-terminus and a carboxyl terminus (e.g., a diabody, a Fab fragment, a Fab$_2$ fragment, etc.). Fragments of antibodies that exhibit antigen-binding ability can be obtained, for example, by protease cleavage of intact antibodies. More preferably, although the two domains of the Fv fragment, VL and VH, are naturally encoded by separate genes, or polynucleotides that encode such gene sequences (e.g., their encoding cDNA) can be joined, using recombinant methods, by a flexible linker that enables them to be made as a single protein chain in which the VL and VH regions associate to form monovalent antigen-binding molecules (known as single-chain Fv (scFv); see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH regions of a single polypeptide chain to associate together, one can form a bispecific antibody, diabody, or similar molecule (in which two such polypeptide chains associate together to form a bivalent antigen-binding molecule) (see for instance PNAS USA 90(14), 6444-8 (1993) for a description of diabodies). Examples of antigen-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge domain; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i(II):484-90); (vi) camelid or nanobodies (Revets et al; Expert Opin Biol Ther. 2005 January; 5_(I):111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant domain genes. Such antibody fragments are obtained using conventional techniques known to those of skill in the art; suitable fragments capable of binding to a desired epitope may be readily screened for utility in the same manner as an intact antibody.

The term "bispecific antibody" refers to an antibody containing two independent antigen-binding fragments that each target independent targets. These targets can be epitopes present on different proteins or different epitopes present on the same target. Bispecific antibody molecules can be made using compensatory amino acid changes in the constant domains of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time. (Ridgway et al., Protein Engineering 9, 617-621 (1996), Gunasekaran et al., JBC 285, 19637-1(2010), Moore et al., MAbs 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAbs 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities. For example, targeting both a therapeutic target and a transcytosing surface receptor for the purpose of delivering a therapeutic antibody across the blood brain barrier to treat a CNS disease.

The terms GM37, GM-37, GM37 wild type (wt), mab37 and 6004-37 are used interchangeably herein and all refer to the same antibody.

The term antibody GM37 is intended to include an antibody or antigen-binding fragment thereof comprising or consisting of the Heavy Chain as given in CDR1-3 SEQ ID Nos:1-3 and the Light Chain CDR1-3 as given in SEQ ID Nos:4-6. In one embodiment, the antibody GM37 or antigen-binding fragment thereof may comprise or consist of the heavy chain variable domain of SEQ ID NO:7 and/or the light chain variable domain of SEQ ID NO:8. For example, the antibody GM37 may be an IgG antibody comprising a heavy chain consisting of a variable domain of SEQ ID NO:7 and a constant domain of SEQ ID NO:18 together with a light chain consisting of a variable domain of SEQ ID NO:8 and a kappa constant domain of SEQ ID NO:17.

Deamination of proteins, and in these instance antibodies, can occur spontaneously during manufacturing and storage, but also in vivo, and makes the quality of the final pharmaceutical medicament difficult to control. The deamination may also in some instances affect the activity of the molecule. Deamination occurs at asparagine residues, but the location of the relevant asparagine may be difficult to predict with certainty, but may be influenced in some instances by an asparagine-glycine motif. Several possible deamination motifs are found on the GM37 antibody, however, one likely site of deamination was found to be at residue 54 of the heavy chain. The subsequent substitution of asparagine by another amino acid is not straight forward, but 3 variants of GM37 (GM37 variant (var) 1, 2 and 3) were found to retain the activity of the original GM37 (GM37 wild type (wt)).

The term GM37 variants refers to the deaminated variants 1, 2 or 3, wherein variant 1 has a N54S substitution, variant 2 has a N54Q substitution and variant 3 has a N54H compared to the GM37 antibody described herein above.

The antibody GM37 variant (var) 1, 2 and 3 are thus intended to include an antibody or antigen-binding fragment thereof comprising or consisting of the Heavy Chain as given in CDR1 and 3 SEQ ID Nos:1 and 3 from GM 37 and the Light Chain CDR1-3 from GM37 as given in SEQ ID Nos:4-6, but differing in their heavy chain CDR2 so that variant 1 has CDR 2 of SEQ ID NO:33, variant 2 has CDR 2 of SEQ ID NO:34 and variant 3 has CDR 2 of SEQ ID NO:35.

In one embodiment, the antibody GM37 variants or their antigen-binding fragments may comprise or consist of the heavy chain variable domain of SEQ ID NO:30, 31 and 32 for variant 1, 2 and 3, respectively, and the light chain variable domain of SEQ ID NO:8. The antibody GM37 may be an IgG antibody comprising a heavy chain consisting of a variable domain of SEQ ID NO:30, 31 or 32 and a constant domain of SEQ ID NO:18 together with a light chain consisting of a variable domain of SEQ ID NO:8 and a kappa constant domain of SEQ ID NO:17.

The terms GM285, GM-285, mab285 and 6004-285 are used interchangeably herein and all refer to the same antibody.

The term antibody GM285 is intended to include an antibody or antigen-binding fragment thereof comprising or consisting of the Heavy Chain as given in CDR1-3 SEQ ID NOs:20-22 and the Light Chain CDR1-3 as given in SEQ ID NOs:23-25. In one embodiment, the antibody GM37 or antigen-binding fragment thereof may comprise or consist of the heavy chain variable domain of SEQ ID NO:26 and/or the light chain variable domain of SEQ ID NO:27. For example, the antibody GM37 may be an IgG antibody comprising a heavy chain consisting of a variable domain of SEQ ID NO:26 and a constant domain of SEQ ID NO:28 together with a light chain consisting of a variable domain of SEQ ID NO:27 and a kappa constant domain of SEQ ID NO:29.

The GM285 antibody specifically binds an epitope within the sequence 112-115 (ILED; SEQ ID NO:19) of human alpha-synuclein (SEQ ID NO:10).

Unless otherwise specified herein, the numbering of amino acid residues in this region is according to IMGT®, the international ImMunoGeneTics information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and HumanServices. Chothia, C. & Lesk, A. M. (1987). Canonical structures for the hypervariable domains of immunoglobulins. J. Mol. Biol. 196, 901-917).

An "anti-alpha-synuclein antibody" or "alpha-synuclein antibody" (used interchangeably herein, depending on the context wherein its written) is an antibody or an antigen-binding fragment thereof which binds specifically to alpha-synuclein or an alpha-synuclein fragment as defined herein above, in particular the sequence of alpha-synuclein corresponding to SEQ ID NOs 9 and/or 19.

The term "human antibody" (which may be abbreviated to "humAb" or "HuMab"), as used herein, is intended to include antibodies having variable and constant domains derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments a monoclonal antibody can be composed of more than one Fab domain thereby increasing the specificity to more than one target. The terms "monoclonal antibody" or "monoclonal antibody composition" are not intended to be limited by any particular method of production (e.g., recombinant, transgenic, hybridoma, etc.).

The term "humanized" refer to a molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Humanization lessens or eliminates the likelihood that a constant domain of the molecule will act as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant domains, but modifying the variable domains as well so as to reshape them as closely as possible to human form. It is known that the variable domains of both heavy and light chains contain three complementarity—determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Anti-lysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well known (see, e.g., U.S. Pat. Nos. 5,225,539; 5,530,101; 5,585,089; 5,859,205; 6,407,213; 6,881,557).

As used herein, an antibody or an antigen-binding fragment thereof is said to "specifically" bind a region of another molecule (i.e., an epitope) if it reacts or associates more frequently, more rapidly, with greater duration and/or with greater affinity or avidity with that epitope relative to alternative epitopes. In one embodiment, the antibody, or antigen-binding fragment thereof, of the invention binds at least 10-fold more strongly to its target (human alpha synuclein) than to another molecule; preferably at least 50-fold more strongly and more preferably at least 100-fold more strongly. Preferably, the antibody, or antigen-binding fragment thereof, binds under physiological conditions, for example, in vivo. Thus, an antibody that is capable of "specifically binding" to an epitope within residues 112-117 (ILEDMP (SEQ ID NO:9)) of human alpha-synuclein encompasses an antibody or antigen-binding fragments thereof, that is capable of binding to an epitope within residues 112-117 of human alpha-synuclein with such specificity and/or under such conditions. Methods suitable for determining such binding will be known to those skilled in the art, and exemplary methods are described in the accompanying Examples. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in either a BIAcore® 3000 or T200 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold.

The term "kd" (sec −1 or 1/s), as used herein, refers to the dissociation rate constant of a particular antibody-antigen interaction. Said value is also referred to as the koff value.

The term "ka" (M−1×sec−1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M−1 or 1/M), as used herein, refers to the association equilibrium constant of a particular antibody-antigen interaction and is obtained by dividing the ka by the kd.

In one embodiment, the invention relates to an antibody or antigen-binding fragments thereof, which exhibits one or more of the following properties:

i. a binding affinity (KD) for alpha-synuclein of between 0.5-10 nM, such as 1-5 nM or 1-2 nM;
ii. capability of inhibiting protease truncation of alpha-synuclein fibrils;
iii. capability of reversing impairment in basal synaptic transmission in F28-snca transgenic mice;
iv. capability of reducing levels of alpha-synuclein in the mouse hippocampus as measured by in vivo microdialysis;
v. capability, when administered chronically, to restore motor function in a rat model of Parkinson's disease
vi. Capability to prevent seeding of alpha-synuclein (such as accumulation of insoluble phosphorylated alpha-synuclein in vitro and/or in a mouse model of Parkinson's disease); and/or
vii. Capability to bind truncated alpha-synuclein in a human brain.

The binding affinity (KD) for alpha-synuclein may be determined using methods well known in the art, e.g. as described in Example 2.

The term "capability of inhibiting protease truncation of alpha-synuclein fibrils" includes the capability of inhibiting calpain-1 induced formation of fragment 1-119-122 of human alpha synuclein in primary cortical neurons (see Example 5).

The term "capability of reversing impairment in basal synaptic transmission in F28-snca transgenic mice" includes the capability of reverse the impairment of synaptic transmission and plasticity in the CA1 area of the hippocampus in F28-snca transgenic mice, for example as indicated by evoked fEPSP slope as measured electrophysiologically (See Example 6).

The term "capability of reducing levels of alpha-synuclein in the mouse hippocampus as measured by in vivo microdialysis" includes the capability of reducing levels of human alpha synuclein in the hippocampus awake, freely-moving F28-snca transgenic mice, as measured using in vivo microdialysis (see Example 7).

The term "capability, when administered chronically, to restore motor function in a rat model of Parkinson's disease" include the capability to reduce or eliminate motor asymmetry in a rat recombinant adeno-associated viral vector (rAAV) model of Parkinson's Disease (see Example 8).

In some antibodies, only part of a CDR, namely the subset of CDR residues required for binding, termed the SDRs, are needed to retain binding in a humanized antibody. CDR residues not contacting the relevant epitope and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable domains Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

(Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to alpha-synuclein, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | -1 | -2 | -2 | 0 | -1 | -1 | 0 | -2 | -1 | -1 | -1 | -1 | -2 | -1 | +1 | 0 | -3 | -2 | 0 |
| R | -1 | +5 | 0 | -2 | -3 | +1 | 0 | -2 | 0 | -3 | -2 | +2 | -1 | -3 | -2 | -1 | -1 | -3 | -2 | -3 |
| N | -2 | 0 | +6 | +1 | -3 | 0 | 0 | 0 | +1 | -3 | -3 | 0 | -2 | -3 | -2 | +1 | 0 | -4 | -2 | -3 |
| D | -2 | -2 | +1 | +6 | -3 | 0 | +2 | -1 | -1 | -3 | -4 | -1 | -3 | -3 | -1 | 0 | -1 | -4 | -3 | -3 |
| C | 0 | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0 | 0 | -3 | +5 | +2 | -2 | 0 | -3 | -2 | +1 | 0 | -3 | -1 | 0 | -1 | -2 | -1 | -2 |
| E | -1 | 0 | 0 | +2 | -4 | +2 | +5 | -2 | 0 | -3 | -3 | +1 | -2 | -3 | -1 | 0 | -1 | -3 | -2 | -2 |
| G | 0 | -2 | 0 | -1 | -3 | -2 | -2 | +6 | -2 | -4 | -4 | -2 | -3 | -3 | -2 | 0 | -2 | -2 | -3 | -3 |
| H | -2 | 0 | +1 | -1 | -3 | 0 | 0 | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0 | -3 | -2 | -1 | -3 | -1 | +3 |
| L | -1 | -2 | -3 | -4 | -1 | -2 | -3 | -4 | -3 | +2 | +4 | -2 | +2 | 0 | -3 | -2 | -1 | -2 | -1 | +1 |
| K | -1 | +2 | 0 | -1 | -3 | +1 | +1 | -2 | -1 | -3 | -2 | +5 | -1 | -3 | -1 | 0 | -1 | -3 | -2 | -2 |
| M | -1 | -1 | -2 | -3 | -1 | 0 | -2 | -3 | -2 | +1 | +2 | -1 | +5 | 0 | -2 | -1 | -1 | -1 | -1 | +1 |
| F | -2 | -3 | -3 | -3 | -2 | -3 | -3 | -3 | -1 | 0 | 0 | -3 | 0 | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0 | -1 | 0 | 0 | 0 | -1 | -2 | -2 | 0 | -1 | -2 | -1 | +4 | +1 | -3 | -2 | -2 |
| T | 0 | -1 | 0 | -1 | -1 | -1 | -1 | -2 | -2 | -1 | -1 | -1 | -1 | -2 | -1 | +1 | +5 | -2 | -2 | 0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0 | -3 | -3 | -3 | -1 | -2 | -2 | -3 | -3 | +3 | +1 | -2 | +1 | -1 | -2 | -2 | 0 | -3 | -1 | +4 |

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments The invention thus contemplates the use of random mutagenesis to identify improved CDRs. In the context of the present invention, conservative substitutions may be defined by substitutions within the classes of amino acids reflected in one or more of the following three tables:

Amino Acid Residue Classes for Conservative Substitutions:

TABLE 2

| Acidic Residues | Asp (D) and Glu (E) |
|---|---|
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Cly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| 1 | A | S | T |
|---|---|---|---|
| 2 | D | E |   |
| 3 | N | Q |   |
| 4 | R | K |   |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic antigen-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody,*" MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas,*" Int. J. Cancer 10.1002/ijc.25645; Hackel, B. J. et al. (2010) "*Stability And CDR Composition Biases Enrich Binder Functionality Landscapes,*" J. Mol. Biol. 401(1):84-96; Montgomery, D. L. et al. (2009) "*Affinity Maturation And Characterization Of A Human Monoclonal Antibody Against HIV-1 gp41,*" MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth,*" Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions,*" J. Mol. Biol. 388(3):541-558; Bostrom, J. et al. (2009) "*Improving Antibody Binding Affinity And Specificity For Therapeutic Development,*" Methods Mol. Biol. 525: 353-376; Steidl, S. et al. (2008) "*In Vitro Affinity Maturation Of Human GM-CSF Antibodies By Targeted CDR-Diversification,*" Mol. Immunol. 46(1):135-144; and Barderas, R. et al. (2008) "*Affinity Maturation Of Antibodies Assisted By In Silico Modeling,*" Proc. Natl. Acad. Sci. (USA) 105(26): 9029-9034.

Thus, the sequence of CDR variants of encompassed antibodies or their antigen-binding fragments may differ from the sequence of the CDR of the parent antibody, GM37, GM37 var 1-3, or 285, through substitutions; for instance substituted 4 amino acid residue, 3 amino acid residue, 2 amino acid residue or 1 of the amino acid residues. According to an embodiment of the invention it is furthermore envisaged that the amino acids in the CDR regions may be substituted with conservative substitutions, as defined in the 3 tables above.

The term "treatment" or "treating" as used herein means ameliorating, slowing, attenuating or reversing the progress or severity of a disease or disorder, or ameliorating, slowing, attenuating or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody or antigen-binding fragments thereof, of the invention, refers to an amount sufficient, at dosages and for periods of time necessary, to achieve an intended biological effect or a desired therapeutic result including, without limitation, clinical results. The phrase "therapeutically effective amount" when applied to an antibody or antigen-binding fragments thereof, of the invention is intended to denote an amount of the antibody, or antigen-binding fragment thereof, that is sufficient to ameliorate, palliate, stabilize, reverse, slow, attenuate or delay the progression of a disorder or disease state, or of a symptom of the disorder or disease. In an embodiment, the method of the present invention provides for administration of the antibody, or antigen-binding fragment thereof, in combinations with other compounds. In such instances, the "effective amount" is the amount of the combination sufficient to cause the intended biological effect.

A therapeutically effective amount of an anti-alpha-synuclein antibody or antigen-binding fragment thereof of the invention may vary according to factors such as the disease state, age, sex, and weight of the individual, and the ability of the anti-alpha-synuclein antibody to elicit a desired response in the individual. A therapeutically effective amount is also one in which any toxic or detrimental effects of the antibody or antibody portion are outweighed by the therapeutically beneficial effects.

As indicated above, the present invention particularly relates to a monoclonal antibody capable of specifically binding to an epitope within amino acids 112-117 of human alpha-synuclein (SEQ ID NO:9 (ILEDMP)). In one embodiment the antibody is capable of competing with the antibody GM37 for binding to an epitope within the 112-117 amino acids of alpha-synuclein.

The antibodies of the present invention, exemplified by GM37 its variants GM37 var 1-3 and GM285, and their alpha-synuclein binding fragments are capable of binding the toxic alpha-synuclein fragment consisting of residues 1-119/122 of alpha-synuclein and neutralizing its toxicity (for example, by extracellular binding to the alpha-synuclein fragment and thereby preventing it from being taken up by cells. Surprisingly the antibodies of the present invention, which are capable of binding to an epitope within amino acids 112-117 of alpha-synuclein are superior to prior art antibodies such as antibody 9E4 in binding to toxic alpha-synuclein species in human brain, and have superior effects on clearing extracellular alpha-synuclein and normalising an impaired synaptic transmission induced by alpha-synuclein in vivo. The antibodies of the invention are also able to ameliorate the appearance of a relevant motor phenotype in a rat model for Parkinson's disease.

The antibodies of the present invention are preferably human or humanized antibodies.

The present invention also provides a method of reducing alpha-synuclein aggregate formation in a patient, comprising administering to the patient in need of such treatment, a therapeutically effective amount of an antibody of the invention.

Further the antibodies may be in a composition together with a pharmaceutically acceptable carrier, diluent and/or stabilizer. The antibodies of the invention may be used in therapy. In particular, the antibodies of the invention may be used in treating synucleinopathies such as Parkinson's disease (including idiopathic inherited forms of Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy.

The treatment envisioned by the present invention may be chronic and the patient may be treated at least 2 weeks, such as at least for 1 month, 6, months, 1 year or more.

The antibodies of antigen-binding fragments thereof of the present invention may be produced in different cell lines, such as a human cell line, a mammal non-human cell line, and insect cell line, for example a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line (Dumont et al, 2015, Crit Rev Biotechnol. September 18:1-13., the contents which is included herein by reference).

The antibodies of the present invention may for example be monoclonal antibodies produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or non-human mammals such as rats, rabbits, dogs, sheep, goats, primates, etc.

In one embodiment, the antibody of the invention is a human antibody. Human monoclonal antibodies directed against alpha-synuclein may be generated using transgenic or transchromosomal mice carrying parts of the human immune system rather than the mouse system. Such transgenic and transchromosomic mice include mice referred to herein as HuMAb mice and KM mice, respectively.

The HuMAb mouse contains a human immunoglobulin gene minilocus that encodes unrearranged human heavy variable and constant (μ and Y) and light variable and constant (κ) chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or Igκ and in response to immunization, the introduced human heavy and light chain transgenes, undergo class switching and somatic mutation to generate high affinity human IgG, κ monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 811-820 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5[J/K](Balb) as described in WO 09/097006.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain trans-chromosome composed of chromosome 14 antigen-binding fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant domains, kappa or lambda, may be used. If desired, the class of an anti-alpha-synuclein antibody of the present invention may be switched by known methods. For example, an antibody of the present invention that was originally IgM may be class switched to an IgG antibody of the present invention. Further, class switching techniques may be used to convert one IgG subclass to another, for instance from IgGI to IgG2. Thus, the effector function of the antibodies of the present invention may be changed by isotype switching to, e.g., an IgG1, IgG2, IgG3 or IgG4 antibody for various therapeutic uses. In one embodiment an antibody of the present invention is an IgG1 antibody, for instance an IgG1, κ. An antibody is said to be of a particular isotype if its amino acid sequence is most homologous to that isotype, relative to other isotypes.

In one embodiment, the antibody of the invention is a full-length antibody, preferably an IgG antibody, in particular an IgG1, κ antibody. In another embodiment, the antibody of the invention is an antibody fragment or a single-chain antibody.

Antibodies and antigen-binding fragments thereof may e.g. be obtained by antigen-binding fragmentation using conventional techniques, and antigen-binding fragments screened for utility in the same manner as described herein for whole antibodies. For example, F(ab')2 antigen-binding fragments may be generated by treating antibody with pepsin. The resulting F(ab')2 antigen-binding fragment may be treated to reduce disulfide bridges to produce Fab' antigen-binding fragments. Fab antigen-binding fragments may be obtained by treating an IgG antibody with papain; Fab' antigen-binding fragments may be obtained with pepsin digestion of IgG antibody. An F(ab') antigen-binding fragment may also be produced by binding Fab'-described below via a thioether bond or a disulfide bond. A Fab' antigen-binding fragment is an antibody antigen-binding fragment obtained by cutting a disulfide bond of the hinge domain of the F(ab')2. A Fab'-antigen-binding fragment may be obtained by treating an F(ab')2 antigen-binding fragment with a reducing agent, such as dithiothreitol. Antibody antigen-binding fragment may also be generated by expression of nucleic acids encoding such antigen-binding fragments in recombinant cells (see for instance Evans et al., J. Immunol. Meth. 184, 123-38 (1995)). For example, a chimeric gene encoding a portion of an F(ab')2 antigen-binding fragment could include DNA sequences encoding the CH1 region and hinge domain of the H chain, followed by a translational stop codon to yield such a truncated antibody antigen-binding fragment molecule.

In one embodiment, the anti-alpha-synuclein antibody is a monovalent antibody, preferably a monovalent antibody as described in WO2007059782 (which is incorporated herein by reference in its entirety) having a deletion of the hinge domain. Accordingly, in one embodiment, the antibody is a monovalent antibody, wherein said anti-alpha-synuclein antibody is constructed by a method comprising: i) providing a nucleic acid construct encoding the light chain of said monovalent antibody, said construct comprising a nucleotide sequence encoding the VL region of a selected antigen specific anti-alpha-synuclein antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge domain and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-alpha-synuclein antibody is a monovalent antibody, which comprises:

(i) a variable domain of an antibody of the invention as described herein or an antigen-binding part of the said region, and
(ii) a CH domain of an immunoglobulin or a domain thereof comprising the CH2 and CH3 domains, wherein the CH domain or domain thereof has been modified such that the domain corresponding to the hinge domain and, if the immunoglobulin is not an IgG4 subtype, other domains of the CH domain, such as the CH3 domain, do not comprise any amino acid residues, which are capable of forming disulfide bonds with an identical CH domain or other covalent or stable non-covalent inter-heavy chain bonds with an identical CH domain in the presence of polyclonal human IgG.

In a further embodiment, the heavy chain of the monovalent anti-alpha-synuclein antibody has been modified such that the entire hinge domain has been deleted.

In another further embodiment, the sequence of said monovalent antibody has been modified so that it does not comprise any acceptor sites for N-linked glycosylation.

The invention also includes "Bispecific Antibodies," wherein an anti-Alpha-synuclein binding region (e.g., a Alpha-synuclein-binding region of an anti-alpha-synuclein monoclonal antibody) is part of a bivalent or polyvalent bispecific scaffold that targets more than one epitope, (for example a second epitope could comprise an epitope of an active transport receptor, such that the Bispecific Antibody would exhibit improved transcytosis across a biological barrier, such as the Blood Brain Barrier). Thus, in another further embodiment, the monovalent Fab of an anti-synuclein antibody may be joined to an additional Fab or scfv that targets a different protein to generate a bispecific antibody. A bispecific antibody can have a dual function, for example a therapeutic function imparted by an anti-synuclein binding domain and a transport function that can bind to a receptor molecule to enhance transfer cross a biological barrier, such as the blood brain barrier.

Anti-alpha-synuclein antibodies, and antigen-binding fragments thereof, of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-alpha-synuclein antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

The anti-alpha-synuclein antibodies and antigen-binding fragments thereof described herein may be modified by inclusion of any suitable number of modified amino acids and/or associations with such conjugated substituents. Suitability in this context is generally determined by the ability to at least substantially retain the alpha-synuclein selectivity and/or the anti-alpha-synuclein specificity associated with the non-derivatized parent anti-alpha-synuclein antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Anti-alpha-synuclein antibodies may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and U.S. Pat. No. 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies of the present invention may further be used in a diagnostic method or as a diagnostic imaging ligand.

In one embodiment, anti-alpha-synuclein antibodies comprising one or more radiolabeled amino acids are provided. A radiolabeled anti-alpha-synuclein antibody may be used for both diagnostic and therapeutic purposes (conjugation to radiolabeled molecules is another possible feature). Non-limiting examples of such labels include, but are not limited to bismuth ($^{213}$Bi), carbon ($^{11}$C, $^{13}$C, $^{14}$C), chromium ($^{51}$Cr), cobalt ($^{57}$Co, $^{69}$Co), copper ($^{64}$Cu), dysprosium ($^{165}$Dy), erbium ($^{169}$Er), fluorine ($^{18}$F), gadolinium ($^{153}$Gd, $^{159}$Gd), gallium (68Ga, $^{67}$Ga), germanium ($^{68}$Ge), gold ($^{198}$Au), holmium, (166Ho) hydrogen ($^3$H), indium ($^{111}$In, $^{112}$In, $^{113}$In, $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanium ($^{140}$La), lutetium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y) and zinc ($^{65}$Zn). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. Pat. No. RE35,500), U.S. Pat. Nos. 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl-*3*-(Trimethylstannyl)Benzoate As An Intermediate,*" Nucl. Med. Biol.

25(7):659-665; Kurth, M. et al. (1993) "*Site-Specific Conjugation Of A Radioiodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radioiodinated antibody for targeting tumors," Cancer Res. 50(3 Suppl): 857s-861s).

The invention also provides anti-alpha-synuclein antibodies and antigen-binding fragments thereof that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus in one embodiment the anti-alpha-synuclein antibody of the invention may be labelled with a fluorescent label, a chemiluminescent label, a paramagnetic label, a radioisotopic label or an enzyme label. The labelled antibody may be used in detecting or measuring the presence or amount of said alpha-synuclein in the brain of a subject. This method may comprise the detection or measurement of in vivo imaging of anti-alpha-synuclein antibody bound to said alpha-synuclein and may comprises ex vivo imaging of said anti-alpha-synuclein antibody bound to said alpha-synuclein.

In a further aspect, the invention relates to an expression vector encoding one or more polypeptide chains of an antibody of the invention or an antigen-binding fragment thereof. Such expression vectors may be used for recombinant production of the antibodies and antigen-binding fragments of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-alpha-synuclein antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a $CaPO_4$-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of anti-alpha-synuclein antibodies or antigen-binding fragments thereof in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), Grant et al., Methods in Enzymol 153, 516-544 (1987), Mattanovich, D. et al. Methods Mol. Biol. 824, 329-358 (2012), Celik, E. et al. Biotechnol. Adv. 30(5), 1108-1118 (2012), Li, P. et al. Appl. Biochem. Biotechnol. 142(2), 105-124 (2007), Boer, E. et al. Appl. Microbiol. Biotechnol. 77(3), 513-523 (2007), van der Vaart, J. M. Methods Mol. Biol. 178, 359-366 (2002), and Holliger, P. Methods Mol. Biol. 178, 349-357 (2002)).

In an expression vector of the invention, anti-alpha-synuclein antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

The antibodies of antigen-binding fragments thereof of the present invention may be produced in different cell lines, such as a human cell line, a mammal non-human cell line, and insect cell line, for example a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line (Dumont et al, 2015, Crit Rev Biotechnol. September 18:1-13., the contents which is included herein by reference).

In an even further aspect, the invention relates to a recombinant eukaryotic or prokaryotic host cell, such as a transfectoma, which produces an antibody or an antigen-binding domain thereof of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-alpha-synuclein antibody of the present invention or an antigen-binding fragment thereof. In another embodiment, the present invention provides a cell comprising a non-integrated nucleic acid, such as a plasmid, cosmid, phagemid, or linear expression element, which comprises a sequence coding for expression of an anti-alpha-synuclein antibody of the invention.

In a further aspect, the invention relates to a method for producing an anti-alpha-synuclein antibody of the invention, said method comprising the steps of a) culturing a hybridoma or a host cell of the invention as described herein above, and b) purifying the antibody of the invention from the culture media.

In one embodiment, the invention relates to a preparation that, as such term is used herein, comprises an anti-alpha-synuclein antibody as defined herein, and that is substantially free of naturally-arising antibodies that are either not capable of binding to alpha-synuclein or that do not materially alter the anti-alpha-synuclein functionality of the preparation. Thus, such a preparation does not encompass naturally-arising serum, or a purified derivative of such serum, that comprises a mixture of an anti-alpha-synuclein antibody and another antibody that does not alter the functionality of the anti-alpha-synuclein antibody of the preparation; wherein such functionality is selected from the group consisting of:
  (i) a binding affinity (KD) of the anti-alpha-synuclein antibody for alpha-synuclein;
  (ii) a capability of the anti-alpha-synuclein antibody of inhibiting protease truncation of alpha-synuclein fibrils;
  (iii) a capability of the anti-alpha-synuclein antibody of reversing impairment in basal synaptic transmission in F28-snca transgenic mice;
  (iv) a capability of the anti-alpha-synuclein antibody of reducing levels of alpha-synuclein in the mouse hippocampus as measured by in vivo microdialysis; and
  (v) a capability, when administered chronically, of the anti-alpha-synuclein antibody to restore motor function in a rat model of Parkinson's disease.
  (vi) a capability to prevent seeding of alpha-synuclein (such as accumulation of insoluble phosphorylated alpha-synuclein in vitro and/or in a mouse model of Parkinson's disease); and/or
  (vii) a capability to bind truncated alpha-synuclein in a human brain.

The invention particularly relates to preparations of such an anti-alpha-synuclein antibody having a structural change in its amino acid sequence (in any of its CDRs, variable domains, framework residues and/or constant domains) relative to the structure of a naturally-occurring anti-alpha-synuclein antibody, wherein said structural change causes the anti-alpha-synuclein monoclonal antibody to exhibit a markedly altered functionality (i.e., more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality) relative to the functionality exhibited by said naturally-occurring anti-alpha-synuclein antibody; wherein such functionality is:
  (i) a binding affinity (KD) of the anti-alpha-synuclein monoclonal antibody for alpha-synuclein;
  (ii) a capability of the anti-alpha-synuclein monoclonal antibody of inhibiting protease truncation of alpha-synuclein fibrils;
  (iii) a capability of the anti-alpha-synuclein monoclonal antibody of reversing impairment in basal synaptic transmission in F28-snca transgenic mice;
  (iv) a capability of the anti-alpha-synuclein monoclonal antibody of reducing levels of alpha-synuclein in the mouse hippocampus as measured by in vivo microdialysis; and/or
  (v) a capability, when administered chronically, of the anti-alpha-synuclein monoclonal antibody to restore motor function in a rat model of Parkinson's disease;
  (vi) a capability to prevent seeding of alpha-synuclein (such as accumulation of insoluble phosphorylated alpha-synuclein in vitro and/or in a mouse model of Parkinson's disease); and/or
  (vii) a capability to bind truncated alpha-synuclein in a human brain.
especially wherein such altered functionality is a result of the structural change and thus is inseparable from it.

The term "substantially free" of naturally-arising antibodies refers to the complete absence of such naturally-arising antibodies in such preparations, or of the inclusion of a concentration of such naturally-arising antibodies in such preparations that does not materially affect the alpha-synuclein-binding properties of the preparations. An antibody is said to be "isolated" if it has no naturally-arising counterpart or has been separated or purified from components which naturally accompany it.

The term "naturally-arising antibodies," as it relates to such preparations, refers to antibodies (including naturally-arising autoantibodies) elicited within living humans or other animals, as a natural consequence to the functioning of their immune systems.

Thus, the preparations of the present invention do not exclude, and indeed explicitly encompass, such preparations that contain an anti-alpha-synuclein antibody and a deliberately added additional antibody capable of binding to an epitope that is not possessed by alpha-synuclein. Such preparations particularly include embodiments thereof wherein the preparation exhibits enhanced efficacy in treating synucleinopathies such as Parkinson's disease (including idiopathic and inherited form of Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy.

In an even further aspect, the invention relates to a pharmaceutical composition comprising:
(i) an anti-alpha-synuclein antibody or antigen-binding fragment thereof, both as defined herein or a preparation, as such term is defined herein, that comprises such an anti-alpha-synuclein antibody or antigen-binding fragment thereof, and
(ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

Pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on epitope binding.

A pharmaceutical composition of the present invention may also include diluents, fillers, salts, buffers, detergents (e.g., a non-ionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. Additional suitable routes of administering a compound of the present invention in vivo and in vitro are well known in the art and may be selected by those of ordinary skill in the art. In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the anti alpha-synuclein antibodies depend on the disease or condition to be treated and may be determined by the persons skilled in the art. On any given day that a dosage is given, the dosage may range from about 0.0001 to about 100 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight.

A physician having ordinary skill in the art may readily determine and prescribe the effective amount of the pharmaceutical composition required. For example, the physician could start doses of the anti-alpha-synuclein antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

Labelled antibodies of the invention can be used for diagnostic purposes to detect, diagnose, or monitor diseases or disorders. The invention provides for the detection or diagnosis of a neurodegenerative or cognitive disease or disorder, including but not limited to Parkinson's disease, idiopathic Parkinson's disease, familiar Parkinson's Disease, Diffuse Lewy Body Disease (DLBD), Lewy body variant of Alzheimer's disease (LBV), Combined Alzheimer's and Parkinson's disease, pure autonomic failure or multiple system atrophy, comprising: (a) assaying the existence of alpha-synuclein species and fragments in cells or tissue samples of a subject using one or more antibodies that specifically bind to alpha-synuclein; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

Antibodies of the invention can be used to assay alpha-synuclein monomer, oligomers, fibrillary forms or fragments of alpha-synuclein in a biological sample using immunohistochemical methods well-known in the art. Other antibody-based methods useful for detecting protein include immunoassays such as the enzyme linked immunoassay (ELISA), radioimmunoassay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}$I, $^{131}$I), carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as fluorescein and rhodamine.

The presence of labeled anti-alpha-synuclein antibodies or their alpha-synuclein-binding fragments may be detected in vivo for diagnosis purposes. In one embodiment, diagnosis comprises: a) administering to a subject an effective amount of such labeled molecule; b) waiting for a time interval following administration to allow the labeled molecule to concentrate at sites (if any) of Aβ deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention relates to an antibody or antigen-binding fragments thereof, of the invention, for use in medicine.

In a further aspect, the invention relates to an antibody or antigen-binding fragments thereof, of the invention, for use in treating, diagnosing or imaging a synucleinopathy.

In one embodiment, the monoclonal antibody, or antigen-binding fragment thereof, is for use in treating Parkinson's disease, idiopathic Parkinson's disease, familiar forms of Parkinson's Disease, Diffuse Lewy Body Disease (DLBD), Lewy body variant of Alzheimer's disease (LBV), Combined Alzheimer's and Parkinson's disease, pure autonomic failure or multiple system atrophy.

In a further aspect, the invention relates to the use of the antibody, or antigen-binding fragment thereof, of the invention, in the manufacture of a medicament for treating, diagnosing or imaging a synucleinopathy.

In a further aspect, the invention relates to a treating, diagnosing or imaging Parkinson's disease or other synucleinopathies, comprising administering an effective dosage of an antibody of the invention, or an antigen-binding fragment thereof.

Preferably, in the uses and methods of those aspects of the invention, the treatment is chronic, and is preferably for at least 2 weeks, such as at least for 1 month, 6, months, 1 year or more.

In a further aspect, the invention provides a kit comprising the antibody, or antigen-binding fragment thereof, of the invention.

| | |
|---|---|
| SEQ ID NO: 1 | GM37 CDR 1 Heavy Chain |
| SEQ ID NO: 2 | GM37 CDR 2 Heavy Chain |
| SEQ ID NO: 3 | GM37 CDR 3 Heavy Chain |
| SEQ ID NO: 4 | GM37 CDR 1 Light Chain |
| SEQ ID NO: 5 | GM37 CDR 2 Light Chain |
| SEQ ID NO: 6 | GM37 CDR 3 Light Chain |
| SEQ ID NO: 7 | GM37 Heavy Chain Variable Domain |
| SEQ ID NO: 8 | GM37 Light Chain Variable Domain |
| SEQ ID NO: 9 | Epitope 112-117 of Human Alpha-Synuclein |
| SEQ ID NO: 10 | Human Alpha-Synuclein |
| SEQ ID NO: 11 | A-Syn-AAKK-BAP |
| SEQ ID NO: 12 | A-Syn-BAAK-BAP |
| SEQ ID NO: 13 | A-Syn-BBAA-BAP |
| SEQ ID NO: 14 | A-Syn-BBKK-BAP |
| SEQ ID NO: 15 | A-Syn-120-140_Del-BAP |
| SEQ ID NO: 16 | Residues 1-119 of Human Alpha-Synuclein |
| SEQ ID NO: 17 | Kappa Light Chain Constant domain |
| SEQ ID NO: 18 | IgG1 Heavy Chain Constant domain |
| SEQ ID NO: 19 | GM285 Epitope 112-115 |
| SEQ ID NO: 20 | GM285 CDR 1 Heavy Chain |
| SEQ ID NO: 21 | GM285 CDR 2 Heavy Chain |
| SEQ ID NO: 22 | GM285 CDR 3 Heavy Chain |
| SEQ ID NO: 23 | GM285 CDR 1 Light Chain |
| SEQ ID NO: 24 | GM285 CDR 2 Light Chain |
| SEQ ID NO: 25 | GM285 CDR 3 Light Chain |
| SEQ ID NO: 26 | GM285 Heavy Chain Variable Domain |
| SEQ ID NO: 27 | GM285 Light Chain Variable Domain |
| SEQ ID NO: 28 | GM285 IgG1 Heavy Chain Constant domain |
| SEQ ID NO: 29 | GM285 Kappa Light Chain Constant domain |
| SEQ ID NO: 30 | GM37 Variant 1 Heavy Chain Variable Domain |
| SEQ ID NO: 31 | GM37 Variant 2 Heavy Chain Variable Domain |
| SEQ ID NO: 32 | GM37 Variant 3 Heavy Chain Variable Domain |
| SEQ ID NO: 33 | GM37 Variant 1 Heavy Chain CDR 2 |
| SEQ ID NO: 34 | GM37 Variant 2 Heavy Chain CDR 2 |
| SEQ ID NO: 35 | GM37 Variant 3 Heavy Chain CDR 2 |
| SEQ ID NO: 36 | 9E4 Binding Epitope |
| SEQ ID NO: 37 | Human Beta-Synuclein |
| SEQ ID NO: 38 | Human Gamma-Synuclein |
| SEQ ID NO: 39 | Alpha-Synuclein Ortholog for Cynomolgus Monkey |
| SEQ ID NO: 40 | Alpha-Synuclein Ortholog for Rat |
| SEQ ID NO: 41 | Alpha-Synuclein Ortholog for Mouse |
| SEQ ID NO: 42 | 9E4 HC |
| SEQ ID NO: 43 | 9E4 LC |

Embodiments of the Invention

As would be apparent from the text and the Examples the invention further relates to the below embodiments 1. A monoclonal antibody, or antigen-binding fragment thereof capable of specifically binding to an epitope within amino acids 112-117 on alpha-synuclein (SEQ ID NO:9 (ILEDMP)).
2. The monoclonal antibody, or antigen-binding fragment thereof, according to Embodiment 1 which competes with the antibody GM37 for binding to said epitope.
3. The monoclonal antibody, or antigen-binding fragment thereof, according to Embodiment 1, which is GM37, GM37 variant 1, GM37 variant 2 or GM37 variant 3.
4. A monoclonal antibody, or antigen-binding fragment thereof capable of specifically binding to an epitope within amino acids 112-115 on alpha-synuclein (SEQ ID NO:19 (ILED)).

5. The monoclonal antibody, or antigen-binding fragment thereof, according to Embodiment 1 or 4, which is GM285.
6. The monoclonal antibody, or antigen-binding fragment thereof, according to the previous Embodiments, wherein the antibody comprises or consists of an intact antibody.
7. The monoclonal antibody, or antigen-binding fragment thereof, according to any one of the preceding Embodiments comprising or consisting of an antigen-binding fragment selected from the group consisting of Fv fragments (e.g. single chain Fv and disulphide-bonded Fv), Fab-like fragments (e.g. Fab fragments, Fab' fragments and F(ab)₂ fragments) and domain antibodies (e.g. single VH variable domains or VL variable domains).
8. The monoclonal antibody, or antigen-binding fragment thereof, according to any one of the preceding Embodiments wherein the monoclonal antibody is selected from the group consisting of antibodies of subtype IgG1, IgG2, IgG3 and IgG4.
9. The monoclonal antibody, or antigen-binding fragment thereof, according to any one of the preceding Embodiments wherein the antibody or antigen-binding fragment exhibits one or more of the following properties:
   (i) a binding affinity ($K_D$) for alpha-synuclein between 0.5-10 nM, such as 1-5 nM or 1-2 nM;
   (ii) capability of inhibiting protease truncation of alpha-synuclein fibrils;
   (iii) capability of reversing impairment in basal synaptic transmission in F28-snca transgenic mice;
   (iv) capability of reducing levels of alpha-synuclein in the mouse hippocampus as measured by in vivo microdialysis;
   (v) capability, when administered chronically, to restore motor function in a rat model of Parkinson's disease;
   (vi) Capability to prevent seeding of alpha-synuclein (such as accumulation of insoluble phosphorylated alphasynuclein in vitro and/or in a mouse model of Parkinson's disease); and/or
   (vii) Capability to bind truncated alpha-synuclein in a human brain.
10. The monoclonal antibody, or antigen-binding fragment thereof, according to any one of the preceding Embodiments that is human or humanized.
11. A monoclonal antibody or the monoclonal antibody according to Embodiments 1-3 and 6-10, or antigen-binding fragment thereof, comprising a heavy chain variable domain comprising the following CDRs:
   a) GFTFSSYAMT (SEQ ID NO:1) or an amino acid sequence having no more than 4 amino acid differences, or no more than 3 amino acid differences, or no more than 2 amino acid differences, or no more than 1 amino acid difference;
   b) AIRS(N/S/Q/H) GDRTD YADSVKG (SEQ ID Nos:2, 33, 34, 35) or an amino acid sequence having no more than 4 amino acid differences, or no more than 3 amino acid differences, or no more than 2 amino acid differences, or no more than 1 amino acid difference; or
   c) AKNWAPFDS (SEQ ID NO:3) or an amino acid sequence having with no more than 4 amino acid differences, or no more than 3 amino acid differences, or no more than 2 amino acid differences, or no more than 1 amino acid difference.
12. The monoclonal antibody or antigen-binding fragment thereof according to Embodiment 11 comprising a heavy chain variable domain comprising the CDRs of SEQ ID NOs:1 and 3 and one of SEQ ID NOs:2 and 33, 34 or 35.
13. The monoclonal antibody or antigen-binding fragment thereof according to Embodiment 11 comprising or consisting of a heavy chain variable domain selected from the group consisting of:

a)
```
                                        (SEQ ID NO: 7)
EVQLLESGGG LVQTGGSLRL SCAASGFTFS SYAMTWVRQA

PGKGLEWVSA IRSNGDRTDY ADSVKGRFTI SRDNSQNTLY

LQMNSLRAED TAVYYCAKNW APFDSWGQGT LVTVSS,
``` b)
```
                                       (SEQ ID NO: 30)
EVQLLESGGG LVQTGGSLRL SCAASGFTFS SYAMTWVRQA

PGKGLEWVSA IRSSGDRTDY ADSVKGRFTI SRDNSQNTLY

LQMNSLRAED TAVYYCAKNW APFDSWGQGT LVTVSS,
``` c)
```
                                       (SEQ ID NO: 31)
EVQLLESGGG LVQTGGSLRL SCAASGFTFS SYAMTWVRQA

PGKGLEWVSA IRSQGDRTDY ADSVKGRFTI SRDNSQNTLY

LQMNSLRAED TAVYYCAKNW APFDSWGQGT LVTVSS,
or
``` d)
```
                                       (SEQ ID NO: 32)
EVQLLESGGG LVQTGGSLRL SCAASGFTFS SYAMTWVRQA

PGKGLEWVSA IRSHGDRTDY ADSVKGRFTI SRDNSQNTLY

LQMNSLRAED TAVYYCAKNW APFDSWGQGT LVTVSS.
```

14. A monoclonal antibody or the monoclonal antibody according to Embodiments 1-3 and 6-13, or antigen-binding fragment thereof, comprising a light chain variable domain comprising the following CDRs:
   a) ASQSVSSSYLA (SEQ ID NO:4) or an amino acid sequence having no more than 4 amino acid differences, or no more than 3 amino acid differences, or no more than 2 amino acid differences, or no more than 1 amino acid difference;
   b) GASSRAT (SEQ ID NO:5) or an amino acid sequence having no more than 4 amino acid differences, or no more than 3 amino acid differences, or no more than 2 amino acid differences, or no more than 1 amino acid difference; or
   c) QQYGSSPWT (SEQ ID NO:6) or an amino acid sequence having no more than 4 amino acid differences, or no more than 3 amino acid differences, or no more than 2 amino acid differences, or no more than 1 amino acid difference.
15. The monoclonal antibody or antigen-binding fragment thereof according to Embodiment 14 comprising a light chain variable domain comprising the CDRs of SEQ ID NOs:4, 5 and 6.
16. The antibody or antigen-binding fragment thereof according to Embodiment 14 comprising a light chain variable domain comprising or consisting of the amino acid sequence:

```
                                        (SEQ ID NO: 8)
EIVLTQSPGT LSLSPGERAT LSCRASQSVS SSYLAWYQQK

PGQAPRLLIY GASSRATGIP DRFSGSGSGT DFTLTISRLE

PEDFAVYYCQ QYGSSPWTFG QGTKVEIK.
```

17. The monoclonal antibody or antigen-binding fragment thereof according to Embodiment 14 comprising a light chain comprising or consisting of the amino acid sequence:

```
                                        (SEQ ID NO: 8)
EIVLTQSPGT LSLSPGERAT LSCRASQSVS SSYLAWYQQK

PGQAPRLLIY GASSRATGIP DRFSGSGSGT DFTLTISRLE

PEDFAVYYCQ QYGSSPWTFG QGTKVEIK.
```

18. The monoclonal antibody or antigen-binding fragment thereof according Embodiments 1-3 and 6-17 comprising a light chain variable domain comprising or consisting of the amino acid sequence of SEQ ID NO:8 and heavy a chain variable domain comprising or consisting of the amino acids given in either SEQ ID No:7, 33, 34 or 35.

Figure 27:
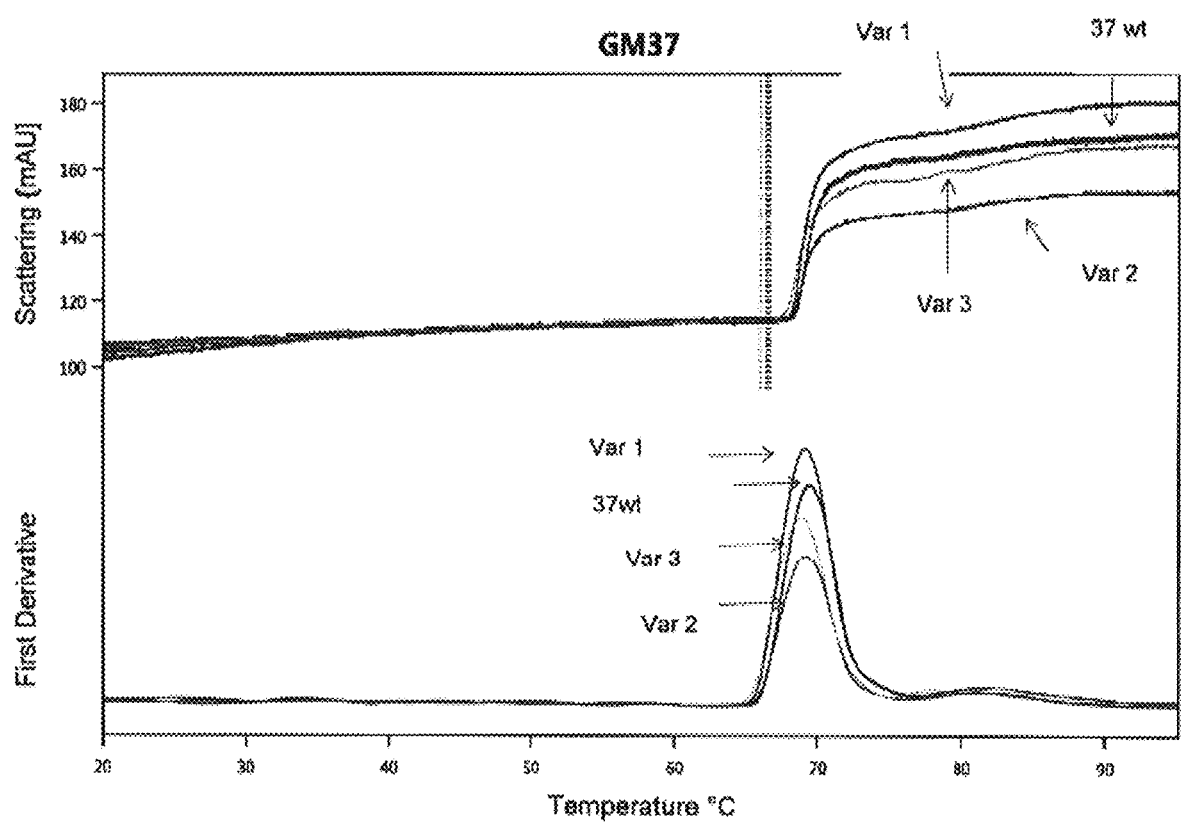
FIG. 27 compares temperature dependent aggregation of wt GM37, var1, var2 and vara. A sample of each of the antibodies was subjected to a steady increase in temperature over time and the level of aggregation was simultaneously measured by multi-angle light scattering (Prometheus NT.48, NanoTemper Technologies). The temperature for onset of aggregation is similar for GM37 and GM37-variants, however the lowest level of aggregation observed for GM37-Var2.

19. The monoclonal antibody or antigen-binding fragment thereof according to Embodiments 1-3 and 6-18 comprising a light chain comprising or consisting of the amino acid sequence of SEQ ID NO:8 and heavy a chain variable domain comprising or consisting of the amino acids given in SEQ ID NO:34 having an increased thermal stability, such as an increased stability to prevent aggregate and unfold as shown in FIG. 27, being between 2%-10% more stable at temperatures above 65° C. compared to GM37 wt, 2%-8% more stable at temperatures above 65° C. compared to GM37 wt or 2%-5% more stable at temperatures above 65° C. compared to GM37 wt.

20. A monoclonal antibody or the monoclonal antibody according to Embodiments 1-10, or antigen-binding fragment thereof, comprising a heavy chain variable domain comprising the following CDRs:
    a) AASGFTFSRFTMT (SEQ ID NO:20) or an amino acid sequence having no more than 4 amino acid differences, or no more than 3 amino acid differences, or no more than 2 amino acid differences, or no more than 1 amino acid difference;
    b) AISGSGGGTS YADSVKG (SEQ ID NO:21) or an amino acid sequence having no more than 4 amino acid differences, or no more than 3 amino acid differences, or no more than 2 amino acid differences, or no more than 1 amino acid difference; or
    c) AKNWAPFDY (SEQ ID NO:22) or an amino acid sequence having with no more than 4 amino acid differences, or no more than 3 amino acid differences, or no more than 2 amino acid differences, or no more than 1 amino acid difference.

21. The monoclonal antibody or antigen-binding fragment thereof according to Embodiment 20 comprising a heavy chain variable domain comprising the CDRs of SEQ ID NOs:20, 21 and 22.

22. The monoclonal antibody or antigen-binding fragment thereof according to Embodiment 20 comprising a heavy chain variable domain comprising or consisting of the amino acid sequence

```
                                        (SEQ ID NO: 26)
EVQLLESGGG LVQPGGSLRL SCAASGFTFS RFTMTWVRQA

PGKGLEWVSA ISGSGGGTSY ADSVKGRLTV SRDNSKNTLY

LQMNSLRAED TAVYYCAKNW APFDYWGQGT LVTVSS.
```

23. A monoclonal antibody or the monoclonal antibody according to any one of Embodiments 1-10 and 20-22, or antigen-binding fragment thereof, comprising a light chain variable domain comprising the following CDRs:
    d) RASQSVSRSYLA (SEQ ID NO:23) or an amino acid sequence having no more than 4 amino acid differences, or no more than 3 amino acid differences, or no more than 2 amino acid differences, or no more than 1 amino acid difference;
    e) GASSRAT (SEQ ID NO:24) or an amino acid sequence having no more than 4 amino acid differences, or no more than 3 amino acid differences, or no more than 2 amino acid differences, or no more than 1 amino acid difference; or
    f) QQYGSSPWT (SEQ ID NO:25) or an amino acid sequence having no more than 4 amino acid differences, or no more than 3 amino acid differences, or no more than 2 amino acid differences, or no more than 1 amino acid difference.

24. The monoclonal antibody or antigen-binding fragment thereof according to Embodiment 23 comprising a light chain variable domain comprising the CDRs of SEQ ID NOs:23, 24 and 25.

25. The antibody or antigen-binding fragment thereof according to Embodiment 24 comprising a light chain variable domain comprising or consisting of the amino acid sequence of:

```
                                        (SEQ ID NO: 27)
EIVLTQSPGT LSLSPGERAT LSCRASQSVS RSYLAWYQQK

PGQAPRLLIY GASSRATGIP DRFSGSGSGT DFTLTVSRLE

PEDFAVYYCQ QYGSSPWTFG QGTKVEIK.
```

26. The monoclonal antibody or antigen-binding fragment thereof according to any one of the preceding Embodiments comprising a light chain variable domain comprising or consisting of the amino acid sequence of SEQ ID NO:27 and heavy a chain variable domain comprising or consisting of the amino acids given in either SEQ ID NO:26.

27. The monoclonal antibody or antigen-binding fragment thereof according to any one of the preceding Embodiment comprising an Fc region.

28. The monoclonal antibody or antigen-binding fragment thereof according to any one of the preceding Embodiment further comprising a moiety for increasing the in vivo half-life of the agent.

29. The monoclonal antibody or antigen-binding fragment thereof according to Embodiment 28 wherein the moiety for increasing the in vivo half-life is selected from the group consisting of polyethylene glycol (PEG), human serum albumin, glycosylation groups, fatty acids and dextran.

30. The monoclonal antibody or antigen-binding fragment thereof according to any one of the preceding Embodiments wherein the antibody polypeptide further comprises a detectable moiety.

31. The monoclonal antibody or antigen-binding fragment thereof according to Embodiment 30 wherein the detectable moiety is a fluorescent label, a chemiluminescent label, a paramagnetic label, a radioisotopic label or an enzyme label.

32. The monoclonal antibody or antigen-binding fragment thereof according to Embodiment 30 or 31 wherein the detectable moiety comprises or consists of a radioisotope.

33. The monoclonal antibody or antigen-binding fragment thereof according to Embodiment 32 wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$Tl.

34. The monoclonal antibody or antigen-binding fragment thereof according to Embodiment 30 wherein the detectable moiety comprises or consists of a paramagnetic isotope.

35. The monoclonal antibody or antigen-binding fragment thereof according to Embodiment 34 wherein the paramagnetic isotope is selected from the group consisting of $^{157}$Gd, $^{55}$Mn, $^{162}$Dy, $^{52}$Cr and $^{56}$Fe.

36. The monoclonal antibody or antigen-binding fragment thereof according to any of Embodiments 30 to 35 wherein the detectable moiety is detectable by an imaging technique such as SPECT, PET, MRI, optical or ultrasound imaging.

37. The monoclonal antibody or antigen-binding fragment thereof according to any of Embodiments 30 to 36 wherein the detectable moiety is joined to the antibody or antigen-binding fragment thereof indirectly, via a linking moiety.

38. The monoclonal antibody or antigen-binding fragment thereof according to Embodiment 37 wherein the linking moiety is selected from the group consisting of derivatives of 1,4,7,10-tetraazacyclododecane-1,4,7,10, tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA).

39. An isolated nucleic acid molecule encoding an antibody or antigen-binding fragment thereof according to any one of the preceding Embodiments or a component polypeptide chain thereof.

40. A nucleic acid molecule according to Embodiment 39 wherein the molecule is a cDNA molecule.

41. A nucleic acid molecule according to Embodiment 30 or 31 encoding an antibody heavy chain or variable domain thereof.

42. A nucleic acid molecule according to any one of Embodiments 39 to 41 encoding an antibody light chain or variable domain thereof.

43. A vector comprising a nucleic acid molecule according to any one of Embodiments 39 to 42.

44. A recombinant host cell comprising a nucleic acid molecule according to any one of Embodiments 39 to 42 or a vector according to Embodiment 43.

45. A method for producing an antibody or antigen-binding fragment according to any one of the Embodiments 1 to 27, the method comprising culturing a host cell as defined in Embodiment 44 under conditions which permit expression of the encoded antibody or antigen-binding fragment thereof.

46. A pharmaceutical composition comprising the monoclonal antibody or antigen-binding fragment according to any one of Embodiments 1 to 35 and a pharmaceutical acceptable carrier.

47. The monoclonal antibody or antigen-binding fragment thereof of Embodiments 1-35 for use in medicine.

48. The monoclonal antibody or antigen-binding fragment thereof of Embodiments 1-35 for use in treating, diagnosing or imaging a synucleinopathy.

49. The monoclonal antibody or antigen-binding fragment thereof according to Embodiment 48 for use in treating Parkinson's disease (including idiopathic and inherited forms of Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy.

50. Use of a monoclonal antibody or antigen-binding fragment thereof of Embodiments 1-35 in the manufacturing of a medicament for treating, diagnosing or imaging a synucleinopathy.

51. The use of a monoclonal antibody or antigen-binding fragment thereof according to Embodiment 50 in the manufacturing of a medicament for treating Parkinson's disease (including idiopathic and inherited forms of Parkinson's disease Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy.

52. A method of treating, diagnosing or imaging a synucleinopathy in a subject, said method comprising administering the pharmaceutical composition of Embodiment 46 to said subject in an effective amount.

53. The antibody, or antigen-binding fragment thereof, for use according to Embodiment 48, or the use according to Embodiment 50, or the method according to Embodiment 52 for treating Parkinson's disease (including idiopathic and inherited forms of Parkinson's disease Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy.

54. The antibody, or antigen-binding fragment thereof, for use; or the use; or the method according to Embodiment 52 or 53, wherein the treatment is chronic 55. The antibody, or antigen-binding fragment thereof, for use; or the use; or the method according to Embodiment 52, wherein the chronic treatment is for at least 2 weeks, such as at least for 1 month, 6, months, 1 year or more.

56. The antibody, or antigen-binding fragment thereof, for use; or the use; or the method according to any one of Embodiments 47 to 55, wherein the subject is human.

57. A kit comprising the antibody or antigen-binding fragment thereof according to Embodiments 1-35

58. The kit according to Embodiment 57 for use in medicine

59. The monoclonal antibody or antigen-binding fragment thereof of Embodiments 30-35 for use in detecting or measuring the presence or amount of said alpha-synuclein in the brain or a body fluid of a subject.

60. The monoclonal antibody or antigen-binding fragment thereof of Embodiments 59, wherein said detection or measurement comprises in vivo imaging of said anti-synuclein antibody bound to said alpha-synuclein.

61. The monoclonal antibody or antigen-binding fragment thereof of Embodiments 30-35 wherein said detection or measurement comprises ex vivo imaging of said anti-synuclein antibody bound to said alpha-synuclein.

EXAMPLES

Example 1: Antibody Screening

1. Immunogen and Ligand Production

The following proteins were acquired or produced for use as immunogens shown in FIG. 1. The mice were immunized with three immunogens: full length recombinant human alpha-synuclein fibrils; human alpha-synuclein recombinant protein containing amino acids 1-60 (Rpeptide, Bogart, Ga.) and human alpha-synuclein recombinant protein containing amino acids 1-119. To make the fibrils from the full length the alpha-synuclein a lyophilized product from Rpeptide, Bogart, Ga. (Catalog number S-1001-2) was used. This was dissolved in 20 mM tris and 300 mM NaCl buffer at concentration of 1 mg/ml protein. To make the fibrils the protein solution was incubated 170 µl aliquots in 96 well plate with a 70 µm diameter ceramic bead in each well at 200 rpm in Vortemp 56 shaker incubator (Labnet International, Edison, N.J., USA), at 37° C. for 7 days, and the formation of fibrils was followed by adding thioflavin T and measuring fluorescence in one of the wells. The recombinant alpha-synuclein containing amino acids 1-60 was dissolved in water to give a concentration of 1 mg/ml.

The recombinant alpha-synuclein containing amino acids 1-119 was made using the following construct: A synthetic gene coding for a 6 amino acid Histidine tag, followed by factor Xa cleavage site and sequence coding for human alpha-synuclein amino acids 1-119:

(SEQ ID NO: 16)
MAHHHHHHIE GRMDVFMKGL SKAKEGVVAA AEKTKQGVAE

AAGKTKEGVL YVGSKTKEGV VHGVATVAEK TKEQVTNVGG

AVVTGVTAVA QKTVEGAGSI AAATGFVKKD QLGKNEEGAP

QEGILEDMPV D was synthezised by Genscript and cloned into NdeI-XhoI site in pET24a(+) expression vector (Novagen).

The expression vector was transformed into *E. coli* BL21 and a single colony picked for expression using the overnight express autoinduction system from Novagen (User protocol TB383 rev. H1005). The scale was 500 ml of final culture volume. Cells were harvested by centrifugation 10 min at 6000 g and subsequently lyzed using BugBuster protein extraction Reagent (User protocol TB245 Rev. 0304). After lysis the sample was cleared by centrifugation and the supernatant used for further purification.

The His-tagged protein was purified on a 5 ml HisTrap column (GE healthcare) equilibrated in 20 mM Sodium phosphate pH7.5, 1 M NaCl (A-buffer). After sample application and wash using A-buffer the protein was eluted in a gradient to 0.25 M Imidazole in A-buffer over 20 column volumes. Fractions of 5 ml were collected and analyzed by SDS-PAGE. Fractions with the protein of interest was pooled, concentrated and applied to an S200 (26/60) size exclusion column (GE healthcare) in 10 mM tris pH 7.4, 300 mM NaCl. Again fractions were pooled according to presence in SDS-PAGE of a band with expected size.

To remove the N-terminal tag, the purified his-tagged alpha-synuclein 1-119 was incubated with factor Xa in a 1:50 ration using the Novagen kit (69037-3FRX). After overnight incubation, the factor Xa was removed batchwise using Xarrest agarose. The cleaved alpha-synuclein 1-119 was finally purified by permissive HisTrap chromatography as described above. From the flow through the purified alpha-synuclein 1-119 was obtained and concentrated to ~400 µg/ml using centricon concentration devises.

Alpha-synuclein (Rpeptide) was rehydrated in PBS at 2 mg/ml and peroxynitirite (100 µL/mg protein) was added dropwise while mixing. The nitrosylated alpha-synuclein was then dialyzed in 5 L PBS and stored at −20° C.

Dopamine was used to oxidize alpha-synuclein. Equal volumes of a 200 uM solution of Dopamine-HCL (Sigma P5244) prepared in 10 mM PBS, pH7.4 and a 28 µM solution of alpha-synuclein (Rpeptide) in 10 mM PBS, pH7.4 were combined. The resulting 14 uM alpha-synuclein/100 uM Dopamine were incubated at 37° C. O/N (over night). The oxidized alpha-synuclein was then dialyzed in PBS and stored at −20° C.

Different native and chimeric versions of synuclein proteins were produced in order to screen a diverse library of anti-alpha-synuclein antibodies. Screening constructs included the following: human, mouse, rat and cynomolgus monkey alpha-synuclein, human Beta-synuclein, Human Gamma-synuclein (FIGS. 21 and 22) and lastly an alpha-synuclein derivative that lacked residues 120-140 of alpha-synuclein. In addition, a series of 4 shuffle constructs: A-Syn-AAKK-BAP, A-Syn-BAAK-BAP, A-Syn-BBAA-BAP, A-Syn-BBKK-BAP (SEQ ID Nos:11-14) were produced. These constructs contained linear stretches of human alpha-synuclein (A), human Beta-synuclein (B) and chicken alpha-synuclein (K). Gene were cloned containing a Biotin Acceptor Peptide (BAP) tag fused to the C-terminus of the ligands in order to facilitate site specific biotinylation of each of the ligands. The bioytinylation allowed for attachment of the ligands to beads used in the soluble ELISA format. Mammalian expression vectors were constructed carrying the different alpha-synuclein BAP tag fusion constructs (ASynBAP). The ligands were expressed in HEK 293 cells using transient transfection (Genmab A/S).

2. Immunization

Antibodies HuMab-Synuclein were derived from the immunizations of HuMAb mouse strain HCo17-BALB/c and HCo12-BALB/c mice, double knock out for the mouse immunoglobulin (Ig) heavy and mouse kappa light chain, which prevents the expression of antibodies that are completely murine (human monoclonal antibody; Medarex Inc., San Jose, Calif., USA). The various mouse strains were made transgenic by the insertion of human Ig heavy and human Ig kappa light chain loci and differ in the number of human VH (variable domain of heavy chain) and VL (variable domain of light chain) genes.

48 Mice were immunized alternating intraperitoneally (IP) with 20 µg antigens and subcutaneously (SC, at the tailbase) with the same immunogen, with an interval of 14 days. A maximum of eight immunizations were performed, 4 IP and 4 SC.

The first immunization was performed with alpha-synuclein immunogens in complete Freund's adjuvant (CFA; Difco Laboratories, Detroit, Mich., USA), the following immunizations in incomplete Freund's adjuvant (IFA). When serum titers were found to be sufficient (dilution of serum of 1/50 or lower found positive in antigen specific screening assay as described in herein above on at least two sequential, biweekly, screening events), mice were additionally boosted twice intravenously (IV) with 10 µg alpha-synuclein immunogen protein in 100 µL PBS, four and three days before fusion.

The immunization protocols are shown in FIG. 1.

Antibody 37 came from an immunization protocol where human full length a-Synuclein-fibrils was used, alternating with alpha-synuclein C-terminally truncated forms with amino acids 1-60 and 1-119.

Antibody 285 came from an immunization protocol where Human α-Synuclein-monomer 1-140 was used for the first 4 immunizations. If there was no titer, the immunization was continued with fibrils (ip/sc), otherwise it was continued with monomer.

3. HuMab Hybridoma Generation

HuMAb mice with sufficient antigen-specific titer development as defined above were sacrificed and the spleen and lymph nodes flanking the abdominal aorta and caval vein were collected. Fusion of splenocytes and lymph node cells with a mouse myeloma cell line was done by electrofusion using a CEEF 50 Electrofusion System (Cyto Pulse Sciences, Glen Burnie, Md., USA), essentially according to the manufacturer's instructions. Fused cells were seeded in fusion medium containing 10% Fetal Clone I Bovine serum (Perbio), 1 mM sodium pyruvate (Cambrex), 0.5 U/mL penicillin, 0.5 U/mL streptomycin (Cambrex), 50 µM 2-mercaptoethanol (Invitrogen), 600 ng/mL interleukin 6 (IL-6) (Strathmann), 1×HAT (Sigma) and 0.5 mg/mL kanamycin (Invitrogen) in HyQ mADCF-Mab (Perbio). After ten days, supernatant was harvested and cells were refreshed with harvest medium, containing 10% Fetal Clone I Bovine serum, 0.5 U/mL penicillin, 0.5 U/mL streptomycin, 600 ng/mL IL-6 and 1× proHT (Cambrex) in HyQ mADCF-Mab. Supernatants of the hybridoma cultures were screened by primary screening assays. Supernatants were characterized for binding to eight different ligands. These included 4 orthologs: human, mouse, rat and cynomologus monkey, human alpha-synuclein Beta-synuclein and human Gamma-synuclein (SEQ ID NOs 37-41) and lastly they were tested for their ability to bind to a human alpha-synuclein derivative that lacked residues 120-140 of alpha-synuclein.

The screening of anti-alpha-synuclein antibodies was performed using a high throughput suspension ELISA format using automated liquid handling systems (Genmab A/S). The reading of the plates was performed by two systems, the FMAT 8200 from Applied Biosystems was used to read 384 well plates and the ImageXpress Velos Cytometer from Molecular Devices was used to read the 1536 well plates.

In the primary screen clones were characterized by their ability to bind 8 different ligands. These included a series of 4 shuffle constructs: A-Syn-AAKK-BAP, A-Syn-BAAK-BAP, A-Syn-BBAA-BAP, A-Syn-BBKK-BAP (SEQ ID NOs:11-14), alpha-synuclein 120-140 deletion-BAP, nitrated human alpha-synuclein-BAP and oxidized human alpha-synuclein-BAP.

In short, the sera or supernatant potentially containing alpha-synuclein specific antibodies were added to the beads to allow binding to alpha-Synuclein and/or alpha-synuclein derived constructs. The binding of the anti-alpha-synuclein antibodies is detected using a fluorescent conjugate, DyLight649 conjugated goat antihuman IgG, Fc specific. Two known mouse anti-alpha-synuclein antibodies, LB509 and Syn211, were included in screenings as positive controls. To ensure specific detection of alpha-synuclein antibodies, an anti-alpha-synuclein sera pool is used as a negative control in the 384 well format titer screening while human ChromPure IgG is used in the 1536 well format 8-bead based assay.

Hybridoma cells from the best primary wells were seeded in semisolid medium made from 40% CloneMedia (Genetix, Hampshire, UK) and 60% HyQ 2× complete medium (Hyclone, Waltham, USA). For each primary well, a well of a Genetix black 6-well plate was seeded. From each well, 25 sub clones were picked, using the ClonePix system (Genetix). The sub clones were picked in harvest medium. After seven days, the supernatants of the sub clones were screened again for Synuclein-specific human IgG binding and the human IgG concentration was measured using Octet (Fortebio, Menlo Park, USA). From each primary well, the best sub clone was selected and expanded in expansion medium containing only 600 ng/mL IL-6, 0.5 U/mL penicillin, 0.5 U/mL streptomycin and 1× proHT. The sub clones were expanded from one 96-well plate well to one 24-well plate well to four 24-well plate wells to six 6-well plate wells. Clones derived by this process were designated as primary clones (PC).

Additional antibody binding studies were performed using Octet 384RED (Fortebio, Menlo Park, USA). HuMab antibody solutions of 2 µg/ml were made by dilution in sample diluent (ForteBio, art. No. 18-5028). Amine reactive sensors (ForteBio, art.no. 18-0008) were used for immobilization of HuMabs. Prior to coupling to amine reactive sensors, HuMabs were diluted in MES pH 6.0 buffer (18-5027). Coupling was performed at 30° C. and 1000 rpm as follows: Amine reactive sensors were pre-wet in PBS and subsequently activated with EDC/NHS(ForteBio. Art.no. 18-1033/18-1034) activation solution (according to manufacturer's instruction) for 300 seconds. Activated sensors were immobilized with HuMabs during 600 seconds.

The binding of 37 and 285 in Octet to recombinant human, cynomolgus and mouse alpha-synuclein, and lack of binding to human beta or gamma-synuclein is shown in FIG. 2

4. Sequence Analysis of the Synuclein-Specific HuMab Variable Domains and Cloning in Expression Vectors Total RNA was prepared from 0.2 to 5×106 hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f and p33Kappa expression vectors (containing the human IgG1/kappa constant domain encoding sequences), by ligation independent cloning (Aslanidis, C. and P. J. de Jong, Nucleic Acids Res 1990; 18(20): 6069-74). For each antibody, 16 VL clones and 16 VH clones were sequenced. Clones with a correct Open Reading Frame (ORF) were selected for further study and expression. Vectors of all combinations of heavy chains and light chains were transiently co-expressed in Freestyle™ 293-F cells using 293fectin.

In the case of GM37 sequencing of the VH region identified an extra cysteine in the CDR3 domain at position 106. In order to eliminate the possibility of misfolding and potential loss of antibody activity due to disulfide bond formation the cysteine was mutated to serine at position 106.

Comparator antibody 9E4 was generated based on the VH and VL sequence derived from hybridoma PTA-8221 (US patent 20080175838) (SEQ ID NO 42 and 43)

5. Expression/Purification of Antibodies

Antibodies were produced by transfection in HEK293 6E cells using the pTT5 vectors and PEIpro as a transient transfection agent (National Research Council of Canada). In short, The heavy and light chains were transfected into HEK293 cells using PEIpro (VWR), and cells were supplemented with TN1 (Sigma) 24 hours after transfection. Cells were grown until the viability approached 50%, and yield of antibody measured by easy IgG titre (Thermo). Culture supernatant was filtered over 0.2 µm dead-end filters, loaded on 5 mL Protein A columns (rProtein A FF, Amersham Bioscience) and eluted with 0.1 M citric acid-NaOH, pH 3. The eluate was immediately neutralized with 2M Tris-HCl, pH 9 and dialyzed to 12.6 mM $NaH_2PO_4$, 140 mM NaCl, pH 7.4 (B.Braun), O/N. After dialysis, samples were sterile-filtered over 0.2 µm dead-end filters. Purity was determined by SDS-PAGE and concentration was measured by nephelometry and absorbance at 280 nm. Purified antibodies were aliquoted and stored at −80° C.

Example 2: Antibody Characterization Using Surface Plasmon Resonance

Real time binding of the antibodies to alpha-synuclein was measured using a BIAcore® 3000. A capture surface was prepared by amine-coupling a polyclonal rabbit Anti-Mouse antibody (part of Mouse Antibody Capture Kit, GE Healthcare, Cat. no: BR-1008-38) in first flow cell (Fc1) and second flow cell (Fc2) of a CM5 chip (BIAcore®). The mouse antibody was captured in Fc2 at the concentration required to achieve a ligand level of around 500RU. The baseline was allowed to stabilize for 10 min before injecting analyte (ASynBAP) in Fc1-2 at 30 μl/min. ASynBAP was run at 100-3200 nM and 25-3200RU, respectively. The highest concentration in each titration series was run in duplicate. The surface was regenerated with 10 mM Glycine-HCl, pH 1.7 (30 sec inject) to remove captured mouse antibody and analyte in the end of each cycle. HBS-EP (GE Healthcare, Cat. No: BR-1001-88) was used as running buffer and sample diluent in all experiments and the assay was run at 25° C. All samples were kept at 4° C. before acquisition.

Figure 3A:
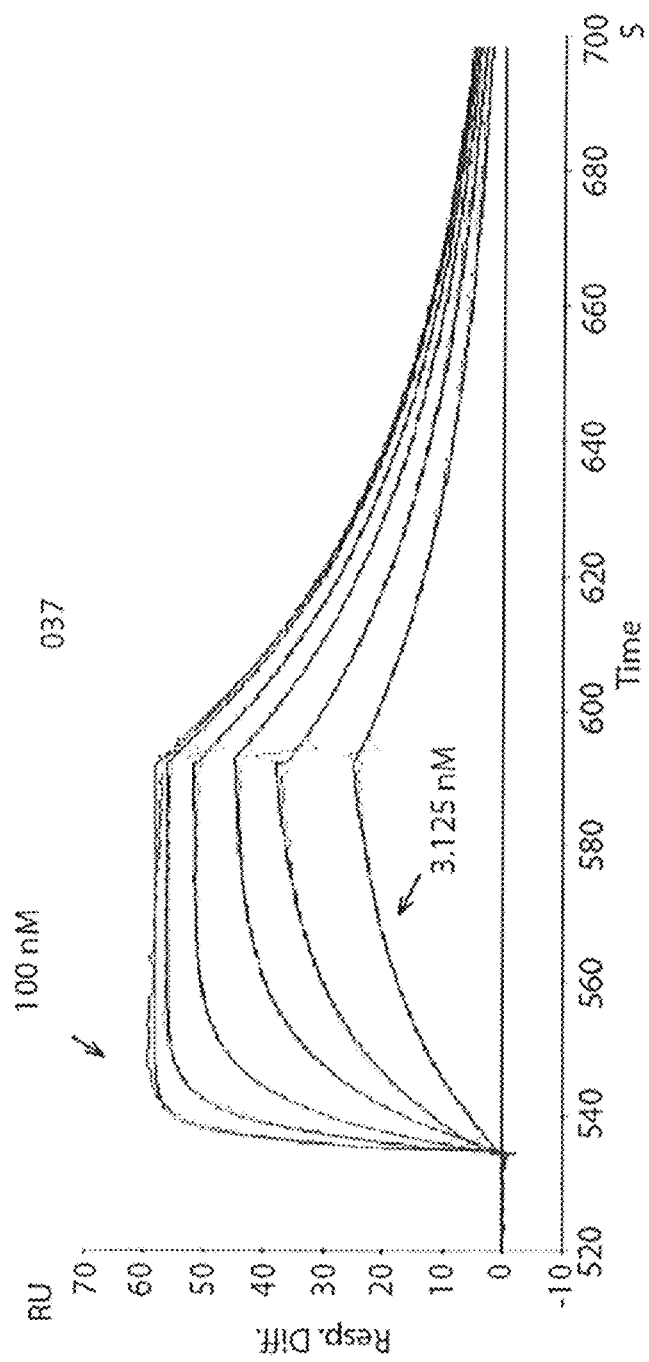
FIGS. 3A-3C show real time binding Affinity of GM37
FIG. 3A) Binding of antibody GM37 to alpha-synuclein measured in RU (Relative Units) (y-axis) over time (X-axis) as determined by SPR (BIAcore® 3000). Goat anti-human IgG was immobilized on the CM5 chip. GM37 was captured on the Goat anti-human IgG immobilized chip and series of concentrations of human alpha-synuclein (3.125, 6.25, 12.5, 25, 50, 100 nM) were tested on binding to the surface. The sensor surface was regenerated between each cycle.
Figures 3B, 3C:
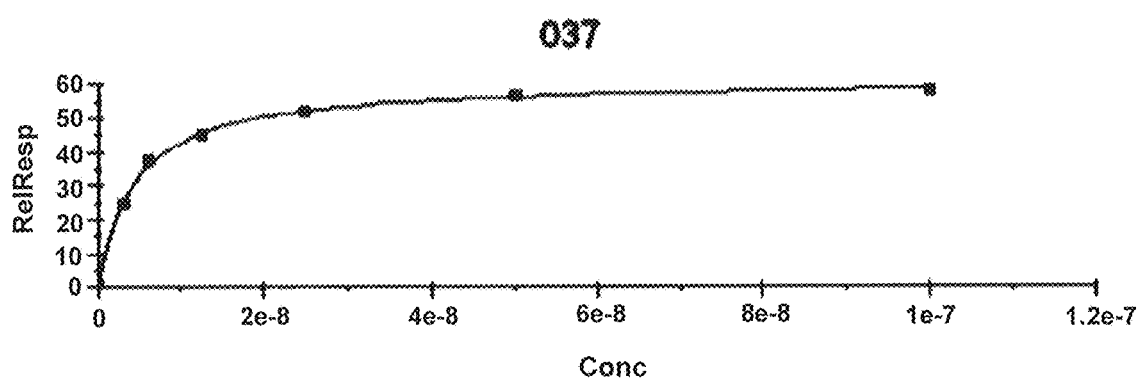
Figure 4A:
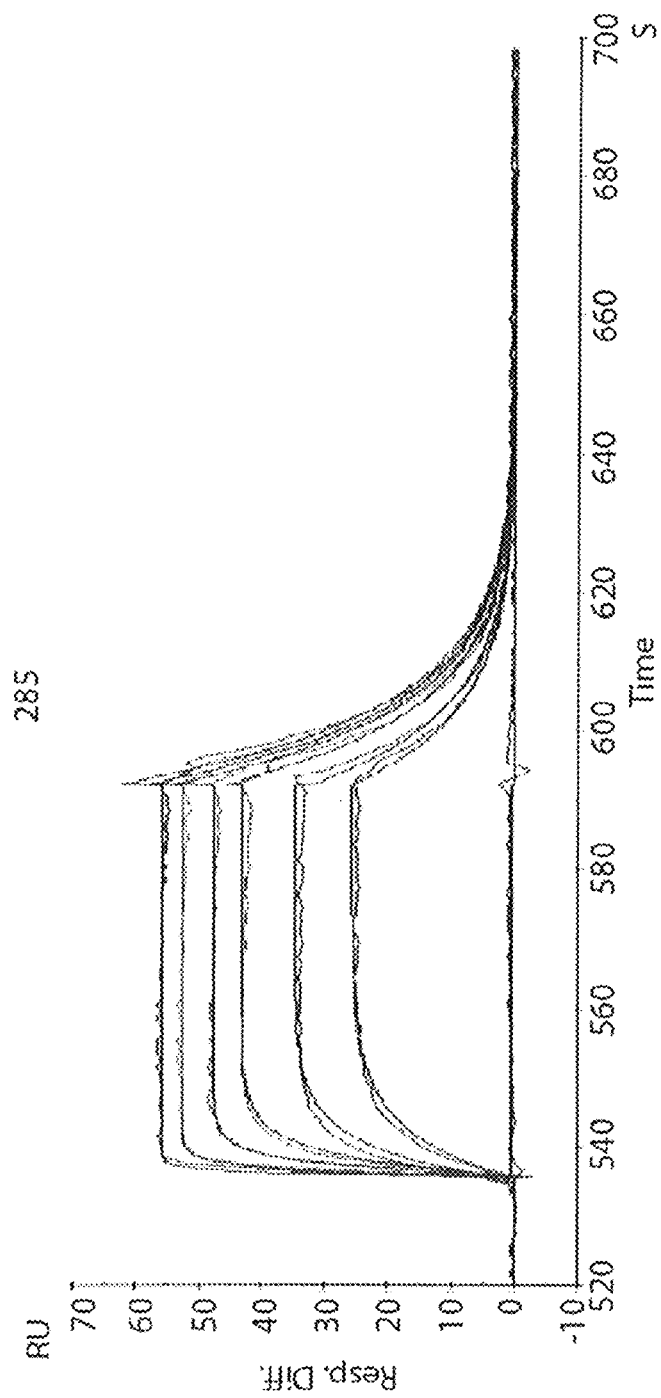
FIGS. 4A-4C show real time binding Affinity of GM285
Figures 4B, 4C:
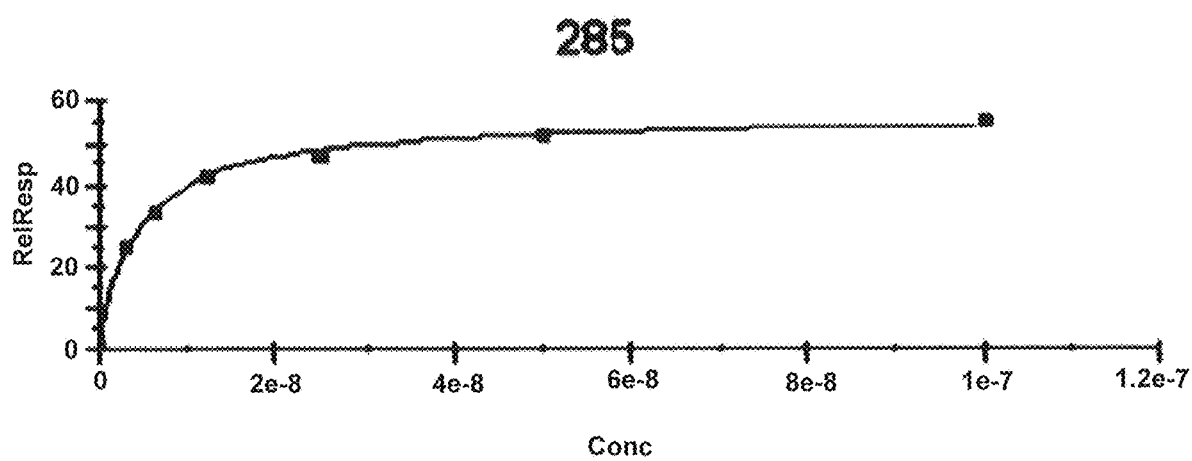
Figure 5A:
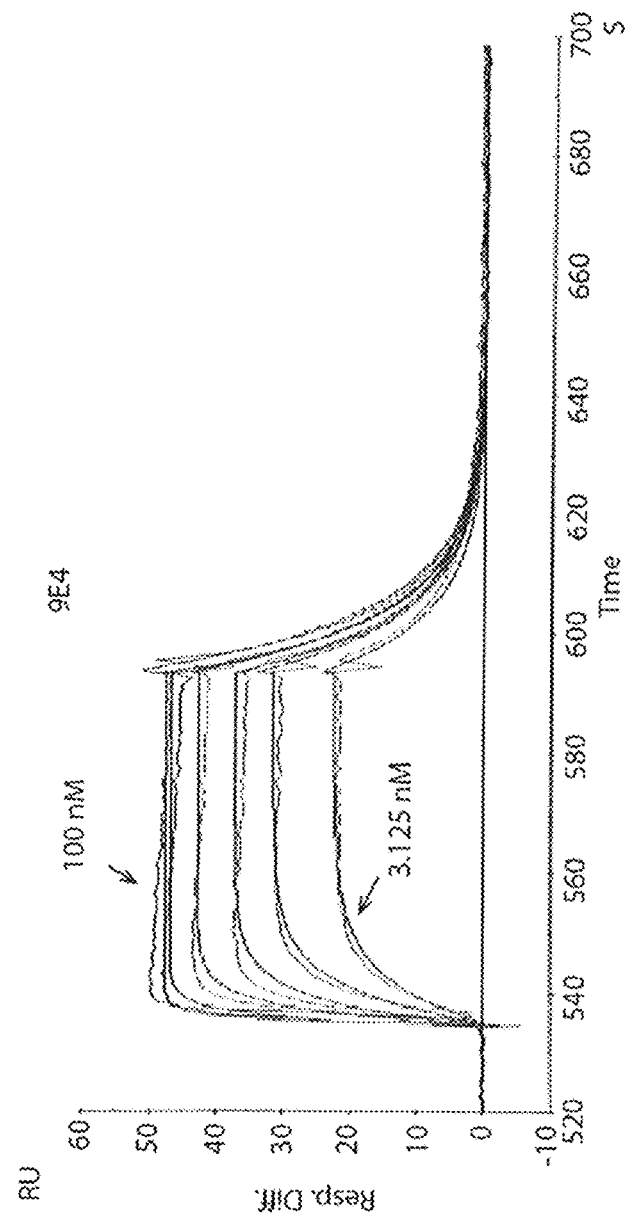
FIGS. 5A-5C show real time binding of comparator antibody 9E4
Figures 5B, 5C:
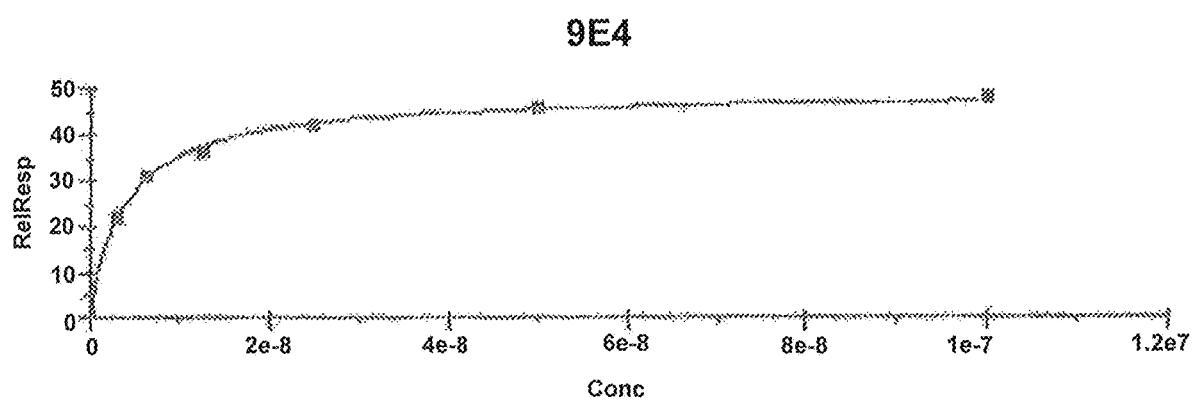

The response recorded in Fc1, where capture antibody had been immobilized but no Alpha-Synuclein antibody captured, was subtracted from the response in Fc2. A 1:1 or 2:1 binding algorithm was fit to the dataset using BIAevaluation software version 4.1.1. Results can be seen in FIGS. 3, 4 and 5 showing binding of antibody 37, 285 and 9E4 to human alpha-synuclein.

Example 3: Epitope Mapping

Figure 7A:
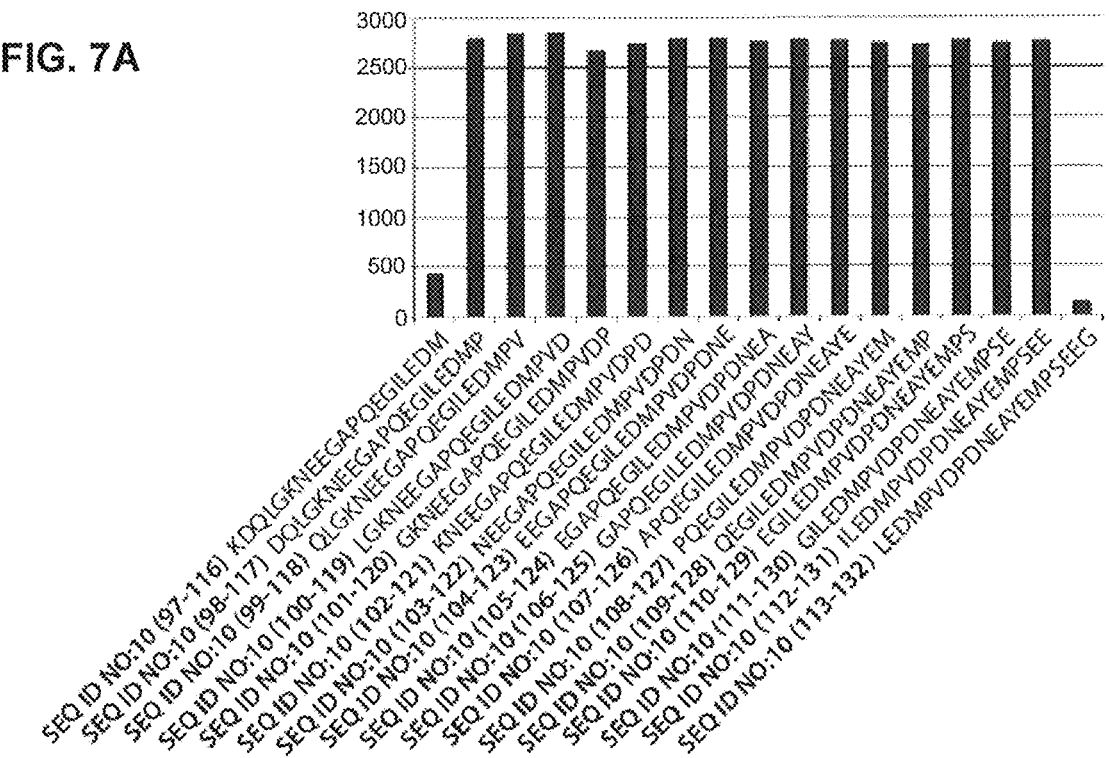
FIGS. 7A and 7B show epitope mapping of antibody GM37 and GM285. ELISA data showing relative levels of binding of the antibodies to sequential peptides (20 mers) derived from alpha-synuclein amino acid sequence 95-132 (the other nonbinding peptides are not shown).
Figure 7B:
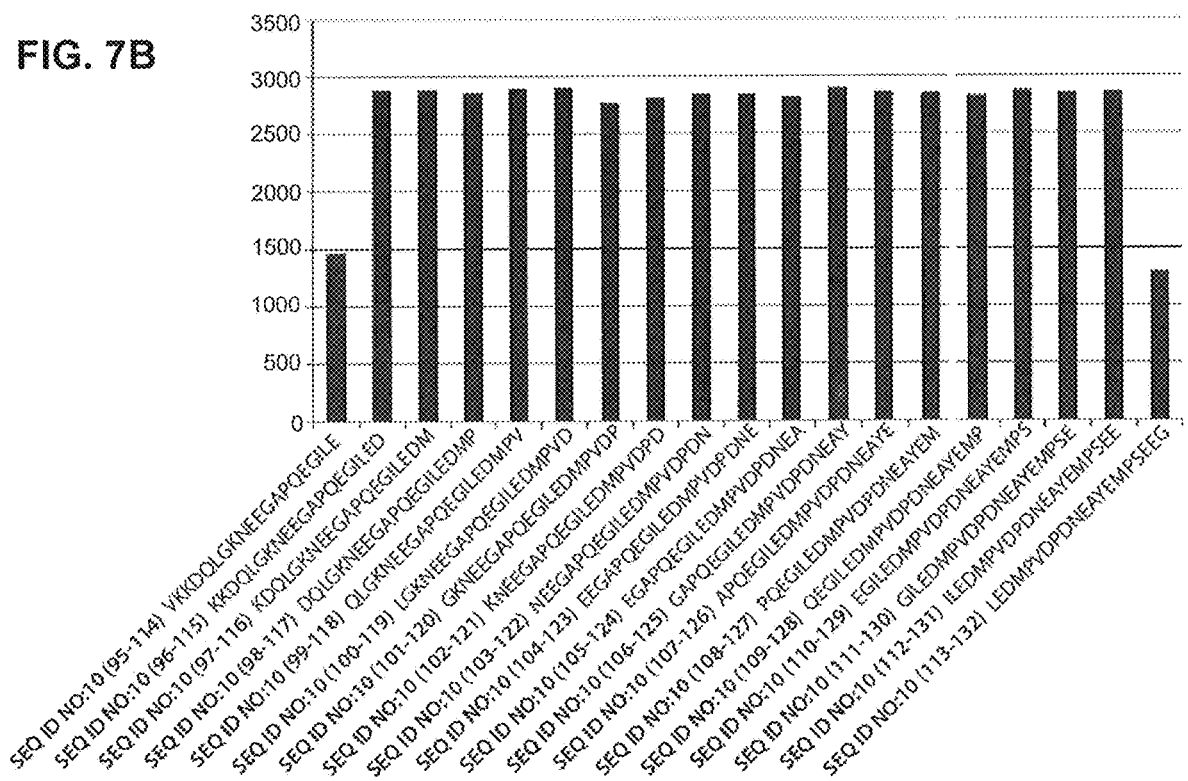
Figures 8A, 8B:
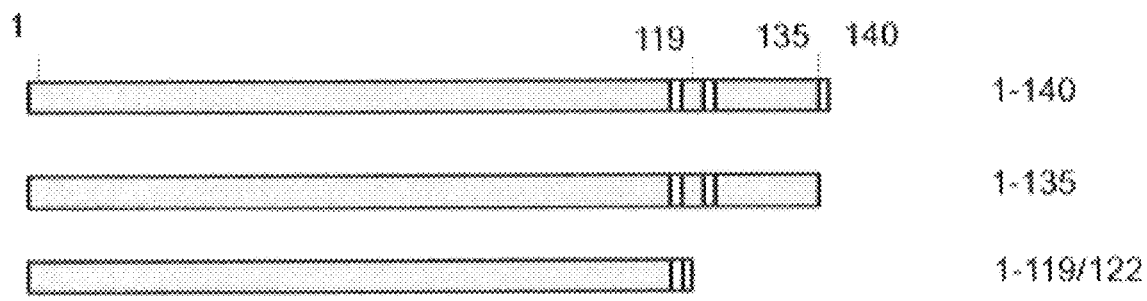
FIGS. 8A and 8B show a schematic representation of truncated forms of alpha-synuclein.

Epitope mapping of the antibodies to alpha-synuclein was done with arrays of overlapping linear peptides at Pepscan (Pepscan Zuidersluisweg 2 8243 RC Lelystad, The Netherlands). The binding of antibody to each of the synthesized 20 mer peptides was tested in a Pepscan based ELISA. The linear peptide array covering the entire coding sequence of alpha-synuclein, as well as all peptides with oxidized methionines or nitrosylated tyrosines, were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 μl/ml of 3 percent H2O2 were added. After one hour, the color development was measured. The color development was quantified with a charge coupled device (CCD)—camera and an image processing system. For data processing the values were obtained from the CCD camera range from 0 to 3000 mAU, similar to a standard 96-well plate ELISA-reader. The results were quantified and stored into the Peplab database. Occasionally a well contains an air-bubble resulting in a false-positive value, the cards are manually inspected and any values caused by an air-bubble are scored as 0. The binding data of antibody 37 and 285 to peptides containing the sequence ILEDMP or ILED respectively can be seen in FIG. 7.

Example 4: Immunoprecipitation of Alpha-Synuclein from Human Brain Homogenates of Cingulate Cortex from Patients with Dementia with Lewy Bodies The ability of the antibodies to bind to and pull down alpha-synuclein from crude homogenates of cingulate cortex from human DLB or healthy control (marked with *) was analyzed by immunoprecipitation. Frozen sample from human cingulate cortex (obtained throughTissue Solutions Ltd, Scotland) was dissected in cryostat, and 100 mg sample was added to 1600 μl cellytic M cell lysis reagent (Sigma C2978) containing protease inhibitors and phosphatase inhibitors (Roche). Brain tissue was homogenized until the sample is dissolved completely using Precellys bead homogenizer (Bertin technologies, France) 4×30 sec at 5000 rpm. The solution was centrifuged at 3000×g and the supernatant was used as the crude homogenate for immunoprecipitation.

Figure 9:
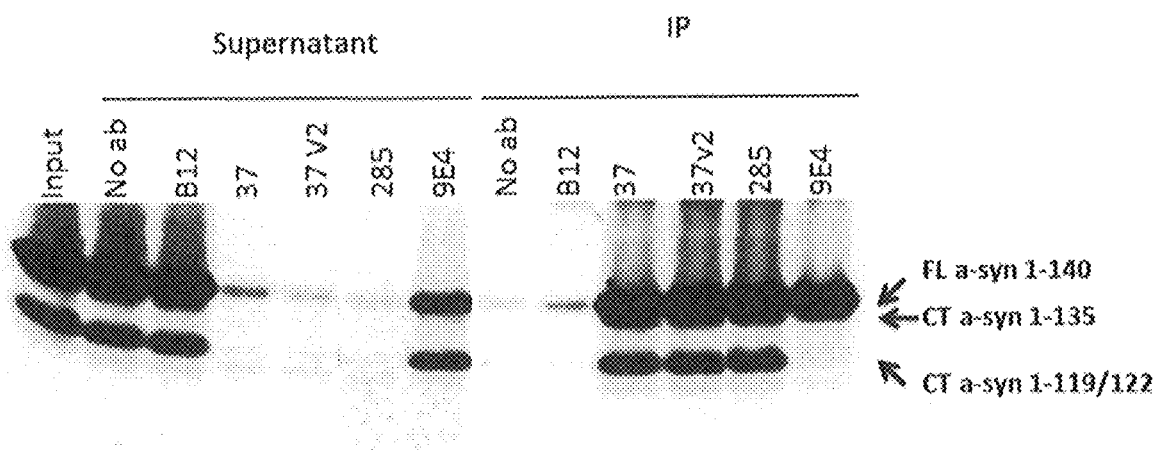
FIG. 9 shows that antibodies GM37 and GM285 immunoprecipitate full length alpha-synuclein as well as truncated alpha-synuclein from human brain. Crude homogenates of human DLB brain were incubated with the test antibodies (Beads (No ab), B12-human IgG1 control antibody not binding to alpha-synuclein, GM-37, GM37 variant 2, GM-285 and murine (m)9E4) and the immunodepleted supernatant and immunoprecipitated material was separated on SDS-PAGE. The western blot shows the bands representing the full length and the different truncated forms of alpha-synuclein being depleted from the supernatant and being immunoprecipitated with the antibodies (IP). As can be seen, the GM37, GM37v2 and GM285 antibody depleted the major alpha-synuclein species from the supernatant, and the IP shows these species, the truncated species 1-135, 1-119/122 and full length alpha synuclein. The 9E4 does not affect the 1-119/122 species but only IPs full length and 1-135 (Example 4).

For immunoprecipitation 10 μg of antibody was mixed with magnetic Dynabeads protein G beads using manufacturer's instructions (Life Technologies, Paisley, UK). The crude brain homogenate was diluted 30 fold in lysis buffer (Sigma). Antibody coupled dynabeads were mixed with 500 ul of diluted homogenate and incubated 90 minutes at room temperature under continuous mixing in a rotator. After incubation the beads were washed in washing buffer and the bound antigens were eluted using the non-denaturing elution buffer according to manufacturer's instructions (Dynabeads G protocol, Life Technologies, Paisley UK). The yield of the immunoprecipitation was visualized by Western blotting with detection mouse monoclonal anti-human alpha-synuclein antibody, (4612, Thermo Scientific). The patterns of bands representing different molecular weight forms of alpha-synuclein being pulled down differ between the 37, 37 variant 2 and 285 antibodies and the comparator antibody 9E4 in that the 37, 37v2 and 285 antibody can immunoprecipitate the major alpha-synuclein species, the full length alpha-synuclein (FL asyn 1-140) and the C-terminal terminal truncated species (1-135 and 1-119/122), while antibody 9E4 cannot immunoprecipitate the truncated species 1-119/122. FIG. 9.

Example 5: Inhibition of Protease Truncation of Alpha-Synuclein Fibrils by Antibodies in Cell Culture Recombinant alpha-synuclein monomers and fibrils can be taken up by primary neurons in culture. As shown schematically in FIG. 10, after uptake of the alpha-synuclein in neurons, it can be processed by intracellular proteases, such as Calpain I, with the major protease sensitive site at amino acid 119/122. To investigate truncation of alpha-synuclein by proteases mouse primary cortical neurons were prepared as described in Elvang et al. 2009 (Elvang et al. J Neurochem. 2009; 110(5):1377-87) and treated with cytarabine on DIV3 (3 days in vitro) to inhibit astrocyte growth. On DIV4 (4 days in vitro), the neurons were treated with sonicated (5 min at 50% power in cup horn sonicator) pre-formed alpha-synuclein fibrils (PFFs) at an end concentration of 0.7 μM alone or together with antibodies in the indicated concentrations. After 24 hours of incubation, the media was harvested and the cells were lysed. Western Blots was run on both media and cell lysate using the 4B12 antibody (FIG. 11A) (Pierce MA1-90346) and a secondary anti-mouse antibody. After probing with 4B12+anti-mouse, the blots were stripped and reprobed with an anti-human-IgG antibody. On blot with 4B12, it can be seen that in the media from cells treated with PFFs only, there were strong bands at 14 and 12 kDa, where 14 kDa represents the full-length alpha-synuclein (FL-asyn) and 12 kDa represents the C-terminally truncated fragment 1-119/122 (CT-asyn). In addition to that, there were higher molecular weight bands, most likely representing SDS-resistant oligomeric species. Co-treatment with the isotype control antibody B12 did not change this pattern of proteolysis or uptake.

Figure 10:
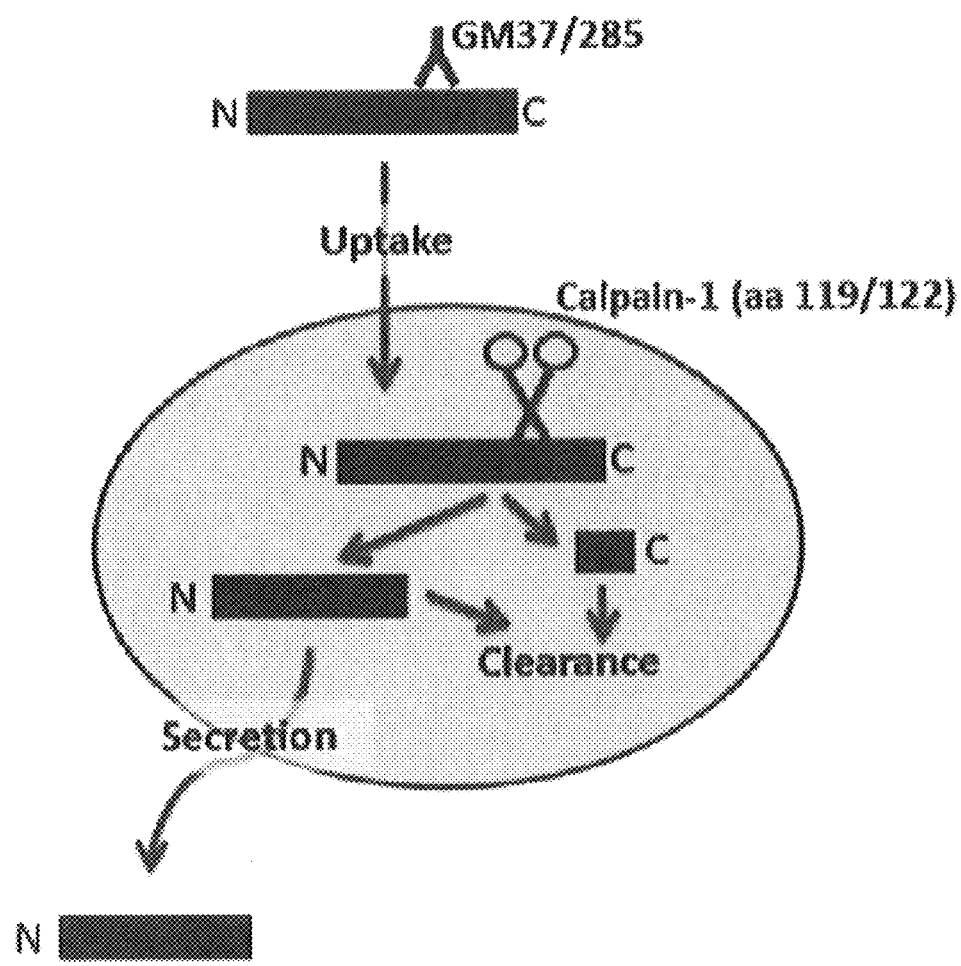
FIG. 10 shows schematics of the proteolysis of alpha-synuclein fibrils cleaved by calpain at amino acid 119/122. Alpha-synuclein fibrils (PFF) are added to the culture with (PFF+) or without (PFF) test antibody. The presence of GM-37/285 inhibit the formation of the truncated alpha-synuclein in cells and secreted into the cell media.
Figure 11A:
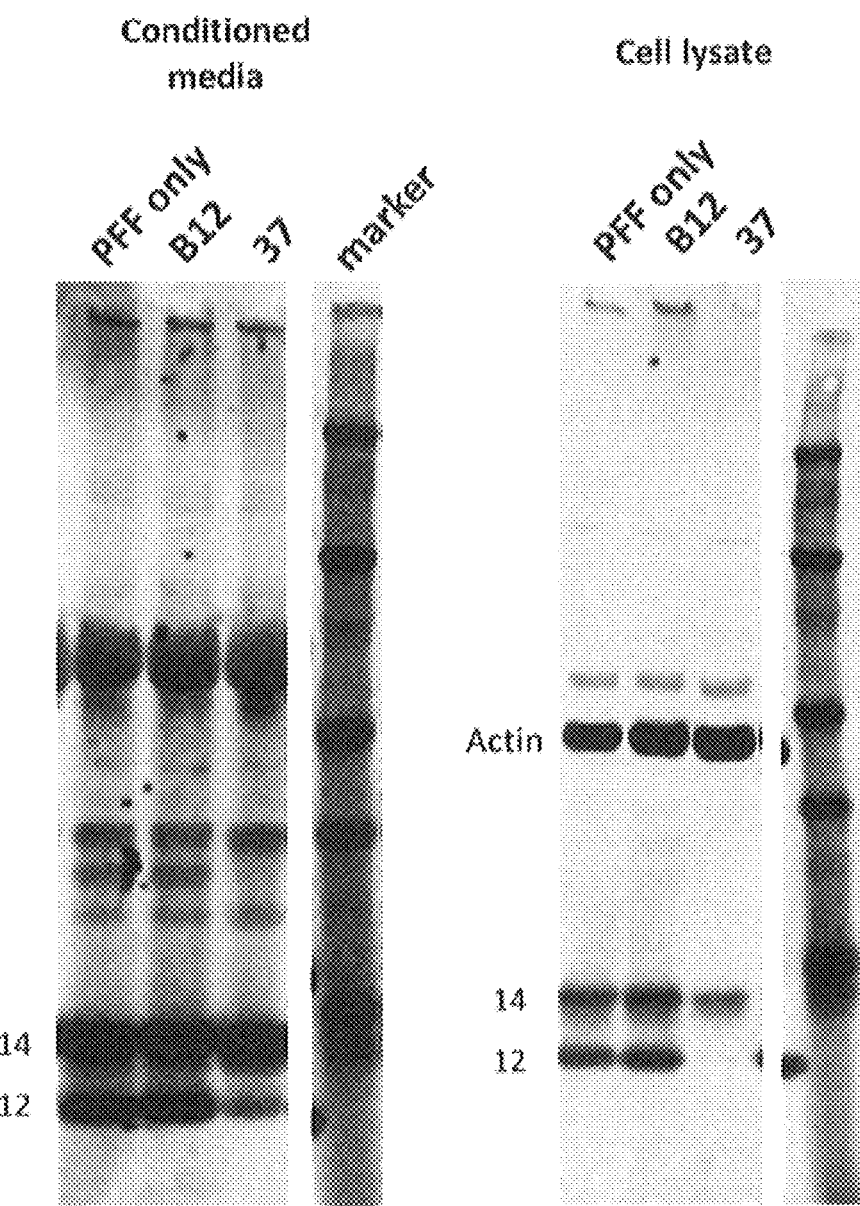
FIG. 11A shows that GM37 inhibits the formation of the truncated band (12 KD) in both the media and in cell lysates of primary mouse cortical cultures treated with PFFs. Proteins were separated by SDS-PAGE and western blotted to detect different species of alpha-synuclein. In cells treated only with PFF or the control antibody (B12) two monomeric alpha-synuclein bands are detected at 12 and 14 kDa, representing truncated and full length alpha-synuclein, respectively. In the presence of GM-37 there is only a faint band at 12 Kd indicating that the majority of the cleavage is blocked. This effect is also reflected in the in the media of the cells. The relative levels of accumulation may also be inhibited by the presence of GM-37 as reflected in the reduction in the relative intensity of the 14 Kd band. Alternatively there may be reduced amount of the 14 Kd band available for uptake by the cells. (Example 5).

In the media from cells treated with fibrils together with 37 there was mainly full length alpha-synuclein (14 kD) and only small amounts of the terminally truncated band (12 kD). In cell lysate inform cells treated with fibrils together with 37 there was full length alpha-synuclein only, indicating that 37 prevent cleavage of FL-alpha-synuclein. Furthermore the total amount of FL-alpha-synuclein is reduced in relation to cells treated with PFFs only or B12 control antibody. It has been shown by several groups (Games et al, Am J of Pathol, Vol. 182, No. 3, March, 2013; Ritchie et al, Health, Vol. 4, Special Issue, 1167-1177, 2012; Mishizen-Eberz, Biochemistry, 2005, 44, 7818-7829; Dufty et al, Am J of Pathol, Vol. 170, No. 5, May 2007) that alpha-synuclein can be cleaved by Calpain-1. The cleavage site of Calpain-1 for fibrillized alpha-synuclein has been found to be in the region 114-122 (Mishizen-Eberz, J of Neurochem, 86, 836-847, 2003). In vivo in transgenic animals and human brain 1-119/122 seems to be the main cleavage product—in alpha-synuclein, the cleavage is likely after asparte 119 or asparagine 122, which is deamidated to aspartate and is cleaved by Calpain or another protease with similar cleavage specificity. These results indicate that antibody 37 is able to inhibit C-terminal truncation of alpha-synuclein. The epitope of antibody 37 overlaps with the enzyme Calpain-1 binding site, so binding of 37 to alpha-synuclein could directly inhibit binding and cleavage mediated by Calpain-1 (FIGS. 10 and 11).

Figure 11B:
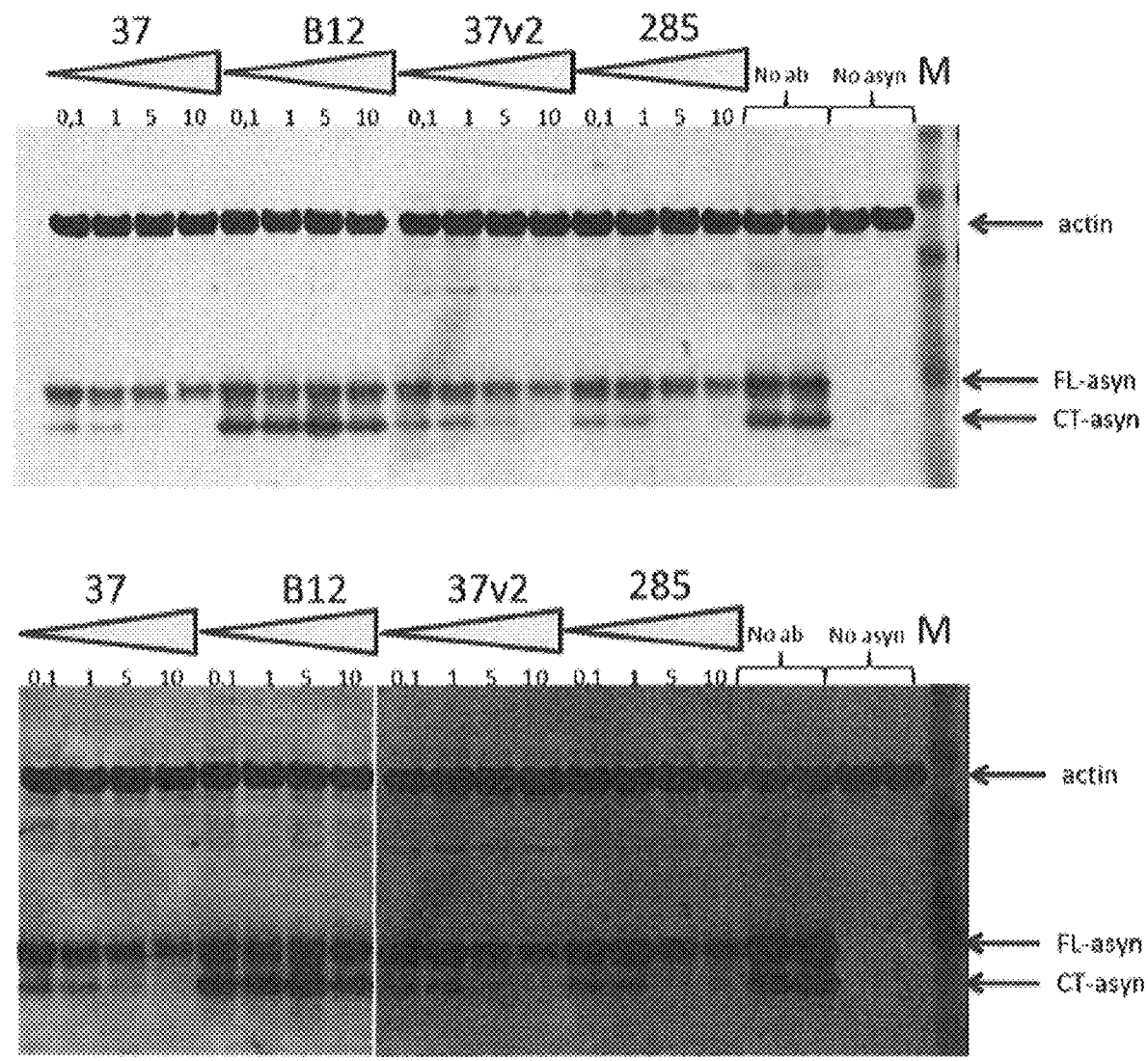
FIG. 11B shows dose dependent inhibition of proteolysis of alpha-synuclein fibrils by antibodies GM37, GM37 variant 2 and GM285. In cell lysates from primary mouse cortical cultures at low antibody concentration (0.1 ug/ml) there are both a band representing full length (FL) alpha-synulcein and a band representing C-terminally truncated (CT) alpha-synuclein (indicated by arrows). Increasing antibody concentration to 1, 5 and 10 ug/ml leads to reduced proteolysis of alpha-synuclien fibrils in cells. This is observed with both antibody GM37, GM37v2 and GM285. Control samples are treated with a human IgG1 antibody B12 not recognising alpha-synuclein. There is also a control with no antibody added (No ab), and cells with no alpha-synuclein fibrils added (No Asyn). The total amount of alpha-synuclein is also reduced in samples treated with 37, 37v2 and 285 compared to B12 or "no antibody" control, indicative that all three antibodies reduce accumulation of alpha-synuclein in cells in concentration dependent manner. The actin band on the top of the gel shows equal loading of the samples (Example 5).

The epitope of 285 overlaps with the epitope of 37 and it would also be expected to inhibit the protease cleavage. The amino acid sequence of 37v2 only differs from 37 at one amino acid in CDR and has similar binding as 37, so it would also be expected to inhibit protease cleavage in similar manner to 37. To investigate if the effect of the antibodies were dose-dependent, a 24-hour experiment with co-addition of PFFs and antibodies to primary cortical neurons was set up. The concentration of PFFs were stable (10 μg/ml), whereas the concentrations of control antibody B12, and antibodies 37, 37v2 and 285 that was tested was 10, 5, 1 and 0.1 ug/ml. Alpha-synuclein on Western Blots were detected with 1904/4B12 antibody (Abcam), which has an epitope in the region 103-108 and therefore binds to both the FL and the C-terminally truncated alpha-synuclein (FIG. 11B). As can be seen from FIG. 11B, both GM37, 37v2 and GM285 have a dose dependent inhibition of protease cleavage, with almost complete inhibition of the cleavage at high concentration of the antibody.

Figure 12A:
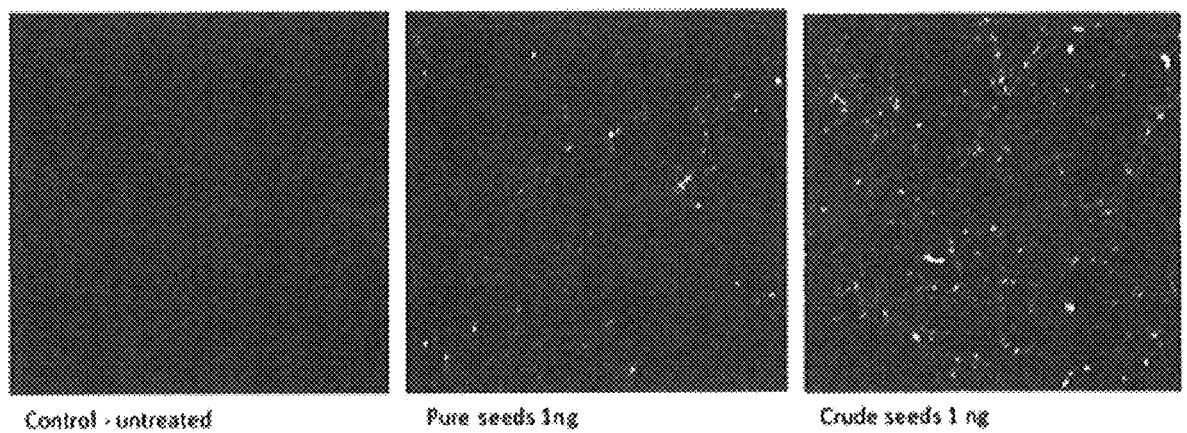
FIGS. 12A-12D show the impact of GM37 and GM285 on seeding of alpha-synuclein aggregation and alpha-synuclein phosphorylation in mouse primary cortical neurons.

Example 6: Antibody-Mediated Inhibition of Seeding of Alpha-Synuclein Aggregation in Cell Culture Several studies have shown that exogenous addition of recombinant alpha synuclein fibrillar aggregates can enter cells and recruit endogenous alpha-synuclein and induce alpha-synuclein aggregation and phosphorylation in vitro and in vivo, which resemble LB. (Volpicelli-Daley et al. 2011, Luk et al. 2012a, Luk et al. 2012b, Recasens et al. 2013, Peelaerts et al. 2015). To study seeding of endogenous mouse alpha-synuclein by recombinant alpha-synuclein seeds, mouse primary cortical neurons prepared as above are plated in 96 well plates (15,000 cells per well). On day 5 in vitro culture (DIV), 50% of media is changed and supplemented with cytosine arabinoside (final conc. of 1 uM). On DIV 6, half of the media is changed with glia conditioned media along with alpha synuclein fibrillary material, either crude fibril seeds or pure seeds. The crude fibril seeds are made from recombinant monomeric human alpha-synuclein, which was isolated from bacteria and the monomers were filtered through an Amicon Ultra 100.000 cut off filter (Millipore cat. No UFC510096) and adjusted to concentration of 1 mg/ml in PBS, pH 7.4. To make fibril crude seeds, the monomer solution was incubated in thermomixer at 37 C with continuous mixing (800 rpm) until plateu is reached (evaluated by daily measures with Thioflavin S). To minimize evaporation a drop of mineral oil was added to cover the solution. The total time for incubation was 5-7 days, The pure seeds are made from crude fibril seeds that are centrifuged to purify them and the aggregated pellet is resuspended in fresh PBS and sonicated. The antibodies are added once on DIV 6 along with alpha-synuclein crude seeds. Half of the media in the primary neurons is replaced with glia conditioned media every week to maintain them up to DIV21. The neurons are fixed and stained for Phospho-synuclein using a rabbit antibody specific for phosphorylation of alpha-synuclein at amino acid S129 (abcam 51253), followed by a fluorescently labelled anti-rabbit antibody, fluorescence is quantified using automated fluorescent microscopy, Cellomics Arrayscan. Nuclei were detected in one channel and defined the number of valid cells. Phosphorylated alpha-synuclein spots were detected in another channel in a pre-defined ring-formed area surrounding the nucleus, thus representing the cytoplasm of the cells. The average number of spots per cell was calculated. Example of cell staining is shown in FIG. 12A. Phosphorylated alpha synuclein spots are not seen in untreated neurons. Neurons incubated with crude or pure seeds (1-10 ng per well) induce phosphorylation of alpha synuclein (FIG. 12A). In neurites, phosphorylated synuclein appears as spots or punctate and some of the phospho-synuclein in the neurites appear elongated.

For fractionation studies cells were harvested in phosphate buffered saline solution (PBS) and centrifuged. Pellet was resuspended in 1% triton buffer with protease inhibitors. Samples were kept on ice for 15 min. followed by sonication. The samples were centrifuged at 100,000×g for 30 min. at 4 C. The supernatant is collected and labelled as soluble fraction. The pellet was washed once in triton buffer and re-suspended in 1% SDS buffer followed by sonication. Samples were centrifuged again at 100,000×g for 30 min. The supernatant is collected as insoluble fraction. The protein concentrations were measured and samples were run on 4-12% SDS_PAGE gel, blotted on membranes and alpha synuclein and phosphorylated alpha synuclein (S129P) are detected by 4B12/1904 antibody (Thermo scientific: MA1-90346-human synuclein), S129P-asyn antibody (abcam 51253) and mouse synuclein antibody (cell signalling-D37A6), respectively.

Figure 12B:
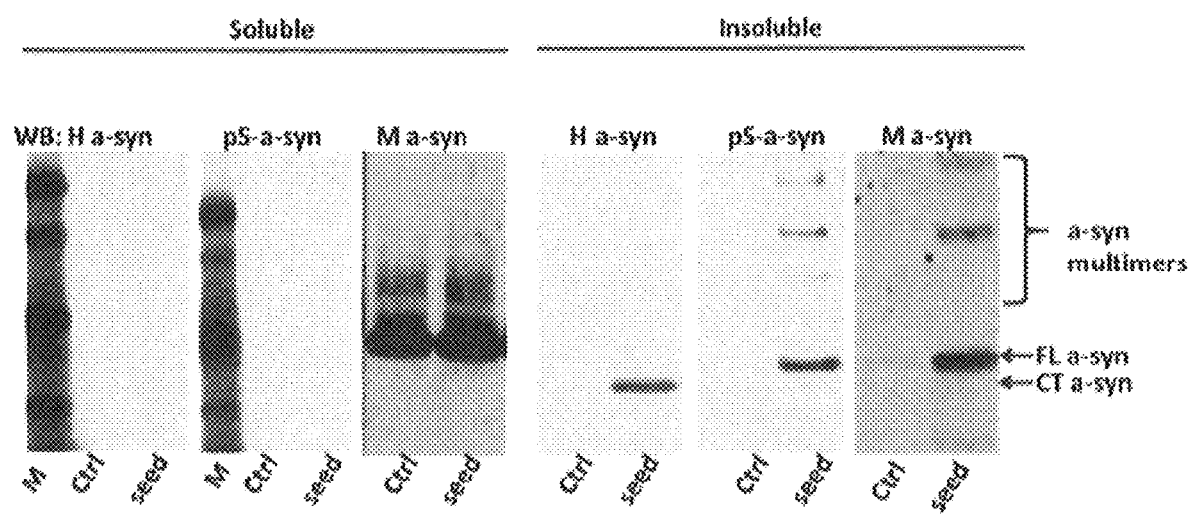

FIG. 12B shows the Western blot of the soluble and insoluble fraction from the primary neurons with and without crude seeds. As can be seen from FIG. 12B the addition of the seeds lead to accumulation of endogenous mouse alpha-synuclein and p-5129-alpha-synuclein and multimers of phosphorylated mouse alpha-synuclein in the insoluble fraction of the cells.

Figure 12C:
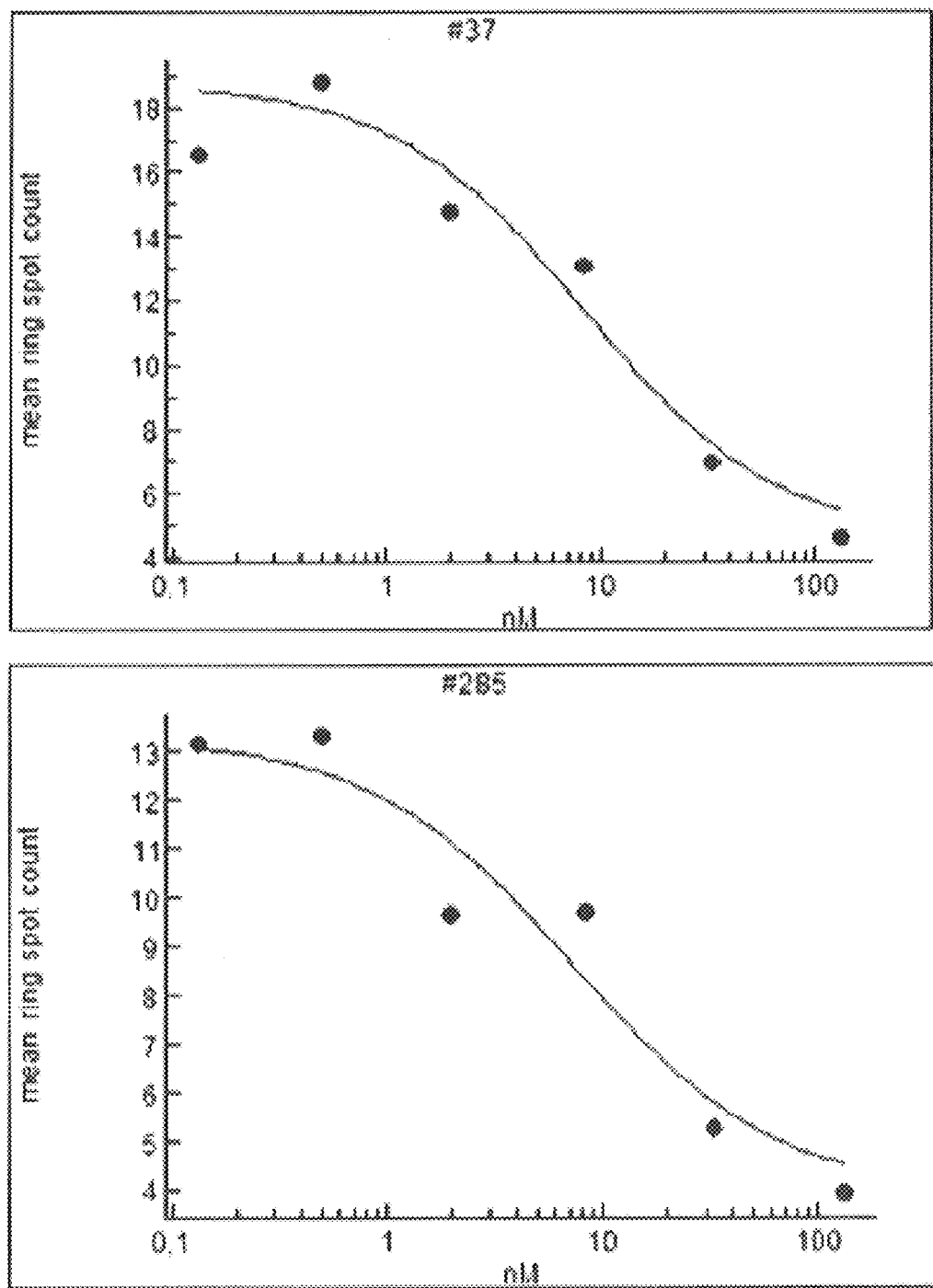
Figure 12C:
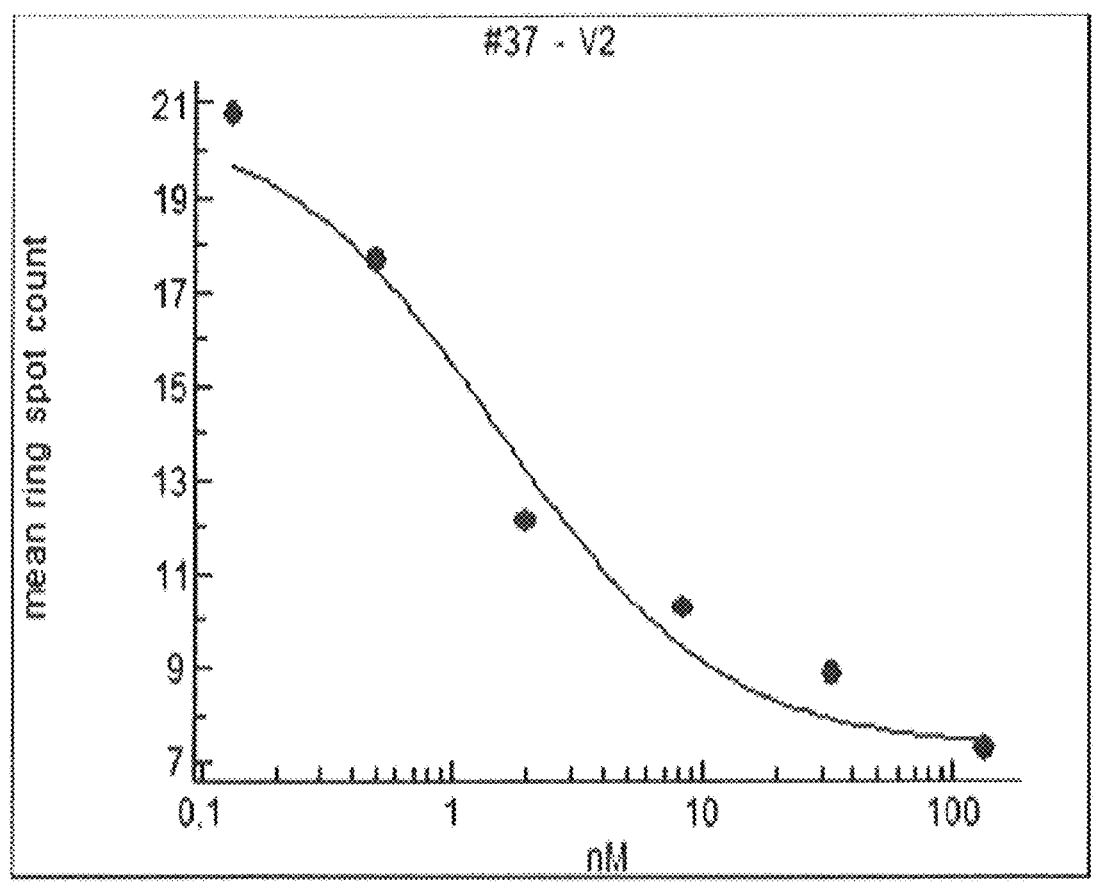
Figure 12D:
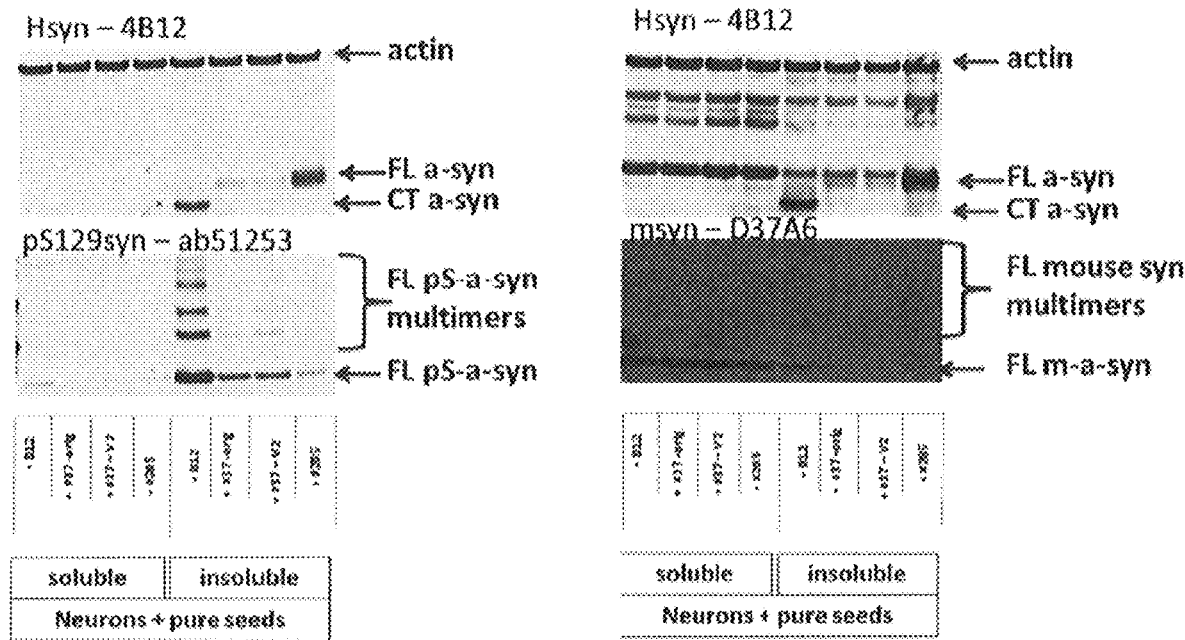

To test if antibodies can inhibit seeding, alpha synuclein synuclein seeds were used at conc. of 6.6 nM (10 ng/well). Different concentration of antibody and alpha-synuclein seeds were added together on DIV 6, to make a dose response (starting from highest antibody conc. at 133 nM down to 133 pM). The neurons were again fixed and stained for Phospho-synuclein (abcam 51253) and fluorescence from cells was quantified using automated fluorescent microscopy, Cellomics arrayscan. The spots/puncta per cell were counted in Cellomics arrayscan. As can be seen from FIG. 12C, both antibody 37, 37v2 and antibody 285 reduced alpha synuclein phosphorylation in neurons in a dose dependent manner with similar maximal inhibition for 37, 37v2 and 285 (around 70-75%) and EC50 around 5 nM. Fractionation of the cellular proteins to soluble and insoluble fraction after treatment with antibody at the highest concentration (133 nM) shows that both antibodies 37, 37v2 and 285 inhibited the truncation of the recombinant crude seeds and accumulation of C terminally truncated fragment (CTa-syn), and reduced the accumulation of phosphorylated endogenous mouse alpha-synuclein and aggregated forms of mouse alpha-synuclein in the insoluble fraction, as seen in FIG. 12D.

Figure 13:
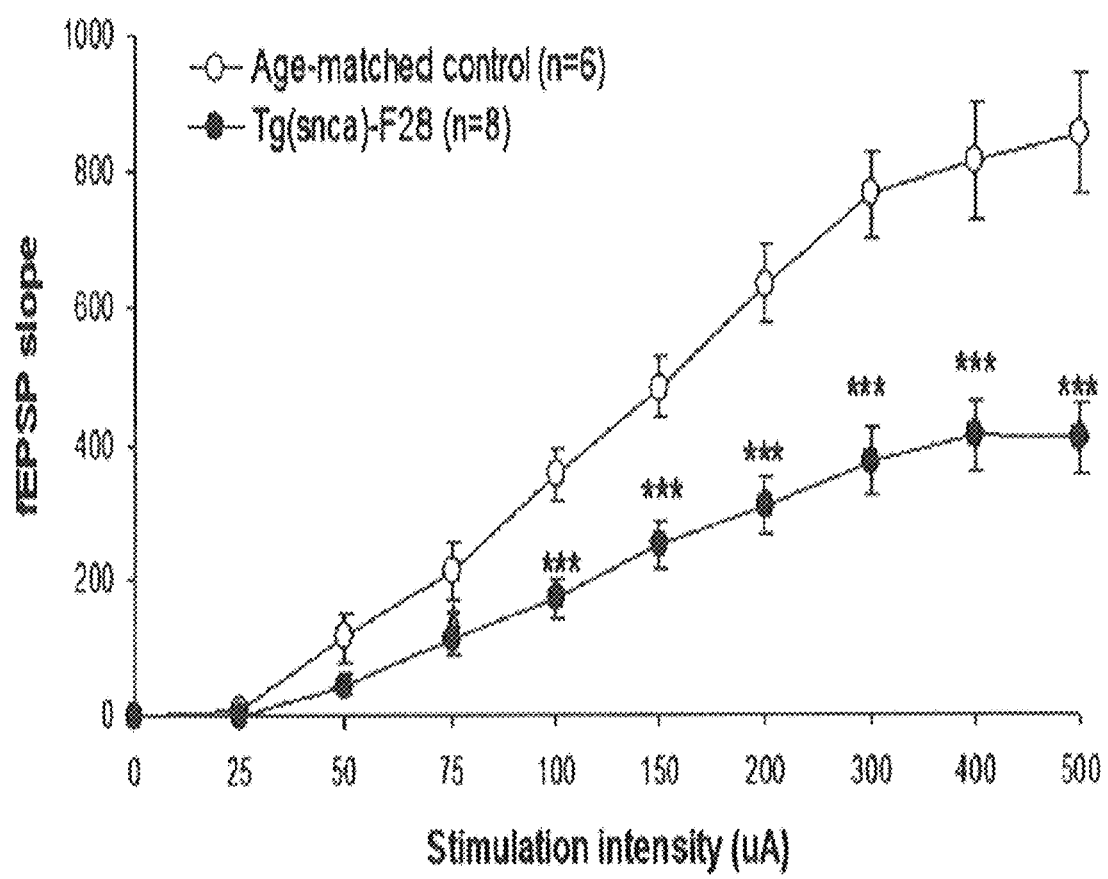
FIG. 13 shows basal synaptic transmission at the Schaffer collateral-CA1 synapse in the hippocampus of F28-snca transgenic and age-matched control mice. Field excitatory post-synaptic potentials (fEPSPs) were evoked by a single stimulus applied to the Schaffer collateral, and basal synaptic transmission was assessed by measuring the fEPSP slope as a function of the stimulation intensity. Short-term synaptic plasticity was evaluated by induction of paired-pulse facilitation. The different intensities of stimulation were 0, 25, 50, 75, 100, 150, 200, 300, 400, and 500 μA, and were applied successively in increasing order, with 2 to 3 repeats for each intensity. Basal synaptic transmission was found to be significantly impaired in F28-snca transgenic mice overexpressing wild-type alpha-synuclein compared to age-matched control mice (Example 7).

Example 7. Acute Electrophysiological Effects of Alpha-Synuclein Antibodies In Vivo High expression levels of human alpha-synuclein are present in the hippocampus of F28-snca transgenic mice, a model overexpressing wildtype alpha-synuclein under the control of the mouse alpha-synuclein promotor (Westerlund M, et al. Mol Cell Neurosci. 2008 December; 39 (4):586-91). Assessment of synaptic transmission and plasticity in the CA1 area of the hippocampus in 4 to 6 months old male F28-snca transgenic and age-matched control mice was performed by in vivo electrophysiology. The data shows that basal synaptic transmission is significantly impaired in F28-snca transgenic compared to age-matched control mice (FIG. 13).

F28-snca transgenic and age-matched control male mice (CRO breeding, Taconic Europe A/S) aged 4 to 6 months were single-housed in controlled temperature (22±1.5° C.) and humidity conditions (55-65%) and kept in a 12:12 hour light/dark cycle (lights on at 06:00 h). Food and water were available ad libitum.

Animals were anesthetized with an intraperitoneal (i.p.) injection of urethane (1.2 g/kg). Mice were then mounted in a stereotaxic frame, their temperature adjusted to 37.5° C. via a heating pad, and the skull was exposed. A platinum wire was placed in the frontal bone to act as a reference, and an additional hole was drilled for insertion of the recording and stimulating electrodes in the hippocampus, at the following coordinates according to the atlas of Paxinos and Franklin (Paxinos and Franklin's the Mouse Brain in Stereotaxic Coordinates, 4th Edition, 2001): recording, 1.5-1.7 mm posterior to Bregma, 1.0-1.2 mm lateral to the midline, 1.4-1.7 mm below the surface of the brain; stimulation, 1.8-2.0 mm posterior to Bregma, 1.5-1.7 mm lateral to the midline, 1.5-1.7 mm below the surface of the brain. Animals were left in the stereotaxic frame through the whole duration of the recordings and their level of anesthesia was regularly checked.

Field potentials (fEPSP) were evoked in the CA1 by electrical stimulation of the Schaffer collateral every 30 s, and the depth of the recording electrode was adjusted until a negative fEPSP was recorded in response to a unipolar square pulse. The slope of the evoked fEPSP was measured between 30 and 70% of the maximum amplitude of the fEPSP.

Once an optimal fEPSP was induced, basal synaptic transmission was assessed by the relationship between stimulation intensity and slope of the evoked fEPSP (input-output relationship). The different intensities of stimulation were 0, 25, 50, 75, 100, 150, 200, 300, 400, and 500 µA, and were applied successively in increasing order, with 2 to 3 repeats for each intensity. Basal synaptic transmission was found to be significantly impaired in F28-snca transgenic compared to age-matched control mice.

The identified impairments in basal synaptic transmission in F28-snca transgenic mice were used to test the GM37, GM285 and comparator h9E4 for their ability to block the alpha synuclein mediated effect.

Recordings were performed in all experiments 3 to 6 h following administration of a single dose of antibody at a dose of 15 mg/kg (i.p.). Basal synaptic transmission were recorded in both hippocampi in each animal when possible, and recorded as individual experiments.

Figure 14:
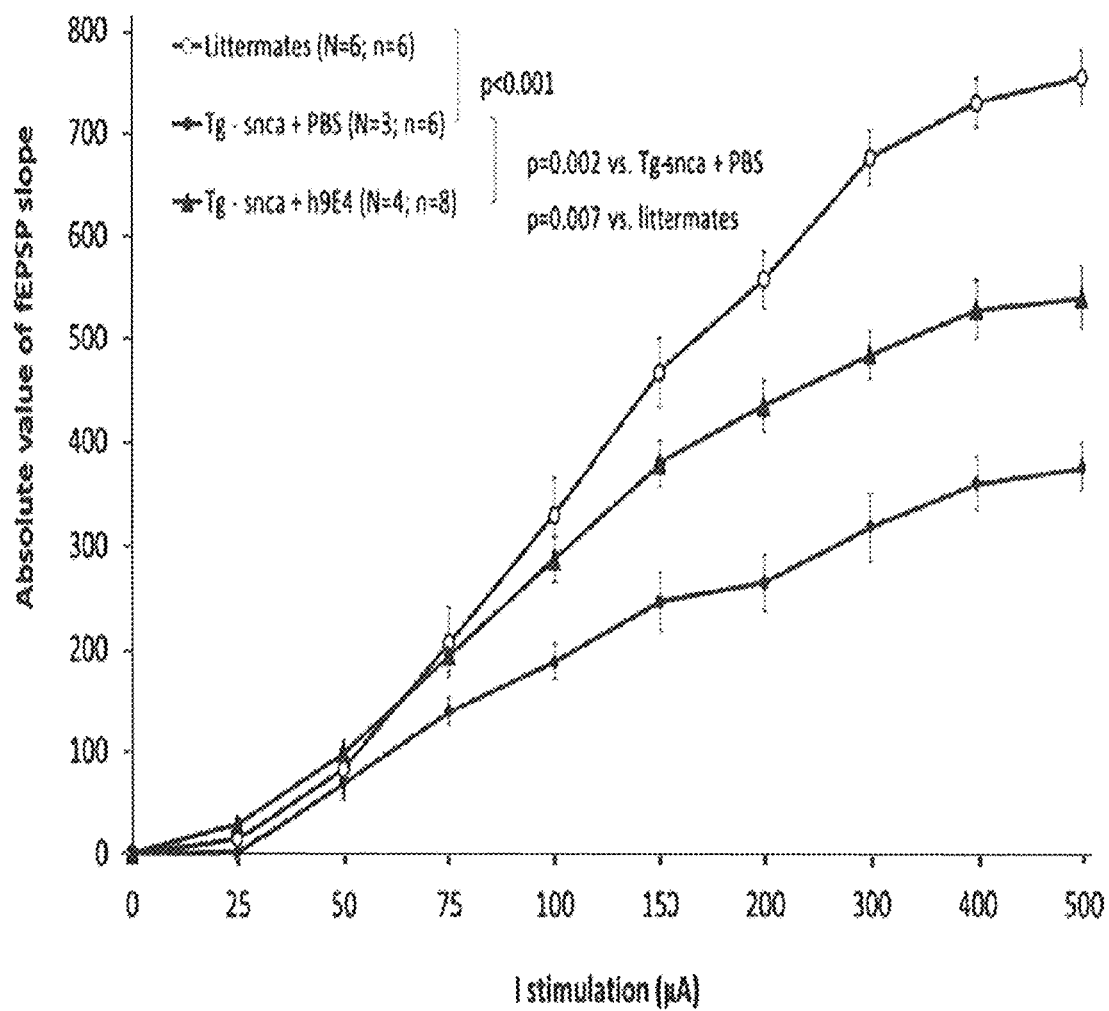
FIG. 14 shows the effect of the systemic administration of a single dose of human 9E4 (15 mg/kg, i.p.) on the impairment in basal synaptic transmission at the Schaffer collateral-CA1 synapse in the hippocampus of F28-snca transgenic mice. Field excitatory post-synaptic potentials (fEPSPs) were evoked by a single stimulus applied to the Schaffer collateral, and basal synaptic transmission was assessed by measuring the fEPSP slope as a function of the stimulation intensity. Acute treatment with h9E4 induced a significant reversal of the impairment in basal synaptic transmission in F28-snca transgenic mice (Tg-snca+h9E4 vs. Tg-snca+PBS, p=0.002). However, the reversal by h9E4 was only partial, as indicated by a significantly lower basal synaptic transmission compared to littermates treated with PBS (p=0.007) (Example 7).

Acute treatment with h9E4 induced a significant reversal of the impairment in basal synaptic transmission in F28-snca transgenic mice (Tg-snca+h9E4 vs. Tg-snca+PBS, p=0.002, FIG. 14). However, the reversal by h9E4 was only partial, as indicated by a significantly differentiation to basal synaptic transmission in littermates treated with PBS (p=0.007).

Figure 15:
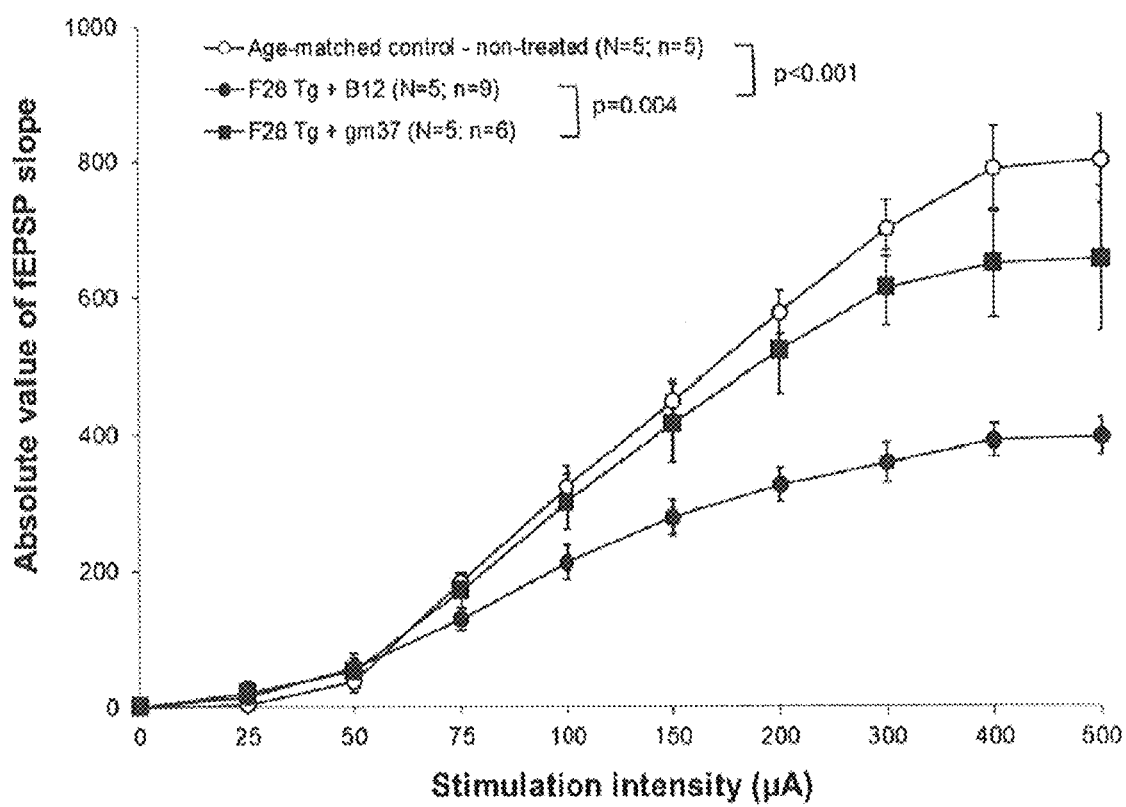
FIG. 15 shows the effect of the systemic administration of a single dose of human GM37 (15 mg/kg, i.p) or an isotype control antibody (B12) on the impairment in basal synaptic transmission at the Schaffer collateral-CA1 synapse in the hippocampus of F28-snca transgenic mice. Field excitatory post-synaptic potentials (fEPSPs) were evoked by a single stimulus applied to the Schaffer collateral, and basal synaptic transmission was assessed by measuring the fEPSP slope as a function of the stimulation intensity. Acute treatment with GM37 induced full reversal of the impairment in basal synaptic transmission in F28-snca transgenic mice (Tg-snca+GM37 vs. Tg-snca+B12, p=0.004) (Example 7).

Acute treatment with GM37 induced a significant reversal of the impairment in basal synaptic transmission in F28-snca transgenic mice (Tg-snca+GM37 vs. Tg-snca+PBS, p=0.004, FIG. 15). Basal synaptic transmission in GM37-treated transgenic mice was not significantly different from basal synaptic transmission in PBS-treated littermates, indicating a full reversal of the impairment (FIG. 15).

Figure 16:
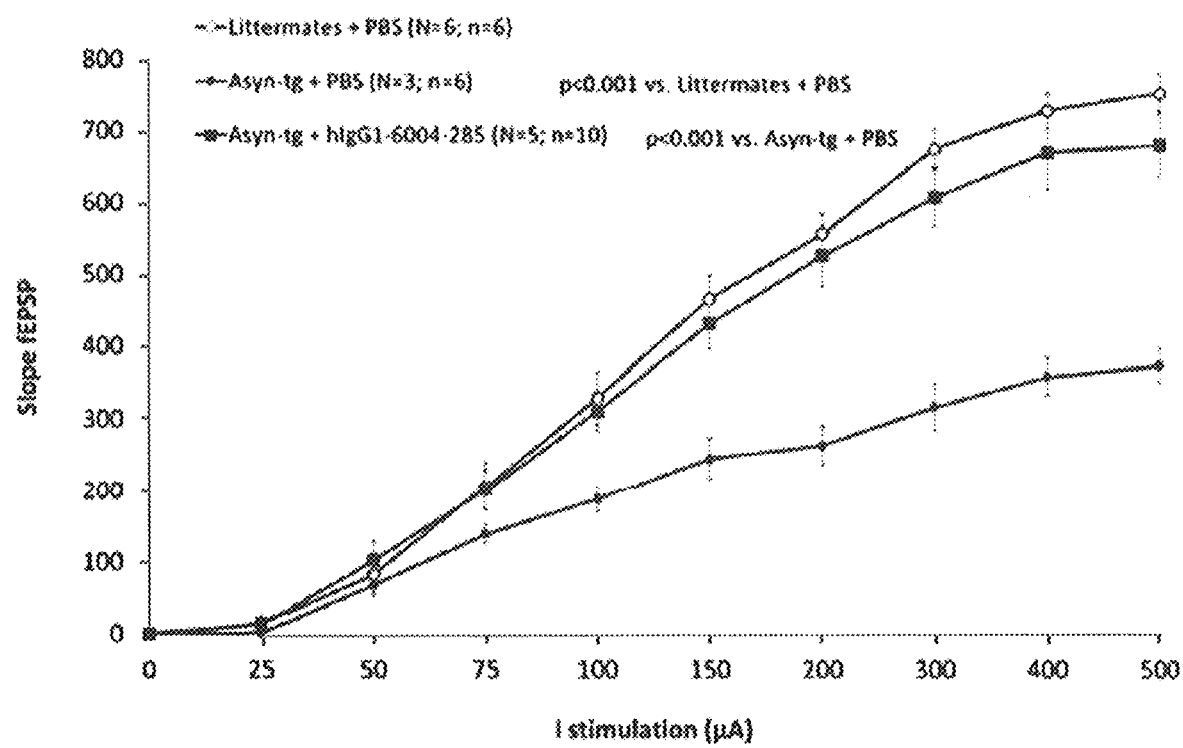
FIG. 16 shows the effect of the systemic administration of a single dose of human GM285 (15 mg/kg, i.p) on the impairments in basal synaptic transmission at the Schaffer collateral-CA1 synapse in the hippocampus of F28-snca transgenic mice. Field excitatory post-synaptic potentials (fEPSPs) were evoked by a single stimulus applied to the Schaffer collateral, and basal synaptic transmission was assessed by measuring the fEPSP slope as a function of the stimulation intensity. Acute treatment with GM285 induced full reversal of the impairment in basal synaptic transmission in F28-snca transgenic mice (Tg-snca+GM285 vs. Tg-snca+PBS, p=0.001) (Example 7).

GM285 also induced a significant reversal of the impairment in basal synaptic transmission in F28-snca transgenic mice (FIG. 16). Basal synaptic transmission in GM285-treated transgenic mice was not significantly different from basal synaptic transmission in PBS-treated littermates, indicating a full reversal of the impairment.

Example 8. Microdialysis to Assess Human Alpha-Synuclein in the Brain of Awake Freely Moving Animals The push-pull microdialysis method was used to assess the levels of human alpha-synuclein in brain interstitial fluid (ISF). Mice were single-housed in controlled temperature (22±1.5° C.) and humidity conditions (55-65%) and kept on a 12:12 hour light/dark cycle (lights on at 06:00 h). Food and water were available ad libitum. The current study was performed in the hippocampus of F28-snca transgenic mice (50-54 weeks old). To enable microdialysis in the hippocampus, mice were anaesthetized with isoflurane and an intracerebral guide cannula (CMA) was stereotaxically implanted into the brain, positioning the microdialysis probe in the hippocampus (co-ordinates of probe tip: 3.1 mm posterior and 2.8 mm lateral from bregma, and 1.3 mm relative dura mater) according to the atlas of Paxinos and Franklin 2001. Anchor screws and acrylic cement were used for the fixation of the guide cannulas. After implantation of the cannula mice were allowed to recover from the surgery for 2-3 days before dialysis.

On the day of the experiment, a 2-mm, 1000 kDa cut-off CMA probe was inserted through the guide cannula. A probe was connected to a microdialysis peristaltic pump with two channels (MAB20; Microbiotech) and operated in push-pull mode. The inlet tubing of the microdialysis probe was connected to a peristaltic pump perfusing the probe with artificial cerebrospinal fluid (aCSF; in mM: 147 NaCl, 2.7 KCl, 1.2 $CaCl_2$, 0.85 $MgCl_2$). The peristaltic pump was also connected to the outlet tubing in order to prevent perfusion fluid loss from the probe, by pulling the fluid through the tubing. As a perfusion buffer, 25% bovine albumin fraction V (Sigma) was diluted to 0.2% with artificial CSF on the day of use and filtered through a 0.1-µm membrane. The actual flow rate of the pump was determined without having the probe connected. The sample tubes were weighed before and after sampling for a given time period and the flow rate was calculated. The pump was then set to a constant flow of 1 µL/min. A 120 min sampling regimen was used throughout the experiment period. To avoid interference of tissue damage, the experimental window was set from 14 to 48 hr after probe implantation. 14-16 h after the start of the experiments, GM37, human 9E4 or isotype control(anti-HEL) were injected i.p. at 15 mg/kg, and an additional 6 samples (12 h of collection) were collected. The dialysates were stored at −80° C. Concentration of human alpha synuclein was determined by ELISA (Covance ELISA kit).

Figure 17A:
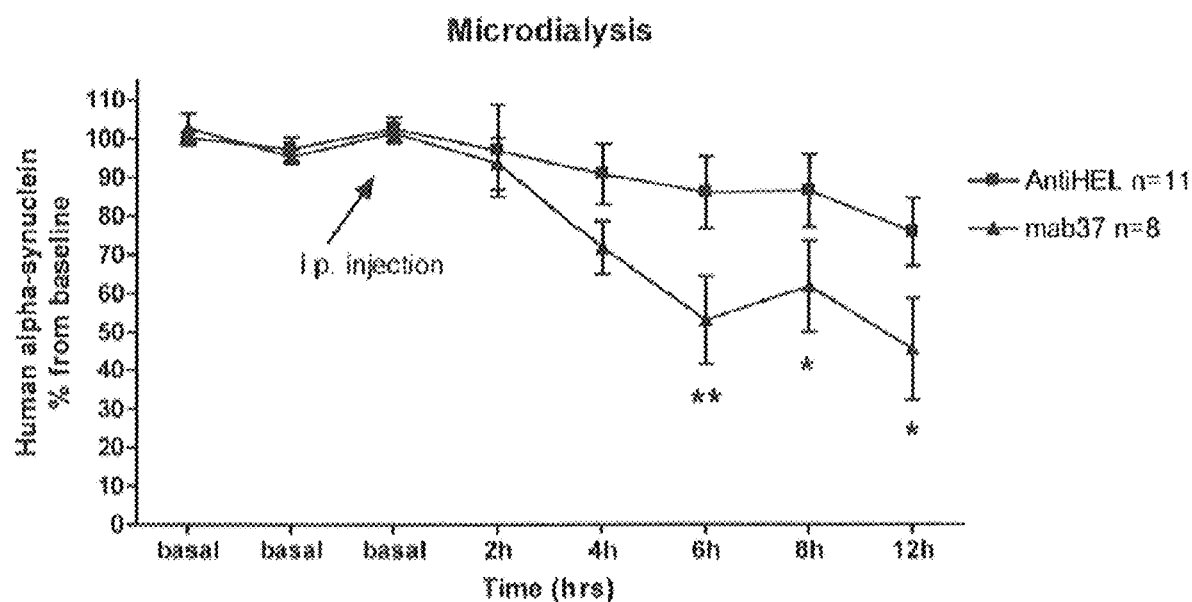
FIGS. 17A and 17B show the effect of the systemic administration (15 mg/kg, i.p.) of human 9E4, GM37 or isotype control antibody (anti-HEL) on the levels of human alpha-synuclein in the interstitial fluid (isf) in the hippocampus of freely moving F28-snca transgenic mice. The average of the two-three basal values (4 h-6 h) prior to antibody treatment was taken as baseline and set to 100% for each animal. Differences were analyzed using a two-way analysis of variance (ANOVA) with repeated measures. The basal levels of human alpha-synuclein in hippocampus were 8.1±1.1 ng/ml (mean±SEM, n=25, not corrected for the in vitro dialysis probe recovery). The administration of GM37 induced a larger reduction in human alpha-synuclein in the hippocampus of F28 mice compared to both the comparator antibody, human 9E4, and the control isotype, anti-HEL Timepoints that show significant differences in the levels of alpha-synuclein between animals treated with GM37 or the control antibody are indicated by an asterisk. (Example 8).
Figure 17B:
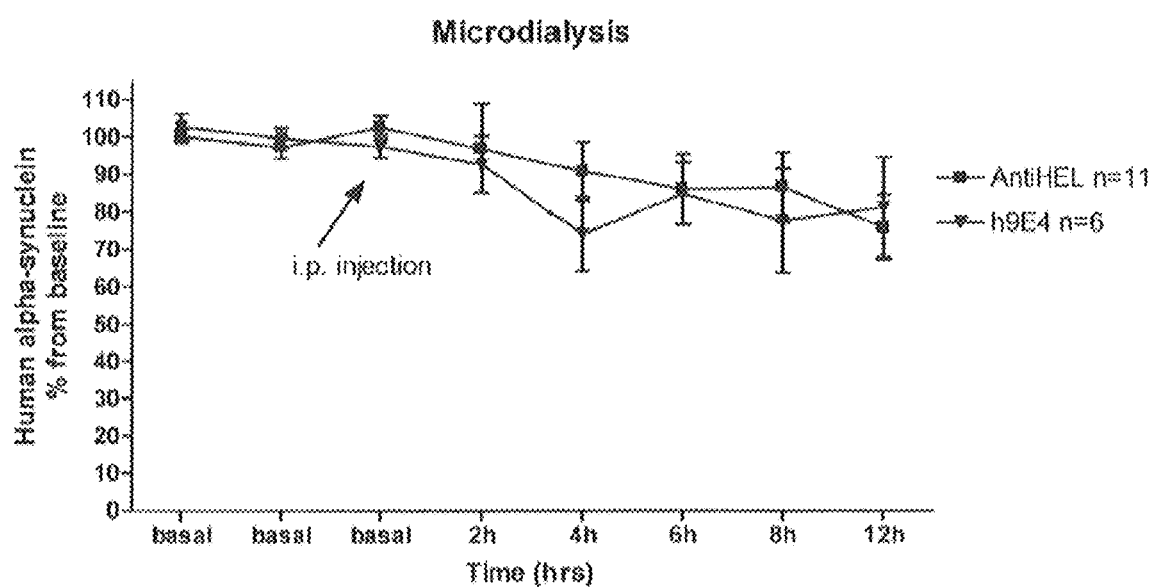

The average of the two-three basal values (4 h-6 h) prior to antibody treatment was taken as baseline and set to 100% for each animal. Data was evaluated using two-way analysis of variance (ANOVA) with repeated measures to evaluate statistical relevance. The basal levels of human alpha-synuclein in hippocampus were 8.1±1.1 ng/ml (mean±SEM, n=25, not corrected for the in vitro dialysis probe recovery). The administration of GM37 induced a larger reduction in human alpha-synuclein in the hippocampus of F28 mice compared to both the comparator antibody, human 9E4, and the isotype control (anti-HEL). (FIG. 17).

Example 9: Chronic Effects of Alpha-Synuclein Antibodies In Vivo. Antibody GM37 Ameliorate Motor Phenotype in Rat Parkinson Model Targeted overexpression of human alpha-synuclein to dopaminergic neurons in the rat midbrain can be achieved using a recombinant adeno-associated viral vector (rAAV) and is associated with a progressive loss of dopaminergic cells in the substantia nigra as well as motor impairments.

Figure 18:
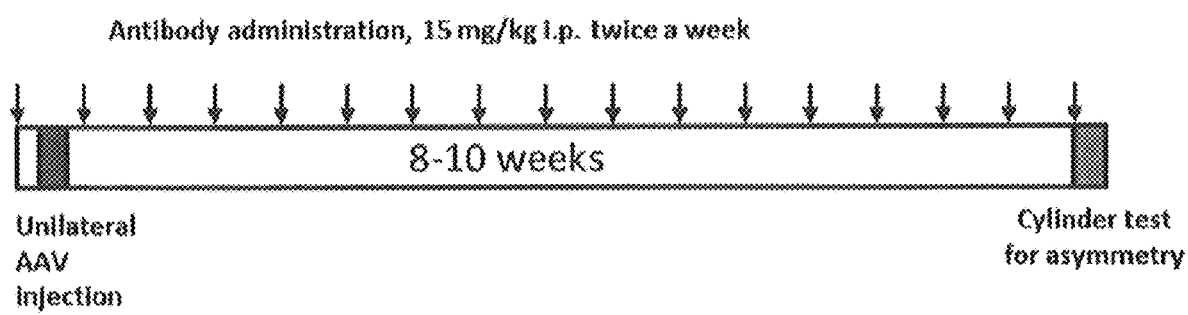
FIG. 18 shows a schematic representation of the timeline for antibody treatment (down arrows), viral injections and behavioural assessment in the rat AAV human alpha-synuclein model shown in FIG. 19 (Example 9).
Figure 19:
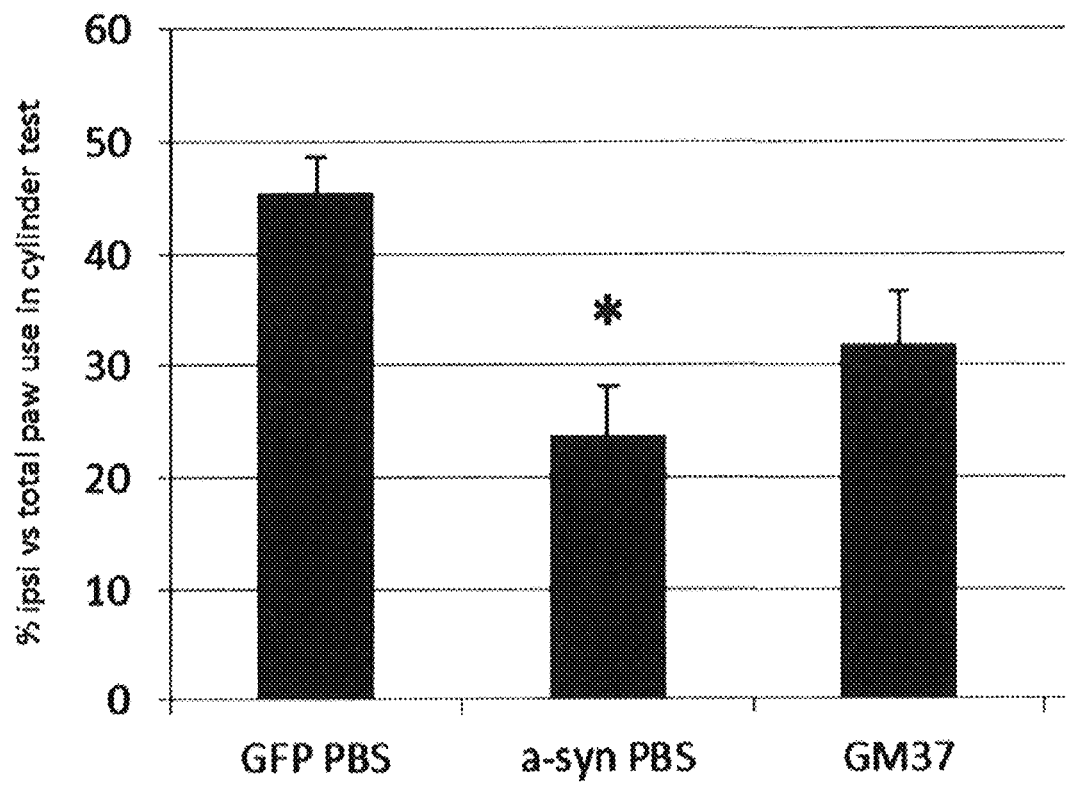
FIG. 19 shows that antibody GM37 can reduce Parkinsonian motor deficits after chronic treatment in the rat AAV model. The effect of chronic treatment with GM37 or PBS in AAV-human-alpha-synuclein rats on motor asymmetry is assessed in the cylinder test. Each rat was tested for the use of the forepaws by monitoring for 5 minutes. The percentage of use of the right forepaw (ipsilateral to the injection) and use of left (contralateral+right forepaws) was calculated for each animal (as shown on the y-axis) *, ** p<0.05 and 0.01 compared to GFP-PBS rats. The rats treated with PBS still have a significant asymmetry in paw use, while animals treated with antibody GM37 have no longer a significant deficit. (Example 9).

Adult female Sprague-Dawley rats (225-250 g) were used to express human alpha-synuclein in substantia nigra (SN) by injection with Adeno associated virus of AAV2/5 serotype containing chicken beta-actin promoter with enhancer elements from the cytomegalovirus promoter, followed by human alpha-synuclein cDNA and WPRE element as previously described (Xu L, Daly T, Gao C, Flotte T R, Song S, Byrne B J, Sands M S, Ponder K P (2001). In this model it has been shown that human alpha-synuclein expression leads to neurodegeneration of dopaminergic neurons. Maingay M, et al. CNS Spectr. 2005 March;10(3):235-44). To test the effect of an alpha synuclein therapeutic antibody in this model antibody treatment was initiated 2 to 4 days prior to viral injections, and continued until the end of the study (FIG. 18). PBS administration at the same volume (5 ml/kg: IP) was used as a control. GM37 was dosed twice per week at a dose of 15 mg/kg (IP). The viral particles (rAAV2/5) containing the gene for human wt alpha-synuclein or green fluorescent protein (GFP) were injected unilaterally in the SN. Animals were anaesthetized with a combination of Hypnorm® and Dormicum® at 2.0 ml/kg s.c. and placed in a stereotaxic frame. Their temperature was adjusted to 37.5° C. via a heating pad, and their skull was exposed. A hole was drilled above the right SN at the following coordinates, according to the atlas of Paxinos and Watson (Paxinos & Watson, 1998): 5.5 mm posterior and 2.0 mm lateral from Bregma. A single injection of 3 μL of rAAV2/5-alpha-syn or rAAV2/5-GFP was performed at a depth of 7.2 mm below the dura matter, and a flow rate of 0.2 μL/min using a Hamilton syringe connected to a stereotaxic injector. The needle was left in place an additional 5 min to allow diffusion of the vector in the SN. Following surgery, the animals were returned to their home cage, and placed in a heated environment where they were allowed to recover from anesthesia. Testing of motor asymmetry in the cylinder test was evaluated prior to AAV injections, as well as 3, 7 and 10 weeks following AAV injections. The data presented correspond to the ratio between use of the right forepaw compared to the total use of both the left and right forepaws. Each animal's performance in the cylinder was filmed for a total 5 min, and manual scoring of the number of touches using the left and right forepaws for 5 minutes has been performed for the final testing day 10 weeks after virus injection. A significant impairment is present in AAV-syn compared to AAV-GFP injected rats (p=0.012) at week 10. A trend for a reversal for GM37 treated animals was shown, as their performance is different from GFP rats (p=0.163 and p=0.407 for gm37, respectively). This finding indicates that antibody GM37 is able to ameliorate the Parkinsonian motor phenotype in this rat model (FIGS. 18 and 19).

Example 10: Chronic Effects of Alpha Synuclein Antibodies In Vivo. Antibody GM37 Inhibits Seeding of Endogenous Mouse Alpha Synuclein Aggregation and Phosphorylation Injection of alpha synuclein preformed fibrils made from recombinant protein into dorsal striatum of wild type mice recruit endogenous mouse alpha synuclein and induce formation of Ser-129 phosphorylated aggregates inside neurons in cortex, amygdala and substantia nigra (Luk et al. 2012, Science. 2012 Nov. 16; 338(6109):949-53). To see if alpha-synuclein specific monoclonal antibody GM37 could reduce the appearance of alpha-synuclein fibril-induced phosphorylated alpha synuclein inclusion formation in vivo a total of 45 mice were used. Mice were dosed with GM 37 at 30 mg/kg i.p, GM 37 15 mg/kg i.v., or vehicle ip (PBS). One day later the mice were anesthetized and stereotactically injected in one hemisphere with 2 ul of recombinant human alpha-Syn crude seeds, made as described previously (Example 6) (total of 2 μg crude seeds per animal). To inject the crude seeds, the skull was opened by boring a hole and a single glass pipette was inserted (co-ordinates: +0.5 mm anterior to Bregma, +2.0 mm lateral to midline) into the right forebrain to target the inoculum to the dorsal neostriatum (+2.6 mm beneath the dura). Following recovery, the mice received weekly i.p. or i.v. injections of antibodies until sacrifice at 45 days. Groups of 15 mice/group were dosed either iv w. GM37 15 mg/kg, ip with GM37 30 mg/kg, or PBS (10 ml/kg) ip once weekly.

To measure the antibody concentration in plasma, cheek blood was drawn once weekly just prior to next injection, ie 7 days after last injection. Plasma was obtained by a 2000 g spin, 15 min incubation at RT, supernatant was subsequently frozen at −20° C. A CSF sample was taken at the end of the study and frozen at −20° C. Plasma and CSF samples were analysed to determine the concentration of Human IgG by MSD. In short, mouse anti-human IgG (clone MH16-1 (M1268) was used for capture, plasma or CSF was incubated in the well, followed by a sulfo-TAG goat anti-human as the detection antibody (MSD cat no: R32AJ-1). Plates were analysed from electrochemiluminesence by MSD.

Figure 20A:
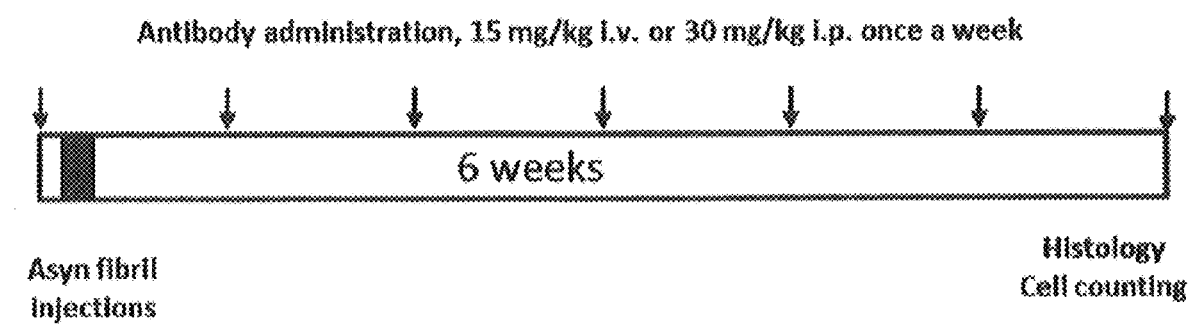
FIGS. 20A-20C show that chronic treatment with antibody GM37 can reduce pathological alpha-synuclein phosphorylation induced by injection of pathological alpha-synuclein fibrillary seeds into the mouse striatum.
Figure 20B:
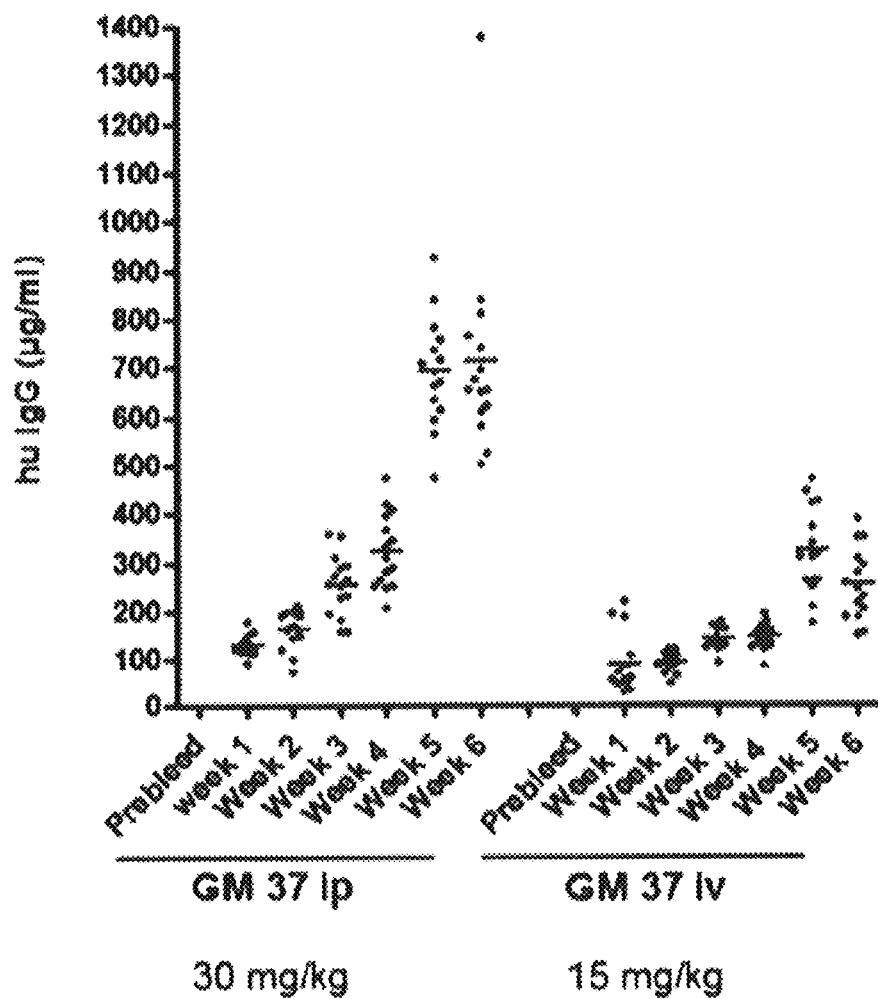

The antibody levels in plasma are shown in FIG. 20B and show a dose dependent increase in antibody plasma concentration and accumulation of antibody in plasma during the six weeks. The antibody levels in csf are shown in FIG. 20C, and show that around 0.1% of antibody level in plasma can be measured in csf.

At day 45, from the time of the injection of the alpha synuclein fibrillary seed, the mice were anesthetized, transcardially perfused with PBS, followed by perfusion with neutral buffered paraformaldehyde (4%). The brains were removed and incubated overnight for post-fixation in neutral buffered paraformaldehyde. Immunohistochemistry was performed on 45 μm thick serial sections by Neuroscience associates. Briefly, Using MultiBrain® technology, up to 25 mouse brains were embedded together per block, into 3 blocks, freeze-sectioned at 45 µm thickness in the coronal plane, and collected into cups containing antigen preserve solution. Every sixth section was stained with antibody to Ser-129 phosphorylated alpha-synuclein (Anti-alpha Synuclein (phospho S129) antibody [Psyn/81A] ab184674) to reveal Ser129 phosphorylated alpha synuclein reactive structures.

Quantitation of pSyn pathology was performed by manual counting immunoreactive positive cells from images at 10× magnification from 5-7 sections covering the entire substantia nigra from every sixth section. The counting was performed blinded. Cell counts in amygdala and nigra were analysed by a one-way ANOVA followed by Bonferoni t-test, where the effect of GM37 antibody was compared to PBS treatment.

Figure 20C:
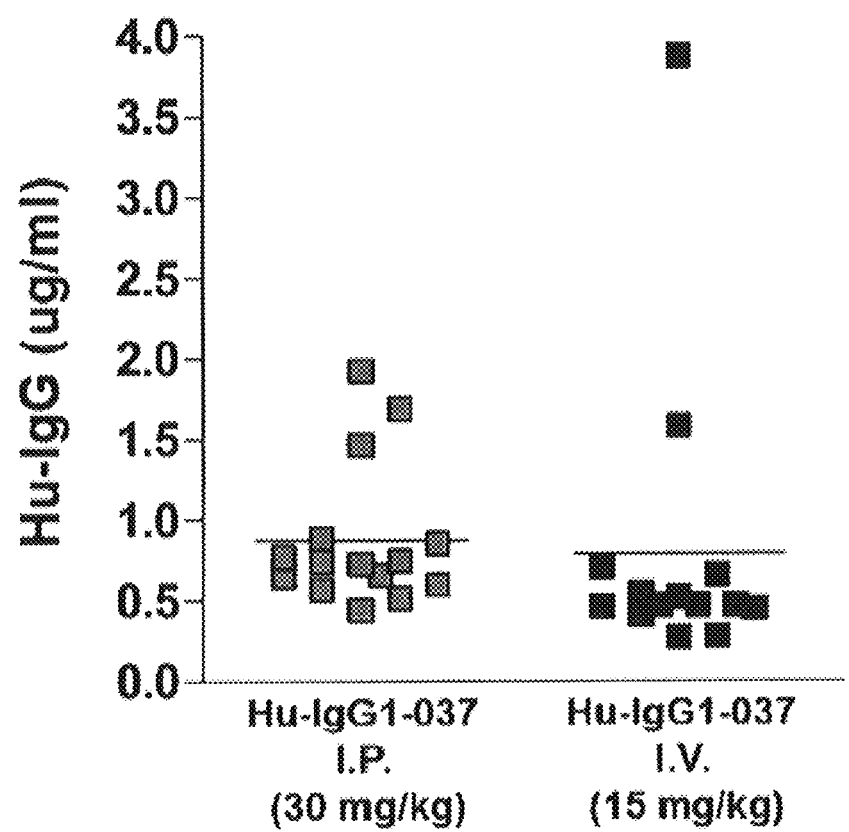
Figure 20D:
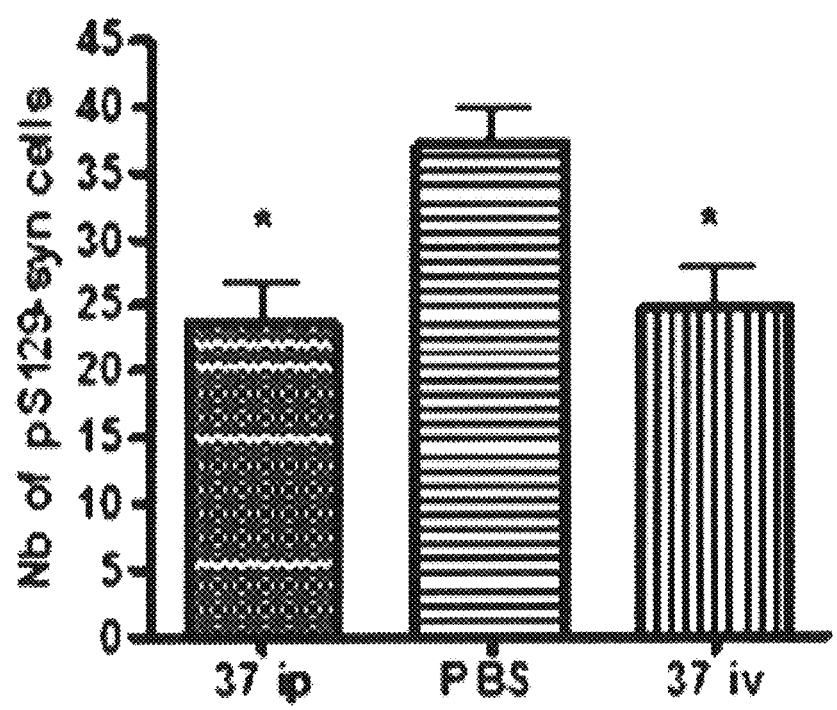
FIG. 20D compares the number of cells with phosphorylated alpha-synuclein positive inclusions counted from every sixth section in substantia nigra after treatment with GM37 or PBS control. The mice treated with GM37 both 15 mg/kg iv and 30 mg/kg ip had a significant reduction in cells with phosphorylated alpha-synuclein inclusions compared to the PBS treated mice (Example 10).

As can be seen from FIG. 20C, treatment with antibody GM37 reduced the number of intra-cellular inclusions in Substantia Nigra significantly when compared to PBS control, with either ip or iv treatment. The data shows that antibody GM37 could have therapeutic effect in PD by blocking entry of extracellular pathological alpha-synuclein into neurons, by blocking its propagation between neurons and/or facilitating clearance from the ISF by uptake into microglia. As this appearance of inclusions has been linked to loss of dopaminergic neurons and development of Parkinsonian motor deficits in animal models, treatment with antibody GM37 could have a therapeutic effect on loss of dopaminergic cells and development of motor deficits in PD.

Example 11: Manufactability of GM37 and GM37 Variants

The anti-alpha-synuclein antibodies are produced in mammalian cell culture under conditions that mimic the production conditions that will be used for producing clinical grade material for use in patients. It is well known that proteins produced in this manner undergo post-translational modifications that can impact both therapeutic potency of the antibody as well as biophysical attributes that affect the stability of the antibody over time. Empirical knowledge ascertained from decades of studies identified a set of post-translational modifications known to provide risk for the developability of a specific molecule. These post-translational modifications have been shown to correlate with amino acid strings present in the primary sequence of the heavy and light chain proteins. Algorithms have been generated that can identify these sequences and determine the potential risk they will have on the manufacturability and developability of a therapeutic antibody.

In silico analysis of the primary sequence of the antibody can be used to de-risk a molecule for its potential to be developed as a therapeutic. In particular, detailed analysis of the VH and VL regions can identified unique amino acids that are deemed important for the molecules activity but also may be a potential risk for its stability over time. Sequence specific deamidation has been identified as a potential risk for protein structures. Protein deamidation can occur on the amide side chains of glutamines or asparagine residues and transform them into a carboxylate group (Lorenzo et al. PLOSone, DOI:10.1371, December (2015)). Nonenzymatic deamidation at neutral pH occurs faster for asparagine and is therefore considered a higher risk than glutamine. The activity is further influenced by the subsequent amino acid in the sequence and can occur at a rate of days or years. The actual fate of the protein that undergoes deamidation needs to be evaluated experimentally to determine the impact of the change both on its stability and activity.

We identified a site for deamidation within the VH domain of GM37. Amino acid residues 54 is an asparagine (N) followed by a glycine(G) at position 55. The N54 is at high risk for spontaneous deamidation. To mitigate this risk we generated a set of 3 variants that replace the asparagine (N) with serine(S), glutamine(Q) or histidine(H). All 3 variants were produced in mammalian cell culture using transient transfection methods (example 1.5). All 3 variants showed similar expression and purification properties as GM37 wt. (FIG. 23).

For each of the eight products 400 ml transient transfections were performed using CHOK1SV GS-KO cells which had been in culture for minimum 2 weeks. Cells were sub-cultured 24 hours prior to transfection. All transfections were carried out via electroporation using Gene Pulse XCell (Bio-Rad). For each transfection, viable cells were resuspended in pre-warmed CD-CHO media supplemented with 6 mM L-glutamine to $2.86 \times 10^7$ cells/ml. 40 µg of each established SGV DNA containing the appropriate heavy and light chains were aliquoted into each cuvette (Bio-Rad, GenePulser cuvette, 0.4 cm gap, 165-2088) and 700 µl cell suspension added. Cells were electroporated at 300V, 900 µF. Transfected cells were transferred to rep-warmed media in Erlenmeyer flasks and the contents of the cuvettes rinsed twice with prewarmed media were also transferred to the flasks. Transfectant cultures were incubated in a shaking incubator at 36.5° C., 5% $CO_2$, 85% humidity, 140 rpm for 6 days. Cell viability was measured at the time of harvest using a Cedex HiRes automated cell counter (Rosche).

Figure 24:
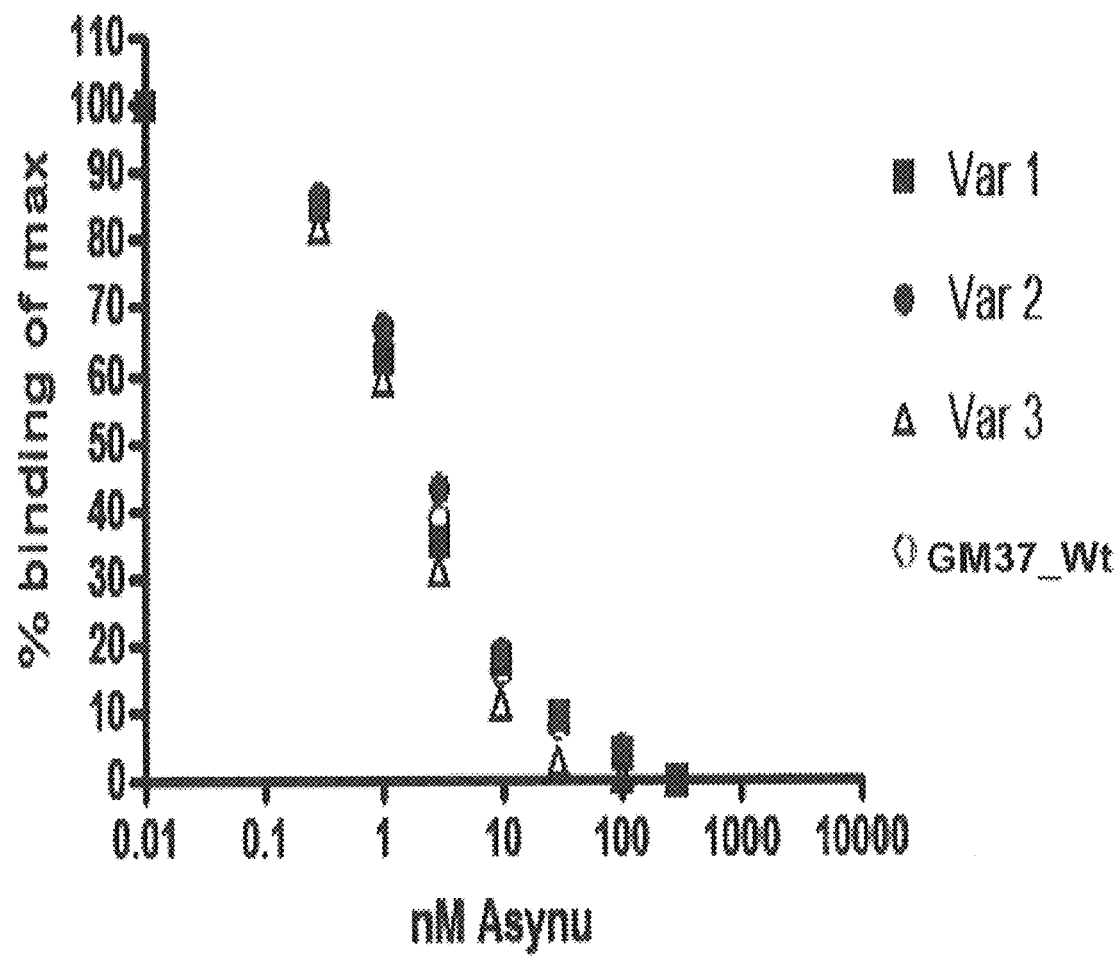
FIG. 24 shows a competition ELISA measuring binding of four antibodies GM37 wt, GM37 var 1, GM37 var 2 and GM37 var 3 to human alpha-synuclein. Plates coated with alpha-synuclein are used to detect the amount of antibody remaining after preincubation in solution of each antibody (0.3 µg/ml) with increasing concentration of alpha-synuclein (0-1000 nM). All four antibodies show similar binding to alpha-synuclein.

In order to evaluate the importance of residue 54 in binding to human alpha-synuclein we analyzed the ability of the variants to bind in two different experiments. Using a competition ELISA format we evaluated the impact the change at residue 54 would have on the ability of GM37 to bind alpha-synuclein in solution. By evaluating the concentration of synuclein able to inhibit binding of the antibody to synuclein coated ELISA plates we showed all three variants maintained the same binding as GM37 wt and bind to alpha-synuclein with high affinity resulting in IC50s of 1-2 nM (FIG. 24). A competition assay was performed using preincubation of a fixed concentration (0.3 µg/ml) of each of the following antibodies, GM37 (named GM 37 wt), GM37 variant1, GM37 variant2 and GM37 variant3 with a range of 0-1000 nM human alpha-synuclein for 60 minutes at room temperature. The remaining unbound antibody was captured and measured on ELISA plates coated with 100 ng/ml of recombinant human alpha-synuclein using an anti-human detection antibody by electrochemiluminesence (MSD, Gathersburg, Md.). The IC50s of the interaction are 1.9 nM, 1.6 nM, 2.1 nM and 1.4 nM for GM37 wt, GM37variant1, GM37variant2 and GM37variant3, respectively (as determined using Prism Graphpad®).

Using surface plasmin resonance (SPR), we evaluated the real time kinetics of binding of GM37 wt (2 batches) and the three variants (Example 2). The human alpha-synuclein was captured to the slide(ligand) and the antibodies were each tested at multiple concentrations as analytes. Analysis of the binding curves in the presence of antibody at multiple concentrations showed that the on rates were the same for all four antibodies, similarly when the antibody was removed from the buffer the off-rates measured showed no statistical difference between the antibodies. Using a 1:1 binding algorithm all 4 antibodies have near identical binding constants (FIG. 25).

Figure 26:
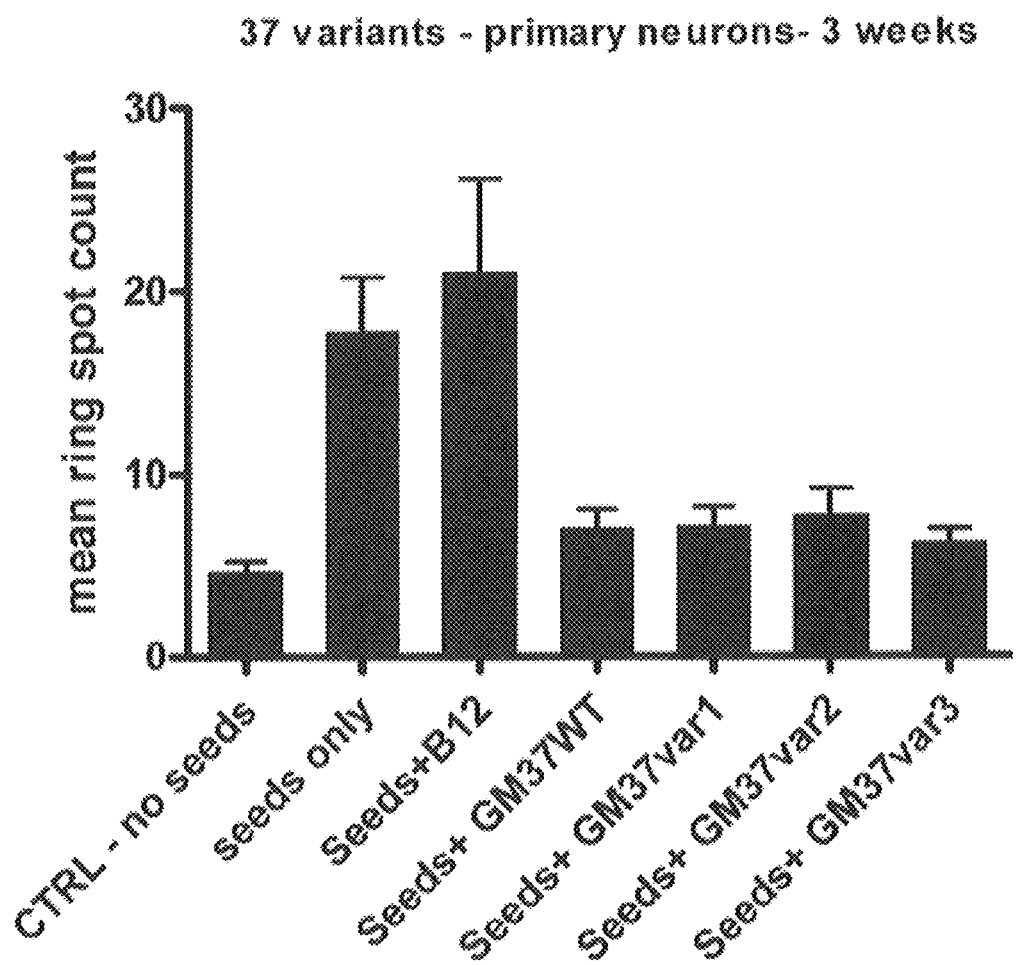
FIG. 26 compares the effect of alpha-synuclein antibodies on phosphorylated alpha-synuclein levels in murine primary neurons treated with pathological alpha-synuclein fibrillary seeds. Primary neurons were treated with seeds (10 ng) in the presence or absence of four GM37, GM37 var 1, GM37 var 2 and GM37 var 3 (2 µg). Neurons were fixed & stained after 3 weeks and analysed by Cellomics ARRAYSCAN™ for alpha-synuclein phospho serine 129 positive spots. Cells treated with seeds alone or with seeds plus the isotype control antibody (B12) show significantly increased levels phosphorylation. Cells treated with GM37 wt and the 3 variants are able to inhibit phosphorylation of alpha-synuclein, they all show the same level of phosphorylation as cells that did not receive seeds. Data is shown as mean±SD as determined from seven images per well in five wells. N=2.

In order to evaluate the impact of the changes at N54 on the functional activity of GM37 we analyzed the ability of the antibodies to block synuclein seeding activity in a culture of primary neurons (Example 6). The level of seeding is measured using an antibody specific for phospho-synuclein. All 3 antibodies were able to block seeding as measured by the phospho-synuclein signal (FIG. 26). Furthermore, the level of inhibition was the same for all 4 antibodies. This call based data further confirms the binding data that amino acid 54 in the VH domain is not required for binding affinity to human alpha-synuclein or for inhibition of seeding in a primary cell based assay. Furthermore, we found that all three of these antibodies were capable of production using standard expression and purification methods. Interestingly one of the variants N54Q showed improvement in production over the other variants, which is of great importance when the antibody is to be produced commercially on large scale. These data support the possibility of reducing the potential risk of deamidation by replacing asparagine (N) with another amino acid without concern over the loss of potency.

A samples of each of the antibodies wt GM37, var1, var2 and vara was subjected to a steady increase in temperature over time and the level of aggregation was simultaneously measured by multi-angle light scattering (Prometheus NT.48, NanoTemper Technologies). The temperature for onset of aggregation was found to be similar for GM37 and the GM37-variants, however the lowest level of aggregation observed for GM37-Var2 (FIG. 27).

The invention claimed is:

1. A method of treating Parkinson's disease or other synucleinopathy in a human subject in need thereof, the method comprising administering to the subject a therapeutically effective amount of an antibody which specifically binds to human alpha-synuclein and comprises heavy chain CDR1, CDR2, and CDR3 comprising the amino acid sequences of SEQ ID NOs:1, 33, and 3, respectively, and light chain CDR1, CDR2, and CDR3 comprising the amino acid sequences of SEQ ID NOs: 4, 5, and 6, respectively.

2. The method of claim 1, wherein the Parkinson's disease is an idiopathic or inherited form of Parkinson's disease.

3. The method of claim 1, wherein the synucleinopathy is selected from Gaucher's Disease, Diffuse Lew Body Disease, Lewy body variant of Alzheimer's disease, combined Alzheimer's and Parkinson's disease, pure autonomic failure, and multiple system atrophy.

4. The method of claim 1, wherein the antibody is which is a single chain Fv, a disulphide-bonded Fv, an Fab fragment, a Fab' fragment, or a F(ab)₂ fragment.

5. The method of claim 1, wherein the antibody is a human antibody.

6. The method of claim 1, wherein the antibody comprises a heavy chain variable domain comprising the amino acid sequence of SEQ ID NO:30 and a light chain variable domain comprising the amino acid sequence of SEQ ID NO:8.

7. The method of claim 1, wherein the antibody binds an epitope within amino acid residues 112-117 (SEQ ID NO:9) of human alpha-synuclein (SEQ ID NO:10).

8. The method of claim 1, wherein the antibody is formulated in a pharmaceutical composition.

9. A method of treating Parkinson's disease in a human subject in need thereof, the method comprising administering to the subject a therapeutically effective amount of an antibody which specifically binds to human alpha-synuclein and comprises heavy chain CDR1, CDR2, and CDR3 comprising the amino acid sequences of SEQ ID NOs: 1, 33, and 3, respectively, and light chain CDR1, CDR2, and CDR3 comprising the amino acid sequences of SEQ ID NOs: 4, 5, and 6, respectively.

10. The method of claim 9, wherein the antibody is which is a single chain Fv, a disulphide-bonded Fv, an Fab fragment, a Fab' fragment, or a F(ab)₂ fragment.

11. The method of claim 9, wherein the antibody is a human antibody.

12. The method of claim 9, wherein the antibody comprises a heavy chain variable domain comprising the amino acid sequence of SEQ ID NO:30 and a light chain variable domain comprising the amino acid sequence of SEQ ID NO:8.

13. The method of claim 9, wherein the antibody binds an epitope within amino acid residues 112-117 (SEQ ID NO:9) of human alpha-synuclein (SEQ ID NO:10).

14. The method of claim 9, wherein the antibody is formulated in a pharmaceutical composition.

* * * * *

UNITED STATES PATENT AND TRADEMARK OFFICE
CERTIFICATE OF CORRECTION

PATENT NO. : 10,647,763 B2
APPLICATION NO. : 16/443187
DATED : May 12, 2020
INVENTOR(S) : Pekka Kallunki et al.

Page 1 of 1

It is certified that error appears in the above-identified patent and that said Letters Patent is hereby corrected as shown below:

In the Claims

At Column 93, Claim number 3, Line number 57, delete "Diffuse Lew Body" and insert
--Diffuse Lewy Body--.

At Column 93, Claim number 4, Line number 61, delete "is which".

At Column 94, Claim number 10, Line number 61, delete "is which".

Signed and Sealed this
Twenty-third Day of June, 2020

Andrei Iancu
*Director of the United States Patent and Trademark Office*

SEQUENCE LISTING

```
<160> NUMBER OF SEQ ID NOS: 43

<210> SEQ ID NO 1
<211> LENGTH: 10
<212> TYPE: PRT
<213> ORGANISM: Artificial
<220> FEATURE:
<223> OTHER INFORMATION: GM37 CDR 1 Heavy Chain

<400> SEQUENCE: 1

Gly Phe Thr Phe Ser Ser Tyr Ala Met Thr
1               5                   10

<210> SEQ ID NO 2
<211> LENGTH: 17
<212> TYPE: PRT
<213> ORGANISM: Artificial
<220> FEATURE:
<223> OTHER INFORMATION: GM37 CDR2 Heavy Chain

<400> SEQUENCE: 2

Ala Ile Arg Ser Asn Gly Asp Arg Thr Asp Tyr Ala Asp Ser Val Lys
1               5                   10                  15

Gly

<210> SEQ ID NO 3
<211> LENGTH: 9
<212> TYPE: PRT
<213> ORGANISM: Artificial
<220> FEATURE:
<223> OTHER INFORMATION: GM37 CDR3 Heavy Chain

<400> SEQUENCE: 3

Ala Lys Asn Trp Ala Pro Phe Asp Ser
1               5

<210> SEQ ID NO 4
<211> LENGTH: 11
<212> TYPE: PRT
<213> ORGANISM: Artificial
<220> FEATURE:
<223> OTHER INFORMATION: GM37 CDR1 Light Chain

<400> SEQUENCE: 4

Ala Ser Gln Ser Val Ser Ser Ser Tyr Leu Ala
1               5                   10

<210> SEQ ID NO 5
<211> LENGTH: 7
<212> TYPE: PRT
<213> ORGANISM: Artificial
<220> FEATURE:
```

<223> OTHER INFORMATION: GM37 CDR 2 Light Chain

<400> SEQUENCE: 5

Gly Ala Ser Ser Arg Ala Thr
1               5

<210> SEQ ID NO 6
<211> LENGTH: 9
<212> TYPE: PRT
<213> ORGANISM: Artificial
<220> FEATURE:
<223> OTHER INFORMATION: GM37 CDR 3 Light Chain

<400> SEQUENCE: 6

Gln Gln Tyr Gly Ser Ser Pro Trp Thr
1               5

<210> SEQ ID NO 7
<211> LENGTH: 116
<212> TYPE: PRT
<213> ORGANISM: Artificial
<220> FEATURE:
<223> OTHER INFORMATION: GM37 CDR Heavy Chain

<400> SEQUENCE: 7

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Arg Ser Asn Gly Asp Arg Thr Asp Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Trp Ala Pro Phe Asp Ser Trp Gly Gln Gly Thr Leu Val
            100                 105                 110

Thr Val Ser Ser
        115

<210> SEQ ID NO 8
<211> LENGTH: 108
<212> TYPE: PRT
<213> ORGANISM: Artificial
<220> FEATURE:
<223> OTHER INFORMATION: GM 37 Light Chain

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 9
<211> LENGTH: 6
<212> TYPE: PRT
<213> ORGANISM: Artificial
<220> FEATURE:
<223> OTHER INFORMATION: Epitope 112-117

<400> SEQUENCE: 9

Ile Leu Glu Asp Met Pro
1               5

<210> SEQ ID NO 10
<211> LENGTH: 140
<212> TYPE: PRT
<213> ORGANISM: Artificial
<220> FEATURE:
<223> OTHER INFORMATION: Alpha-synuclein

<400> SEQUENCE: 10

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 11
<211> LENGTH: 165
<212> TYPE: PRT
<213> ORGANISM: Artificial
<220> FEATURE:
<223> OTHER INFORMATION: A-Syn-AAKK-BAP

<400> SEQUENCE: 11

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
```

```
                65                  70                  75                  80
Thr Val Glu Gly Ala Gly Asn Ile Ala Ala Thr Gly Leu Val Lys
                85                  90                  95

Lys Asp Gln Leu Ala Lys Gln Asn Glu Glu Gly Phe Leu Gln Glu Gly
                100                 105                 110

Met Val Asn Asn Thr Asp Ile Pro Val Asp Pro Glu Asn Glu Ala Tyr
                115                 120                 125

Glu Met Pro Pro Glu Glu Tyr Gln Asp Tyr Glu Pro Glu Ala Gly
    130                 135                 140

Ser Ala Gly Gly Ser Gly Gly Leu Asn Asp Ile Phe Glu Ala Gln Lys
145                 150                 155                 160

Ile Glu Trp His Glu
                165

<210> SEQ ID NO 12
<211> LENGTH: 165
<212> TYPE: PRT
<213> ORGANISM: Artificial
<220> FEATURE:
<223> OTHER INFORMATION: A-Syn-BAAK-BAP

<400> SEQUENCE: 12

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
                20                  25                  30

Thr Lys Glu Gly Val Leu Tyr Val Gly Ser Lys Thr Lys Glu Gly Val
                35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Ala Lys Gln Asn Glu Glu Gly Phe Leu Gln Glu Gly
                100                 105                 110

Met Val Asn Asn Thr Asp Ile Pro Val Asp Pro Glu Asn Glu Ala Tyr
                115                 120                 125

Glu Met Pro Pro Glu Glu Tyr Gln Asp Tyr Glu Pro Glu Ala Gly
    130                 135                 140

Ser Ala Gly Gly Ser Gly Gly Leu Asn Asp Ile Phe Glu Ala Gln Lys
145                 150                 155                 160

Ile Glu Trp His Glu
                165

<210> SEQ ID NO 13
<211> LENGTH: 162
<212> TYPE: PRT
<213> ORGANISM: Artificial
<220> FEATURE:
<223> OTHER INFORMATION: A-Syn-BBAA-BAP

<400> SEQUENCE: 13

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
                20                  25                  30
```

```
Thr Lys Glu Gly Val Leu Tyr Val Gly Ser Lys Thr Arg Glu Gly Val
         35                  40                  45

Val Gln Gly Val Ala Ser Val Ala Glu Lys Thr Lys Glu Gln Ala Ser
 50                  55                  60

His Leu Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Gly Ser Ala Gly
        130                 135                 140

Gly Ser Gly Gly Leu Asn Asp Ile Phe Glu Ala Gln Lys Ile Glu Trp
145                 150                 155                 160

His Glu

<210> SEQ ID NO 14
<211> LENGTH: 165
<212> TYPE: PRT
<213> ORGANISM: Artificial
<220> FEATURE:
<223> OTHER INFORMATION: A-Syn-BBKK-BAP

<400> SEQUENCE: 14

Met Asp Val Phe Met Lys Gly Leu Ser Met Ala Lys Glu Gly Val Val
 1               5                  10                  15

Ala Ala Ala Glu Lys Thr Lys Gln Gly Val Thr Glu Ala Ala Glu Lys
             20                  25                  30

Thr Lys Glu Gly Val Leu Tyr Val Gly Ser Lys Thr Arg Glu Gly Val
         35                  40                  45

Val Gln Gly Val Ala Ser Val Ala Glu Lys Thr Lys Glu Gln Ala Ser
 50                  55                  60

His Leu Gly Gly Ala Val Val Thr Gly Val Thr Ala Val Ala Gln Lys
 65                  70                  75                  80

Thr Val Glu Gly Ala Gly Asn Ile Ala Ala Ala Thr Gly Leu Val Lys
                 85                  90                  95

Lys Asp Gln Leu Ala Lys Gln Asn Glu Glu Gly Phe Leu Gln Glu Gly
                100                 105                 110

Met Val Asn Asn Thr Asp Ile Pro Val Asp Pro Glu Asn Glu Ala Tyr
            115                 120                 125

Glu Met Pro Pro Glu Glu Glu Tyr Gln Asp Tyr Glu Pro Glu Ala Gly
        130                 135                 140

Ser Ala Gly Gly Ser Gly Gly Leu Asn Asp Ile Phe Glu Ala Gln Lys
145                 150                 155                 160

Ile Glu Trp His Glu
                165

<210> SEQ ID NO 15
<211> LENGTH: 141
<212> TYPE: PRT
<213> ORGANISM: Artificial
<220> FEATURE:
<223> OTHER INFORMATION: A-Syn-120-140_Del-BAP

<400> SEQUENCE: 15
```

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Gly Ser Ala Gly Gly Ser Gly Gly Leu
            115                 120                 125

Asn Asp Ile Phe Glu Ala Gln Lys Ile Glu Trp His Glu
            130                 135                 140

<210> SEQ ID NO 16
<211> LENGTH: 131
<212> TYPE: PRT
<213> ORGANISM: Artificial
<220> FEATURE:
<223> OTHER INFORMATION: alpha-synuclein amino acids 1-119

<400> SEQUENCE: 16

Met Ala His His His His His His Ile Glu Gly Arg Met Asp Val Phe
1               5                   10                  15

Met Lys Gly Leu Ser Lys Ala Lys Glu Gly Val Val Ala Ala Ala Glu
            20                  25                  30

Lys Thr Lys Gln Gly Val Ala Glu Ala Ala Gly Lys Thr Lys Glu Gly
        35                  40                  45

Val Leu Tyr Val Gly Ser Lys Thr Lys Glu Gly Val Val His Gly Val
    50                  55                  60

Ala Thr Val Ala Glu Lys Thr Lys Glu Gln Val Thr Asn Val Gly Gly
65                  70                  75                  80

Ala Val Val Thr Gly Val Thr Ala Val Ala Gln Lys Thr Val Glu Gly
            85                  90                  95

Ala Gly Ser Ile Ala Ala Ala Thr Gly Phe Val Lys Lys Asp Gln Leu
            100                 105                 110

Gly Lys Asn Glu Glu Gly Ala Pro Gln Glu Gly Ile Leu Glu Asp Met
            115                 120                 125

Pro Val Asp
    130

<210> SEQ ID NO 17
<211> LENGTH: 106
<212> TYPE: PRT
<213> ORGANISM: artificial
<220> FEATURE:
<223> OTHER INFORMATION: kappa (LC constant region)

<400> SEQUENCE: 17

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

```
Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 18
<211> LENGTH: 329
<212> TYPE: PRT
<213> ORGANISM: Artificial
<220> FEATURE:
<223> OTHER INFORMATION: IgG1 (HC Constant region)

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 4
<212> TYPE: PRT
<213> ORGANISM: Artificial
<220> FEATURE:
<223> OTHER INFORMATION: GM285 epitope 112-115

<400> SEQUENCE: 19

Ile Leu Glu Asp
1

<210> SEQ ID NO 20
<211> LENGTH: 13
<212> TYPE: PRT
<213> ORGANISM: Artificial
<220> FEATURE:
<223> OTHER INFORMATION: GM285 CDR1 Heavy Chain

<400> SEQUENCE: 20

Ala Ala Ser Gly Phe Thr Phe Ser Arg Phe Thr Met Thr
1               5                   10

<210> SEQ ID NO 21
<211> LENGTH: 17
<212> TYPE: PRT
<213> ORGANISM: Artificial
<220> FEATURE:
<223> OTHER INFORMATION: GM285 CDR2 Heavy Chain

<400> SEQUENCE: 21

Ala Ile Ser Gly Ser Gly Gly Gly Thr Ser Tyr Ala Asp Ser Val Lys
1               5                   10                  15

Gly

<210> SEQ ID NO 22
<211> LENGTH: 9
<212> TYPE: PRT
<213> ORGANISM: Artificial
<220> FEATURE:
<223> OTHER INFORMATION: GM285 CDR3 Heavy Chain

<400> SEQUENCE: 22

Ala Lys Asn Trp Ala Pro Phe Asp Tyr
1               5

<210> SEQ ID NO 23
<211> LENGTH: 12
<212> TYPE: PRT
<213> ORGANISM: Artificial
<220> FEATURE:
<223> OTHER INFORMATION: GM285 CDR1 Light Chain

<400> SEQUENCE: 23

Arg Ala Ser Gln Ser Val Ser Arg Ser Tyr Leu Ala
1               5                   10

<210> SEQ ID NO 24
```

```
<211> LENGTH: 7
<212> TYPE: PRT
<213> ORGANISM: Artificial
<220> FEATURE:
<223> OTHER INFORMATION: GM285 CDR2 Light Chain

<400> SEQUENCE: 24

Gly Ala Ser Ser Arg Ala Thr
1               5

<210> SEQ ID NO 25
<211> LENGTH: 9
<212> TYPE: PRT
<213> ORGANISM: Artificial
<220> FEATURE:
<223> OTHER INFORMATION: GM285 CDR3 Light Chain

<400> SEQUENCE: 25

Gln Gln Tyr Gly Ser Ser Pro Trp Thr
1               5

<210> SEQ ID NO 26
<211> LENGTH: 116
<212> TYPE: PRT
<213> ORGANISM: Artificial
<220> FEATURE:
<223> OTHER INFORMATION: GM285 VH

<400> SEQUENCE: 26

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Arg Phe
            20                  25                  30

Thr Met Thr Trp Val Arg Gln Ala Pro Gly Lys Gly Leu Glu Trp Val
        35                  40                  45

Ser Ala Ile Ser Gly Ser Gly Gly Thr Ser Tyr Ala Asp Ser Val
    50                  55                  60

Lys Gly Arg Leu Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Trp Ala Pro Phe Asp Tyr Trp Gly Gln Gly Thr Leu Val
            100                 105                 110

Thr Val Ser Ser
        115

<210> SEQ ID NO 27
<211> LENGTH: 108
<212> TYPE: PRT
<213> ORGANISM: Artificial
<220> FEATURE:
<223> OTHER INFORMATION: GM285 VL

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Val Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 28
<211> LENGTH: 329
<212> TYPE: PRT
<213> ORGANISM: Artificial
<220> FEATURE:
<223> OTHER INFORMATION: GM285 IgG1 constant region

<400> SEQUENCE: 28

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly
            325

<210> SEQ ID NO 29
<211> LENGTH: 106
<212> TYPE: PRT
<213> ORGANISM: Artificial
<220> FEATURE:
<223> OTHER INFORMATION: GM285 Kappa chain

<400> SEQUENCE: 29

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 30
<211> LENGTH: 116
<212> TYPE: PRT
<213> ORGANISM: Artificial
<220> FEATURE:
<223> OTHER INFORMATION: GM37 Variant 1 heavy chain

<400> SEQUENCE: 30

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Arg Ser Ser Gly Asp Arg Thr Asp Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Trp Ala Pro Phe Asp Ser Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: GM 37 variant 2 heavy chain

<400> SEQUENCE: 31
```

```
Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Arg Ser Gln Gly Asp Arg Thr Asp Tyr Ala Asp Ser Val
50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Trp Ala Pro Phe Asp Ser Trp Gly Gln Gly Thr Leu Val
            100                 105                 110

Thr Val Ser Ser
        115
```

<210> SEQ ID NO 32
<211> LENGTH: 116
<212> TYPE: PRT
<213> ORGANISM: Artificial
<220> FEATURE:
<223> OTHER INFORMATION: GM 37 variant 3 heavy chain

<400> SEQUENCE: 32

```
Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Arg Ser His Gly Asp Arg Thr Asp Tyr Ala Asp Ser Val
50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Trp Ala Pro Phe Asp Ser Trp Gly Gln Gly Thr Leu Val
            100                 105                 110

Thr Val Ser Ser
        115
```

<210> SEQ ID NO 33
<211> LENGTH: 17
<212> TYPE: PRT
<213> ORGANISM: Artificial
<220> FEATURE:
<223> OTHER INFORMATION: GM37 variant 1 heavy chain CDR 2

<400> SEQUENCE: 33

```
Ala Ile Arg Ser Ser Gly Asp Arg Thr Asp Tyr Ala Asp Ser Val Lys
1               5                   10                  15

Gly
```

<210> SEQ ID NO 34
<211> LENGTH: 17
<212> TYPE: PRT
<213> ORGANISM: Artificial
<220> FEATURE:

<223> OTHER INFORMATION: GM37 variant 2 CDR 2 heavy chain

<400> SEQUENCE: 34

Ala Ile Arg Ser Gln Gly Asp Arg Thr Asp Tyr Ala Asp Ser Val Lys
1               5                   10                  15

Gly

<210> SEQ ID NO 35
<211> LENGTH: 17
<212> TYPE: PRT
<213> ORGANISM: Artificial
<220> FEATURE:
<223> OTHER INFORMATION: GM37 variant 3 CDR 2 heavy chain

<400> SEQUENCE: 35

Ala Ile Arg Ser His Gly Asp Arg Thr Asp Tyr Ala Asp Ser Val Lys
1               5                   10                  15

Gly

<210> SEQ ID NO 36
<211> LENGTH: 5
<212> TYPE: PRT
<213> ORGANISM: Artificial
<220> FEATURE:
<223> OTHER INFORMATION: 9E4 binding epitope

<400> SEQUENCE: 36

Asn Glu Ala Tyr Glu
1               5

<210> SEQ ID NO 37
<211> LENGTH: 134
<212> TYPE: PRT
<213> ORGANISM: Artificial
<220> FEATURE:
<223> OTHER INFORMATION: HUMAN Beta-synuclein

<400> SEQUENCE: 37

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45

Val Gln Gly Val Ala Ser Val Ala Glu Lys Thr Lys Glu Gln Ala Ser
    50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95

Glu Val Ala Gln Glu Ala Ala Glu Glu Pro Leu Ile Glu Pro Leu Met
            100                 105                 110

Glu Pro Glu Gly Glu Ser Tyr Glu Asp Pro Pro Gln Glu Glu Tyr Gln
        115                 120                 125

Glu Tyr Glu Pro Glu Ala
    130

<210> SEQ ID NO 38
<211> LENGTH: 127
<212> TYPE: PRT
<213> ORGANISM: Artificial

<220> FEATURE:
<223> OTHER INFORMATION: HUMAN Gamma-synuclein

<400> SEQUENCE: 38

Met Asp Val Phe Lys Lys Gly Phe Ser Ile Ala Lys Glu Gly Val Val
1               5                   10                  15

Gly Ala Val Glu Lys Thr Lys Gln Gly Val Thr Glu Ala Ala Glu Lys
            20                  25                  30

Thr Lys Glu Gly Val Met Tyr Val Gly Ala Lys Thr Lys Glu Asn Val
        35                  40                  45

Val Gln Ser Val Thr Ser Val Ala Glu Lys Thr Lys Glu Gln Ala Asn
    50                  55                  60

Ala Val Ser Glu Ala Val Val Ser Ser Val Asn Thr Val Ala Thr Lys
65                  70                  75                  80

Thr Val Glu Glu Ala Glu Asn Ile Ala Val Thr Ser Gly Val Val Arg
                85                  90                  95

Lys Glu Asp Leu Arg Pro Ser Ala Pro Gln Gln Glu Gly Glu Ala Ser
            100                 105                 110

Lys Glu Lys Glu Glu Val Ala Glu Ala Gln Ser Gly Gly Asp
        115                 120                 125

<210> SEQ ID NO 39
<211> LENGTH: 140
<212> TYPE: PRT
<213> ORGANISM: Artificial
<220> FEATURE:
<223> OTHER INFORMATION: alpha-synuclein ortholog for Cynomolgus monkey

<400> SEQUENCE: 39

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Ile Lys
                85                  90                  95

Lys Asp Gln Leu Gly Lys Asn Glu Glu Gly Ala Pro Gln Glu Gly Ile
            100                 105                 110

Leu Gln Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 40
<211> LENGTH: 140
<212> TYPE: PRT
<213> ORGANISM: Artificial
<220> FEATURE:
<223> OTHER INFORMATION: alpha-synuclein ortholog for Rat

<400> SEQUENCE: 40

Met Asp Val Phe Met Lys Gly Leu Ser Lys Ala Lys Glu Gly Val Val
1               5                   10                  15

```
Ala Ala Ala Glu Lys Thr Lys Gln Gly Val Ala Glu Ala Ala Gly Lys
             20                  25                  30

Thr Lys Glu Gly Val Leu Tyr Val Gly Ser Lys Thr Lys Glu Gly Val
         35                  40                  45

Val His Gly Val Thr Thr Val Ala Glu Lys Thr Lys Glu Gln Val Thr
     50                  55                  60

Asn Val Gly Gly Ala Val Val Thr Gly Val Thr Ala Val Ala Gln Lys
65                  70                  75                  80

Thr Val Glu Gly Ala Gly Asn Ile Ala Ala Thr Gly Phe Val Lys
                 85                  90                  95

Lys Asp Gln Met Gly Lys Gly Glu Glu Gly Tyr Pro Gln Glu Gly Ile
                100                 105                 110

Leu Glu Asp Met Pro Val Asp Pro Ser Ser Glu Ala Tyr Glu Met Pro
                115                 120                 125

Ser Glu Glu Gly Tyr Gln Asp Tyr Glu Pro Glu Ala
            130                 135                 140

<210> SEQ ID NO 41
<211> LENGTH: 140
<212> TYPE: PRT
<213> ORGANISM: Artificial
<220> FEATURE:
<223> OTHER INFORMATION: alpha-synuclein ortholog for Mouse

<400> SEQUENCE: 41

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
             20                  25                  30

Thr Lys Glu Gly Val Leu Tyr Val Gly Ser Lys Thr Lys Glu Gly Val
         35                  40                  45

Val His Gly Val Thr Thr Val Ala Glu Lys Thr Lys Glu Gln Val Thr
     50                  55                  60

Asn Val Gly Gly Ala Val Val Thr Gly Val Thr Ala Val Ala Gln Lys
65                  70                  75                  80

Thr Val Glu Gly Ala Gly Asn Ile Ala Ala Thr Gly Phe Val Lys
                 85                  90                  95

Lys Asp Gln Met Gly Lys Gly Glu Glu Gly Tyr Pro Gln Glu Gly Ile
                100                 105                 110

Leu Glu Asp Met Pro Val Asp Pro Gly Ser Glu Ala Tyr Glu Met Pro
                115                 120                 125

Ser Glu Glu Gly Tyr Gln Asp Tyr Glu Pro Glu Ala
            130                 135                 140

<210> SEQ ID NO 42
<211> LENGTH: 446
<212> TYPE: PRT
<213> ORGANISM: artificial
<220> FEATURE:
<223> OTHER INFORMATION: 9E4 HC

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
             20                  25                  30

Gly Met Ser Trp Val Arg Gln Ala Pro Gly Lys Gly Leu Glu Trp Val
         35                  40                  45
```

Ala Ser Ile Ser Ser Gly Gly Ser Thr Tyr Tyr Pro Asp Asn Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Gly Gly Ala Gly Ile Asp Tyr Trp Gly Gln Gly Thr Leu Val
             100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
     130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Lys Arg Val Glu Pro Lys Ser Cys Asp Lys Thr His Thr
     210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
             260                 265                 270

Lys Phe Asn Trp Tyr Val Asp Gly Val Glu Val His Asn Ala Lys Thr
         275                 280                 285

Lys Pro Arg Glu Glu Gln Tyr Asn Ser Thr Tyr Arg Val Val Ser Val
     290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Arg Glu Glu Met Thr Lys Asn Gln Val Ser Leu Thr Cys Leu Val
         355                 360                 365

Lys Gly Phe Tyr Pro Ser Asp Ile Ala Val Glu Trp Glu Ser Asn Gly
     370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                 405                 410                 415

Gln Gln Gly Asn Val Phe Ser Cys Ser Val Met His Glu Ala Leu His
             420                 425                 430

Asn His Tyr Thr Gln Lys Ser Leu Ser Leu Ser Pro Gly Lys
         435                 440                 445

<210> SEQ ID NO 43
<211> LENGTH: 220

```
<212> TYPE: PRT
<213> ORGANISM: artificial
<220> FEATURE:
<223> OTHER INFORMATION: 9E4 LC

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220
```